US011235037B2

United States Patent
Almassy et al.

(10) Patent No.: US 11,235,037 B2
(45) Date of Patent: *Feb. 1, 2022

(54) ARGININE DEIMINASE WITH REDUCED CROSS-REACTIVITY TOWARD ADI - PEG 20 ANTIBODIES FOR CANCER TREATMENT

(71) Applicant: Polaris Group, Grand Cayman (KY)

(72) Inventors: Robert Almassy, Vista, CA (US); Richard E. Showalter, El Cajon, CA (US); James A. Thomson, San Diego, CA (US); Wes Sisson, San Diego, CA (US); Wei-Jong Shia, San Diego, CA (US); Li-Chang Chen, San Diego, CA (US); Yang Lee, San Diego, CA (US)

(73) Assignee: Polaris Group, Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 14/214,040

(22) Filed: Mar. 14, 2014

(65) Prior Publication Data

US 2014/0348814 A1  Nov. 27, 2014

Related U.S. Application Data

(60) Provisional application No. 61/790,833, filed on Mar. 15, 2013.

(51) Int. Cl.
*A61K 38/50*  (2006.01)
*C12N 9/78*  (2006.01)
*A61K 45/06*  (2006.01)

(52) U.S. Cl.
CPC ............ *A61K 38/50* (2013.01); *A61K 45/06* (2013.01); *C12N 9/78* (2013.01); *C12Y 305/03006* (2013.01)

(58) Field of Classification Search
CPC ............................................. C12Y 305/03006
USPC ......................................................... 435/227
See application file for complete search history.

(56) References Cited

U.S. PATENT DOCUMENTS

| | | | |
|---|---|---|---|
| 5,474,928 A | 12/1995 | Takaku et al. |
| 5,804,183 A | 9/1998 | Filpula et al. |
| 6,132,713 A | 10/2000 | Fiipula et al. |
| 6,180,387 B1 | 1/2001 | Biswas et al. |
| 6,183,738 B1 | 2/2001 | Clark |
| 6,635,462 B1 | 10/2003 | Ensor et al. |
| 7,204,980 B2 | 4/2007 | Clark |
| 7,323,167 B2 | 1/2008 | Clark |
| 7,413,735 B2 | 8/2008 | Min et al. |
| 9,333,268 B2 | 5/2016 | Bomalaski et al. |
| 9,789,170 B2 | 10/2017 | Showalter et al. |
| 2003/0215429 A1 | 11/2003 | De Simone |
| 2004/0062746 A1 | 4/2004 | Martinez et al. |
| 2004/0258675 A1 | 12/2004 | Ensor et al. |
| 2005/0129706 A1 | 6/2005 | Clark |
| 2006/0002915 A1* | 1/2006 | Min ................ C12Y 305/03006 424/94.5 |
| 2007/0198198 A1 | 8/2007 | Burczynski et al. |
| 2007/0212311 A1 | 9/2007 | Burne et al. |
| 2009/0238813 A1 | 9/2009 | Georgiou et al. |
| 2010/0197944 A1 | 8/2010 | Palle et al. |
| 2010/0303893 A1 | 12/2010 | Luo et al. |
| 2011/0111403 A1 | 5/2011 | Petrauskene et al. |
| 2011/0301189 A1 | 12/2011 | Khattar et al. |
| 2012/0015049 A1 | 1/2012 | Zhang |
| 2012/0148559 A1 | 6/2012 | Georgiou et al. |
| 2013/0052179 A1 | 2/2013 | Huang et al. |
| 2014/0151982 A1 | 6/2014 | Ferret |
| 2014/0348814 A1 | 11/2014 | Almassy et al. |
| 2015/0132278 A1 | 5/2015 | Bomalaski et al. |
| 2015/0231272 A1 | 8/2015 | Bomalaski et al. |
| 2016/0074487 A1 | 3/2016 | Showalter et al. |
| 2017/0000862 A1 | 1/2017 | Wu et al. |

FOREIGN PATENT DOCUMENTS

| | | | |
|---|---|---|---|
| EP | 1987838 B1 | 1/2016 | |
| EP | 2968482 | 7/2016 | |
| JP | 2001-524836 | 12/2001 | |
| JP | 2006-515281 | 5/2006 | |
| JP | 2009-523433 | 6/2009 | |
| KR | 10-2004-0004449 | 1/2004 | |
| WO | 9851784 A1 | 11/1998 | |
| WO | WO 1998/051784 | 11/1998 | |
| WO | 0183774 A2 | 11/2001 | |
| WO | WO2001/083774 | * 11/2001 | ............. C12N 15/55 |
| WO | WO 2001/083774 | 11/2001 | |
| WO | WO 2002/044360 | 6/2002 | |
| WO | WO2004046309 | * 6/2004 | |

(Continued)

OTHER PUBLICATIONS

UniProt Acc#F9UJU2_9MOLU (2011). Alignment with SEQ ID No. 8.*
Bi et al., Isolation and Identification of Mycoplasmas From Pigeons. Chinese J Animal Poultry Infectious Deseases vol. 19, No. 6 1997 p. 1-5.*
Bi et al., Isolation and Identification of Mycoplasmas From Pigeons. Chinese J Animal Poultry Infectious Deseases vol. 19, No. 6 1997 p. 1-5. English Translation.*
USPTO in house BLAST alignment ADI-PEG 20 (the variant of SEQ ID No. 1 herein consisting of the substitutions K112E and P210S) alignment with SEQ ID No. 8. Performed May 10, 2016.*
Poteete et al., Genetic Analysis of Bacteriophage T4 Lysozyme Structure and Function. Journal of Bacteriology, Nov. 1994, p. 6783-6788.*

(Continued)

*Primary Examiner* — Sheridan Swope
(74) *Attorney, Agent, or Firm* — Carter, DeLuca & Farrell LLP

(57) ABSTRACT

The present invention relates generally to isolated to arginine deiminase (ADI) proteins that have reduced cross-reactivity with anti-ADI-PEG 20 antibodies as compared to ADI-PEG 20 (pegylated ADI derived from *M. hominis*), but which can have functional characteristics comparable to or better than ADI-PEG 20, compositions comprising the ADI proteins, and related methods of treating arginine-dependent diseases or related diseases such as cancer.

20 Claims, No Drawings

Specification includes a Sequence Listing.

(56) References Cited

FOREIGN PATENT DOCUMENTS

| WO | 2012143477 A2 | 10/2012 |
| WO | WO 2013/151568 | 10/2013 |
| WO | WO 2014/151982 | 9/2014 |
| WO | WO 2015/143006 A1 | 9/2015 |
| WO | WO 2016/044376 A1 | 3/2016 |

OTHER PUBLICATIONS

Gallego et al., Structural Characterization of the Enzymes Composing the Arginine Deiminase Pathway in Mycoplasma penetrans. PLoS ONE 7 (10), E47886 (2012).*
NCBI Acc#4E4J_A from Gallego et al., 2012. Alignment with SEQ ID No. 8.*
Guo et al., Genome Sequence of Mycoplasma columbinum Strain SF7. Genome Announc. Apr. 18, 2013;1(2):e0015713.*
Wang et al, Engineering an Arginine Catabolizing Bioconjugate: Biochemical and Pharmacological Characterization of PEGylated Derivatives of Arginine Deiminase from Mycoplasma arthritidis. Bioconjugate Chem. 2006, 17, 1447_1459.*
Weickmann et al., Arginine Deiminase from Mycoplasma arthritidis. J Biol Chem vol. 252, No. 8, Issue of April 25, pp. 2615-2620, 1977.*
Zlotogorski, Distribution of skin surface pH on the forehead and cheek of adults. Arch Dermatol Res (1987) 279: 398-401.*
Ni et al., Arginine deiminase, a potential anti-tumor drug. Cancer Letters 261 (2008) 1-11.*
Mycoplasma columbinum Strain SF7 genome translation from Guo et al., Genome Announc. Apr. 18, 2013;1(2):e0015713.*
CAS Registry search "Pegargiminase". performed Aug. 10, 2017.*
NLM search https://chem.nlm.nih.gov/chemidplu&/rn/1394129-74-8 and "ADI-PEG 20" performed Aug. 2017.*
Toxnet search "Pegargiminase". performed Aug. 2017.*
Gong et al., Arginine deiminase inhibits proliferation of human leukemia cells more potently than asparaginase by inducing cell cycle arrest and apoptosis. Leukemia (2000) 14, 826-829.*
Kim et al., Expression, puriWcation, and characterization of arginine deiminase from *Lactococcus lactis* ssp. *lactis* ATCC 7962 in *Escherichia coli* BL21. Protein Expression and Purification 53 (2007) 9-15.*
De Angelis et al., Arginine Catabolism by Sourdough Lactic Acid Bacteria: Purification and Characterization of the Arginine Deiminase Pathway Enzymes from Lactobacillus sanfranciscensis CB1. Applied and Environmental Microbiology, Dec. 2002, p. 6193-6201.*
Scopes, Analysis of Proteins. In: Current Protocols in Molecular Biology (2006) John Wiley & Sons, Inc. pp. 10.0.1-10.0.22.*
Inada et al., Modification of Proteins with Polyethylene Glycol Derivatives. Methods in Enzymology, vol. 242 (1994) p. 65-90.*
Rashotte et al, Daily Cycles in Body Temperature, Metabolic Rate, and Substrate Utilization in Pigeons: Influence of Amount and Timing of Food Consumption. Physiology & Behavior, vol. 57, No. 4, pp. 731-746, 1995.*
Schummer et al., The Proton Gradient Across Mycoplasma Membranes. Current Microbiology, vol. 5 (1981), pp. 371-374.*
Holtsberg et al, Poly(ethylene glycol) (PEG) conjugated arginine deiminase: effects of PEG formulations on its pharmacological properties. Journal of Controlled Release 80 (2002) 259-271.*
UniProt Acc#C4X3Y4, from Ishida et al, 2009.*
Curley et al., Regression of hepatocellular cancer in a patient treated with arginine deiminase. Hepato-gastroenterology, Sep. 1, 2003, 50(53):1214-1216.*
Izzo et al, Pegylated Arginine Deiminase Treatment of Patients With Unresectable Hepatocellular Carcinoma: Results From Phase I/II Studies. J Clin Oncol . May 15, 2004;22(10):1815-22.*
Ascierto, P., et al., "Pegylated Arginine Deiminase Treatment of Patients with Metastitic Melanoma: Results from Phase I and II Studies," Journal of Clinical Oncology, vol. 23, No. 30, Oct. 20, 2005, pp. 7660-7668 and 4047.

Avramis V. et a., "Pharmacokinetic/Pharmacodynamic Relationships of Asparaginase Formulations", Clin Pharmacokinet, (2005), 44(4), pp. 367-393.
Bowles, T., et al., "Pancreatic Cancer Cell Lines Deficient in Argininosuccinate Synthetase are Sensitive to Arginine Deprivation by Arginine Deiminase," Int. J. Cancer: 123, 2008, pp. 1950-1955.
Chen, N., et al., "Autophagy and Tumorigenesis," FEBS Letters 584, 2010, pp. 1427-1435.
Daylami, R., et al., "Abstract 4847: Arginine Deprivation by PEG-ADI Induces Autophagic Cell Death and Enhances the Tumor Suppression Effect of Gemcitabine in Pancreatic Cancer," Cancer Research, Apr. 15, 2010 70; 4847.
Delage, B., et al., "Arginine Deprivation and Argininosuccinate Synthetase Expression in the Treatment of Cancer," International Journal of Cancer, 126, 2010, pp. 2762-2772.
Ensor, C., et al., "Pegylated Arginine Deiminase (ADI-SS PEG20,000 mw) Inhibits Human Melanomas and Hepatocellular Carcinomas in Vitro and in Vivo," Cancer Research, Vo. 62, Oct. 1, 2002, pp. 5443-5450.
Feun, L, et al., "Arginine Deprivation as a Targeted Therapy for Cancer," Current Pharmaceutical Design, 2008, 14, pp. 1049-1057.
Fu C., et al., "PEG-asparaginase", Expert Opinion Pharmacotherapy, (2007), 8, pp. 1977-1984.
Glazer, E., et al., "Phase II Study of Pegylated Arginine Deiminase for Nonresectable and Metastatic Hepatocellular Carcinoma," Journal of Clinical Oncology, vol. 28, No. 13, May 1, 2010, pp. 2220-2226.
Gong, H., et al., "Arginine Deiminase Inhibits Proliferation of Human Leukemia Cells More Potently than Asparaginase by Inducing Cell Cycle Arrest and Apoptosis," Leukemia, vol. 14, 2000, pp. 826-829.
Guven, K., et al., "Cisplatin and Carboplatin Combination as Second-Lind Chemotherapy in Dacarbazine-Resistant Melanoma Patients," Melanoma Research, 11, 2001, pp. 411-415.
He, W., et al., "Abstract 4703: Lack of Expression of Argininosuccinate Synthetase in Human Cancer Tissue: A Biomarker for Sensitivity to Arginine Depetion with Pegylated Arginine Deiminase," Cancer Research, 70, Proceedings: AACR 101st Annual Meeting 2010—Apr. 17-21, 2010, 2 pages.
Hernandez, C., et al., "Pegylated Arginase I: A Potential Therapeutic Approach in T-ALL," Blood, vol. 115, No. 25, Jun. 24, 2010, pp. 5214-5221.
Holtsberg, F., et al., "Poly(ethylene glycol) (PEG) Conjugated Arginine Deiminase: Effects of PEG Formulations on its Pharmacological Properties," Journal of Controlled Release 80, 2002, pp. 259-271.
Izzo F., et al., "Pegylated Arginine Deiminase Treatment of Patients With Unresectable Hepatocellular Carcinoma: Results From Phase I/II Studies", Journal of Clinical Oncology, (2004), vol. 22, No. 10, pp. 1815-1822.
Kelly, M., et al., Abstract 4519: Small Cell Lung Cancers Lack Expression of Argininosuccinate Synthase (ASS) and are sensitive to Arginine Deprivation Using Arginine Deiminase-PEG20 (ADI-PEG20), Cancer Research, 70, AACR 101st Annual Meeting, Apr. 17-21, 2010, 2 pages.
Kelly, MP, et al., "Arginine Deiminase PEG20 Inhibits Growth of Small Cell Lung Cancers Lacking Expression of Argininosuccinate Synthetase," British Journal of Cancer, vol. 106, No. 2, 2012, pp. 324-332.
Kim, R., et al., "ADI, Autophagy and Apoptosis: Metabolic Stress as a Therapeutic Option for Prostate Cancer," Autophagy, vol. 5, No. 4, May 16, 2009, pp. 567-568.
Kim, R., et al., "Arginine Deiminase as a Novel Therapy for Prostate Cancer Induces Autophagy and Caspase-Independent Apoptosis," Cancer Research, vol. 69, No. 2, Jan. 15, 2009, pp. 700-708.
Komada, Y., et al., "Apoptoptic Cell Death of Human T Lymphoblastoid Cells Induced by Arginine Deimanse," International Journal of Hematology, 65, 1997, pp. 129-141.
Kung, C., et al., "Autophagy in Tumor Suppression and Cancer Therapy," Critical Reviews in Eukaryotic Gene Expression, vol. 21, No. 1, 2011, pp. 71-100.
Ni, Y., et al., Arginine Deiminase, a Potential Anti-Tumor Drug, Cancer Letters 261, 2008, pp. 1-11.

(56) References Cited

OTHER PUBLICATIONS

Noh, E., et al., "Arginine Deiminase Enhances Dexamethasone-Induced Cytotoxicity in Human T-Lymphoblastic Leukemia CCRF-CEM Cells," Int. J. Cancer: 112, 204, pp. 502-508.

Ohno, T., et al., "Argininosuccinate Synthetase Gene Expression in Leukemias: Potential Diagnostic Marker for Blastic Crisis of Chronic Myelocytic Leukemia," Leukemia Research, vol. 16, No. 5, 1992, pp. 475-483.

Pinheiro Viera et al., "The best way to use asparaginase in childhood acute lymphatic leukaemia—still to be defined?", British Journal of Haematology, (2004), 125, pp. 117-127.

Savaraj, N., et al., "Arginine Deprivation, Autophagy, Apoptosis (AAA) for the Treatment of Melanoma," Current Molecular Medicine 2010, vol. 10, pp. 405-412.

Shen, L., et al., "Drug Evaluation: ADI-PEG-20—a PEGylated Arginine Deiminase for Arginine-Auxotrophic Cancers," Current Opinon in Molecular Therapeutics, 2006, vol. 8, No. 3, pp. 240-248.

Sugimura, K., et al., "Tumor Growth Inhibitory Activity of a Lymphocyte Blastogenesis Inhibitory Factor," Cancer Research, 50, Jan. 15, 1990, pp. 345-349.

Sugimura, K., et al., "Elevated Argininosuccinate Synthetase Activity in Adult T Leukemia Cell Lines," Leukemia Research, vol. 14, No. 10, 1990, pp. 931-934.

Szlosarek, P., et al., "Abstract 4067: Pegylated Arginine Deiminase (ADI-PEG20) as a Potential Novel Therapy for Argininosuccinate Synthetase-Deficient Acute Myeloid Leukemia," Proceedings of the $102^{nd}$ Annual Meeting of the American Associate for Cancer Research, Apr. 2-6, 2011, vol. 71, No. 8 (Supp), 2 pages.

Szlosarek, P., et al., "In Vivo Loss of Expression of Argininosuccinate Synthetase in Malignant Pleural Mesothelioma is a Biomarker for Susceptibility to Arginine Depletion," Cancer Therapy: Preclinical, Clin Cancer Research, vol. 12, No. 23. Dec. 1, 2006, pp. 7123-7131.

Szlosarek, P., et al., "Effect of Inactivation of Argininosuccinate Synthetase on Sensitivity of Lymphomas to Caspase-Dependent Apoptosis Following Treatment with Arginine Deiminase," Journal of Clinical Oncology, vol. 28. No. 15 (May 20 Supp), 2010, 2 pages.

Yang, T., et al., "A Randomised Phase II Study of Pegylated Arginine Deiminase (ADI-PEG 20) in Asian Advanced Hepatocellular Carcinoma Patients," British Journal of Cancer, vol. 103, 2010, pp. 954-960.

You, M., et al., "Abstract 61: Enhancing Arginine Deprivation Therapy in Melanoma by Combining with Cisplatin," Proceedings of the $101^{st}$ Annual Meeting of the American Association for Cancer Research, Apr. 17-21, 2010, AACR Cancer Research 2010; vol. 70, No. 8 (Supp), 2 pgs.

You, M. et al., "Abstract #3418: Arginine Deprivation and Soluble TRAIL Strikingly Enhance Death in Argininosuccinate Synthetase Negative Melanoma Cells," Proc. Am. Assoc. Cancer Research; Apr. 18-22, 2009, 2 pages.

You, M., et al., "Abstract 4096: TRAIL Enhances Cytotoxicity of Arginine Depletion Therapy in Argininosuccinate Synthetase-Negative Melanoma Cells Through Interruption of Autophagy Via Activation of Caspases," Proceedings of the $102^{nd}$ Annual Meeting of the American Association for Cancer Research; Apr. 2-6, 2011, Cancer Research 2011, vol. 71, No. 8 (Supp), 2 pages.

You, M., et al., "The Combination of ADI-PEG20 and TRAIL Effectively Increases Cell Death in Melanoma Cell Lines," Biochemical and Biophysical Research Communications 394, 2010, pp. 760-766.

Zamora, R., et al. Inducible Nitric Oxide Synthase and Inflammatory Diseases, Molecular Medicine, vol. 6, No. 5, May 2000, pp. 347-360.

Zeidan A et al., "Pegasparaginase: where do we stand?", Expert Opinion Biol Ther, (2009), 9(1), pp. 111-119.

UniProtKB Submission F9UJU2_9MOLU. Arginine deiminase; Mycoplasma columbinum SF7 (Jan. 9, 2013). Retrieved from the Internet Jun. 22, 2014: <http://www.uniprot.org/uniprot/F9UJU2.txt?version=6>); in entirety.

UniProtKB/TrEMBL Submission A7LHN6_9MOLU (Jan. 9, 2013) (Retrieved from the Internet Jun. 22, 2014: <http://www.uniprot.org/uniprot/A7LHN6.txt?version=28>]; in entirety.

International Search Report and Written Opinion for PCT/US12/39979 dated Oct. 22, 2012.

International Search Report for PCT/US2014/026766 dated Oct. 24, 2014.

Supplementary European Search Report for European Application No. 12873622.0, dated Oct. 12, 2015, 11 pages.

Delage, B. et al., "Abstract 4445: Pegylated arginine deiminase induces mitochondrial apoptosis and synergizes with cisplatin in ASS1-negative malignant pleural mesothelioma," In: Proceedings of the 101st Annual Meeting of the American Association for Cancer Research, Apr. 17-21, 2010, Washington, DC, Philadelphia, PA: AACR; Cancer Research, 70(8 Suppl):Abstract nr 4445 (2010), 2 pages.

Feun, L. et al., "Pegylated arginine deiminase: a novel anticancer enzyme agent," Expert Opin. Investig. Drugs., 15(7):815-822 (2006).

Rodriguez, C. O. et al., "Abstract 4848: Pegylated arginine deiminase induces autophagy in canine melanoma and canine osteosarcoma," In: Proceedings of the 101st Annual Meeting of the American Association for Cancer Research, Apr. 17-21, 2010, Washington, DC, Philadelphia, PA: AACR Cancer Research, 70(8 Suppl.):Abstract nr 4848 (2010), 2 pages.

Venugopal, V. et al., "Histidine-dependent activation of arginine deiminase in Clostridium sporogenes: Kinetic evidence on in vivo allosteric interactions," FEBS Letters, 51(1):246-248 (1975).

International Preliminary Report on Patentability for International Application No. PCT/US2012/039979, dated Oct. 7, 2014.

International Preliminary Report on Patentability for International Application No. PCT/US2014/026766, dated Sep. 15, 2015.

Guo et al., "Protein tolerance to random amino acid change", PNAS USA, 101: 9205-6210 (2004).

International Pharmaceutical Excipients Council Japan (ed.), Iyakutenkabutsu Jiten [Pharmaceutical Excipient Dictionary] 2007, Yakuji Nippo Limited, Jul. 25, 2007, p. 220-221.

Ng and Henikoff, "Predicting the Effects of Amino Acid Substitutions on Protein Function", Annu. Rev. Genomics Hum. Genet., 7: 61-80 (2006).

Matthews, B.W., "Structural and genetic analysis of protein stability", Annu. Rev. Biochem., 62:139-160 (1993).

Ott, P.A. et al., "Phase I/II study of pegylated arginine deiminase (ADI-PEG 20) in patients with advanced melanoma", Invest New Drugs, 31(2): 425-434 (2013).

Wang, M. et al., "Engineering an arginine catabolizing bioconjugate: Biochemical and pharmacological characterization of PEGylated derivatives of arginine deiminase from mycoplasma arthritidis," Bioconjugate Chem., 17:1447-1459 (2006).

Baxalta US Inc., Westlake Village, CA, Oncaspar, U.S. Food and Drug Administration Product Label, 8 pages, (Revised 2015).

De Angelis, M., et al., "Arginine Catabolism by Sourdough Lactic Acid Bacteria: Purification and Characterization of the Arginine Deiminase Pathway Enzymes from Lactobacillus sanfranciscensis CB1." Applied and Environmental Microbiology, vol. 68, No. 12, Dec. 2002, pp. 6193-6201.

Kim, J., et al., "Expression, purification, and characterization of arginine deiminase from *Lactococcus lactis* ssp. *lactis* ATCC7962 in *Escherichia coli* BL2I," Protein Expr. Purif. (2007), doi:10.1016/j.pep.2006.12.002, 7 pages.

"IND 119967 for ADI-PEG 20." Food and Drug Administration, Division of Oncology Products 1, Reference ID: 3404331, Nov. 8, 2013, 3 pages.

"IND 120345 for ADI-PEG 20, Arginine Deiminase (recombinant, *E. coli*, Phoenix), PEG-20 Conjugate." Food and Drug Administration, Department of Health and Human Services, Reference ID: 3410107, Date of Submission: Nov. 7, 2013 [Date of Receipt: Nov. 8, 2013], 7 pages.

"Pegargiminase Statement on a Nonproprietary Name Adopted by the USAN Council." Polaris Pharmaceuticals, Inc., Nov. 27, 2013, CAS Registraty No. 1394129-74-8, 2 pages.

Extended European Search Report for European Application No. 14769340.2, dated Jun. 16, 2016, 9 pages.

(56) References Cited

OTHER PUBLICATIONS

Office Action for U.S. Appl. No. 14/214,040, dated Oct. 18, 2016, 19 pages.
Office Action for U.S. Appl. No. 14/855,661, dated Feb. 13, 2017, 15 pages.
International Search Report and Written Opinion for International Application No. PCT/US2015/021189, dated Jun. 25, 2015, 9 pages.
International Preliminary Report on Patentability for International Application No. PCT/US2015/021189, dated Sep. 20, 2016, 6 pages.
International Search Report and Written Opinion for International Application No. PCT/US2015/050354, dated Dec. 18, 2015, 7 pages.
International Preliminary Report on Patentability for International Application No. PCT/US2015/050354, dated Mar. 21, 2017, 6 pages.
Cantor et al., "Therapeutic enzyme deimmunization by combinatorial T-cell epitope removal using neutral drift." Proc Natl Acad Sci USA, Jan. 5, 2011, vol. 108, No. 4, pp. 1272-1277.
Das et al., "Crystal structures of arginine deiminase with covalent reaction intermediates implications for catalytic mechanism." Structure, Apr. 2004, vol. 12, No. 4, pp. 657-667.
Fenske, J.D., and Kenny, George E. "Role of arginine deiminase in growth of Mycoplasma hominis." Journal of bacteriology 126.1 (1976): 501-510.
Henningham et al., "Structure-informed design of an enzymatically inactive vaccine component for group A *Streptococcus*." MBio, Jul./Aug. 2013, vol. 4, No. 4, pii: e00509-13.
Ni et al., "Rapid evolution of arginine deiminase for improved anti-tumor activity," Appl Microbiol Biotechnol., Jan. 11, 2011, vol. 90, No. 1, pp. 193-201.
Singapore Application No. 11201507354Q, Search Report and Written Opinion dated Oct. 10, 2016, 16 pages.
Sugimura et al., "Polymorphism in genes for the enzyme arginine deiminase among Mycoplasma species." Infect. Immun. Jan. 1, 1993, vol. 61, No. 1, pp. 329-331.
De Graaf, et al., "Nonnatural amino acids for site-specific protein conjugation." Bioconjug Chem. (2009); 20(7): 1281-1295.
Doherty, et al., "Site-specific PEGylation of engineered cysteine analogues of recombinant human granulocyte-macrophage colony-stimulating factor." Bioconjug Chem. (2005);16(5): 1291-1298.
Extended European Search Report for European Application No. 15765975.6, dated Oct. 27, 2017, 6 pages.
Feun, et al., "Arginine deprivation in cancer therapy." Curr Opin Clin Nutr Metab Care (2015); 18(1): 78-82.
Park, et al., "Pharmacology of *Escherichia coli*-L-asparaginase polyethylene glycol adduct." Anticancer Res. (1981); 1(6): 373-376.
Phillips, et al., "Targeting arginine-dependent cancers with arginine-degrading enzymes: opportunities and challenges." Cancer Res Treat. (2013); 45(4): 251-262.
Qiu, et al., "Targeting arginine metabolism pathway to treat arginine-dependent cancers." Cancer Lett. (2015); 364(1): 1-7.

Zalipsky and Lee, Polyethylene Glycol Chemistry: Biotechnical and Biomedical Applications, J. M. Harris ed., Plenum Press, NY, Chapter 21, pp. 347-370 (1992).
[Author Unknown] UniProtKB/TrEMBL Submission A5YRS4_9MOLU (Jul. 10, 2007), retrieved from the Internet Jun. 12, 2018, 1 page, http://uniprot.org/uniprot/A5YRS4.txt?version=1.
[Author Unknown] UniProtKB/TrEMBL Submission A7LHN6_9MOLU (Sep. 11, 2007), retrieved from the Internet Jun. 12, 2018, 1 page, http://uniprot.org/uniprot/A7LHN6.txt?version=1.
[Author Unknown] UniProtKB/TrEMBL Submission D4XVN8_9MOLU (Jun. 15, 2010), retrieved from the Internet Jun. 12, 2018, 1 page, http://uniprot.org/uniprot/ D4XVN8.txt?version=1.
[Author Unknown] UniProtKB/TrEMBL Submission F9UJU2_9MOLU (Oct. 19, 2011), retrieved from the Internet Jun. 12, 2018, 1 page, http://uniprot.org/uniprot/ F9UJU2.txt?version=1.
[Author Unknown] GenBank: EGV00288.1, "arginine deiminase [Mycoplasma columbinum SF7]" Aug. 8, 2011, 2 pages, downloaded May 2, 2019 at https://www.ncbi.nlm.nih.gov/protein/343128488.
Extended European Search Report for European Application No. 15842576.9, dated Jun. 18, 2018, 8 pages.
Invitation to Pay Additional Fees for International Application No. PCT/US2014/026766, dated Jul. 21, 2014, 3 pages.
Singapore Application No. 201307953-8, Search Report and Written Opinion dated Jan. 26, 2016, 9 pages.
Ensor et al., "Pegylated arginine deiminase (ADI-SS PEG20,000 mw) inhibits human melanomas and hepatocellular carcinomas in vitro and in vivo", Cancer Research, 62, pp. 5443-5450, Oct. 1, 2002.
Canadian Office Action and Examination Report, dated Mar. 12, 2020, corresponding to counterpart Canadian Application No. 2,901,795; 5 pages.
NCBI GenBank: ABS70985.1, arginine deiminase, partial [Mycoplasma phocicerebrale] (Aug. 4, 2007); 1 page.
NCBI GenBank: ABQ59289.1, arginine deiminase, partial [Mycoplasma gateae] (Jun. 3, 2007); 1 page.
English translation of Korean Office Action dated Sep. 5, 2021, corresponding to counterpart Korean Application No. 10-2021-7016900; 11 pages.
Indian Office Action (with English translation) dated Jan. 22, 2020, corresponding to counterpart Indian Application No. 7802/DELNP/2015; 6 pages.
Canadian Office Action and Examination Report, dated Mar. 15, 2021, corresponding to counterpart Canadian Application No. 2,901,795; 5 pages.
"Submitted name: Arginine deiminase: Mycoplasmopsis columbinum SF7", UniProtKB-F9UJU2 (F9UJU2_9MOLU), Oct. 19, 2011, Retrieved from the internet https://www.uniprot.org/uniprot/F9UJU2.
D'Hooghe et al., "The Arginine Deiminase Pathway in Rhizobium etli: DNA Sequence Analysis and Functional Study of the arcABC Genes," Journal of Bacteriology, Dec. 1997, vol. 179, No. 23; pp. 7403-7409.

* cited by examiner

ARGININE DEIMINASE WITH REDUCED CROSS-REACTIVITY TOWARD ADI - PEG 20 ANTIBODIES FOR CANCER TREATMENT

CROSS-REFERENCE TO RELATED APPLICATIONS

This application claims priority under 35 U.S.C. § 119(e) to U.S. Provisional Application No. 61/790,833, filed Mar. 15, 2013, which is hereby incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is POLA_003_01US_ST25.txt. The text file is about 114 KB, was created on Mar. 14, 2014, and is being submitted electronically via EFS-Web.

BACKGROUND

Technical Field

The present invention relates generally to arginine deiminase (ADI) proteins, including ADI proteins having reduced cross-reactivity with ADI-PEG 20 antibodies. Such ADI proteins are useful for treating arginine-dependent or related diseases such as cancer.

Description of the Related Art

Amino acid deprivation therapy can be an effective treatment of some forms of cancer. To date, there is one known clinical example relevant to this approach which utilizes asparaginase to lower circulating levels of asparagine and inhibit protein synthesis. This treatment is particularly effective for acute lymphoblastic leukemia (Avramis 2005, Viera Pinheiro 2004). Acute lymphoblastic leukemia cells require the amino acid asparagine for growth and proliferation. In contrast, most normal human cells are capable of synthesizing asparagine and are unaffected by asparagine depletion. Therefore, decreasing serum asparagine with asparaginase can selectively kill the cancer cells without harming the normal cells, tissues, and host. An *E. coli* derived form of asparaginase has been approved for human use. However, asparaginase is found only in microbes; which makes it highly immunogenic in humans and also has a short serum half-life following injection (Avramis 2005). To make asparaginase a more effective drug, these drawbacks were minimized by formulating the *E. coli* derived asparaginase with polyethylene glycol (PEG) to reduce the immunogenicity of this enzyme and the associated allergic reactions. In addition, PEG greatly prolongs the circulating half-life of asparaginase, which reduces both the frequency of treatment and the total cost of the therapy. PEG formulated asparaginase is approved for use and is marketed under the trade name Oncaspar® (Oncaspar® 2011, Avramis 2005, Viera Pinheiro 2004, Fu 2007, Zeidan 2008).

Arginine is another non-essential amino acid for humans and mice (for review see Rogers 1994). In humans, arginine can be synthesized from citrulline in two steps via the Krebs (urea) cycle enzymes argininosuccinate synthetase (ASS, L-citrulline:L-aspartate ligase [AMP-forming], EC 6.3.4.5) and argininosuccinate lyase (ASL, L-argininosuccinate arginine-lyase, EC 4.3.2) (Haines 2011, Wu 2009, Morris 2006, Husson 2003, Tapiero 2002, Rogers 1994). ASS catalyzes the conversion of citrulline and aspartic acid to argininosuccinate, which is then converted to arginine and fumaric acid by ASL. An arginine deficient diet in humans does not evoke hyperammonemia, orotic aciduria, nor alter the rate of whole body nitric oxide (NO) synthesis in adult humans (Tapiero 2002, Castillo 1995, Rogers 1994, Carey 1987, Barbul 1986, Snyderman 1959, Rose 1949). Although preterm infants appear to require arginine (Wu 2004), arginine levels do not correlate with age among infants, children and young adults (Lücke 2007). In 1992, Takaku and Sugimura separately reported that human melanomas and hepatocellular carcinoma (HCC) cell lines appear to require arginine for growth. Other studies showed that pegylated ADI was effective for the treatment of melanomas and hepatomas with few adverse effects.

ADI-PEG 20 treatment requires multiple doses over a period of time. After a number of treatments, anti-ADI-PEG 20 antibodies can develop that may limit its continued effectiveness. Therefore, there is a need in the art for ADI that has reduced cross-reactivity to anti-ADI-PEG20 antibodies for use in treatment in order to improve and extend the efficacy of arginine depletion therapy. The present invention provides this and other advantages for the treatment of cancers.

References: Avramis V I, Panosyan E H. 2005. Clin Pharmacokinet 44:367-393; Barbul A. 1986. J Parenteral Enteral Nutr 10:227-238; Carey G P, et al. 1987. J Nutr 117:1734-1739; Castillo L, et al. 1995. Am J Physiol 268 (Endocrinol Metab 31):E360-367; Fu C H, Sakamoto K M. 2007. Expert Opin Pharmacother 8:1977-1984; Haines R J, et al. 2011. Int J Biochem Mol Biol 2:8-23; Husson A, et al. 2003. Eur J Biochem 270:1887-1899; Lücke T, et al. 2007. Clin Chem Lab Med 45:1525-1530; Morris S M Jr. 2006. Am J Clin Nutr 83(Suppl):5985-5125; Rogers Q R. 1994. In Proceedings from a Symposium Honoring Willard J. Visek—from Ammonia to Cancer and Gene Expression. Special Publication 86-April, 1994, Agriculture Experiment Station, University of Illinois, 211 Mumford Hall, Urbana, Ill. 61801, pp. 9-21; Tapiero H, et al. 2002. Biomed Pharmacother 56:439-445, 2002; Viera Pinheiro J P, Boos J. 2004. Br J Haematol 125: 117-127; Wu G, et al. 2009. Amino Acids 37:153-168; Wu G, et al. 2004. J Nutr Biochem 15:442-451; Zeidan A, et al. 2008. Expert Opin Biol Ther 9:111-119).

BRIEF SUMMARY

One aspect of the present invention provides an isolated arginine deiminase, wherein the isolated arginine deiminase has reduced cross-reactivity with patient anti-ADI-PEG 20 antibodies. Also included are therapeutic or pharmaceutical compositions comprising an isolated arginine deiminase or a fragment thereof having ADI activity, and a pharmaceutically-acceptable carrier. In certain embodiments, the composition is sterile and/or substantially free of pyrogens such as endotoxins. In one embodiment, the isolated arginine deiminase having reduced cross-reactivity with patient anti-ADI-PEG 20 antibodies is not from *M. hominis*. In another embodiment, the isolated arginine deiminase having reduced cross-reactivity with patient anti-ADI-PEG 20 antibodies is from an organism listed in Table 1. In certain embodiments the isolated arginine deiminase having reduced cross-reactivity with patient anti-ADI-PEG 20 antibodies has one or more properties comparable to or better than those of ADI-PEG 20. In this regard, the one or more properties includes, but is not limited to, Kcat, Km, pH optimum, stability, in vivo proteolytic stability, or no requirement for ions or cofactors that are not already present in blood, or any combination thereof. In one embodiment, the isolated arginine deiminase having reduced cross-reactivity with patient anti-ADI-PEG 20 antibodies, has at least 20 surface residue changes as compared to *M. hominis* arginine deiminase. In another embodiment, the isolated arginine deiminase having reduced cross-reactivity with patient anti-ADI-PEG 20 antibodies has between 20 and 135 surface residue changes, between 40 and 100 surface residue changes, between 30 and 60 surface residue changes, between 80 and 100 surface residues changes, or between 100 and 120 surface residues changes, as compared to *M. hominis* arginine deiminase.

In another embodiment, the isolated arginine deiminase having reduced cross-reactivity with patient anti-ADI-PEG 20 antibodies is from *M. arginini, M. arthritidis, M. phocicerebrale, M. gateae, M. phocidae, M. columbinum, M. iowae, M. crocodyli, M. alligatoris, H. orenii,* or *M. bovis.* Illustrative arginine deiminase having reduced cross-reactivity with patient anti-ADI-PEG 20 antibodies comprise the amino acid sequence set forth in any one of SEQ ID NOs:2-32.

In another embodiment, the isolated arginine deiminase having reduced cross-reactivity with patient anti-ADI-PEG 20 antibodies has been modified to remove at least one pegylation site. In another embodiment of the arginine deiminase having reduced cross-reactivity with patient anti-ADI-PEG 20 antibodies, at least one lysine residue has been modified by an amino acid substitution. In this regard, in certain embodiments, at least 5 lysine residues, at least 10 lysine residues, or at least 20 lysine residues have been modified by an amino acid substitution.

In another embodiment, the arginine deiminase having reduced cross-reactivity with patient anti-ADI-PEG 20 antibodies is covalently bonded via a linker to a PEG molecule. In this regard, the arginine deiminase having reduced cross-reactivity with patient anti-ADI-PEG 20 antibodies may be covalently bonded to one or more PEG molecule, such as to about 1 to about 10 or about 2 to about 8 PEG molecules. The PEG molecules may be straight chain or branch chain PEG molecules and may have a total weight average molecular weight of from about 1,000 to about 40,000, or a total weight average molecular weight of from about 10,000 to about 30,000. In those embodiments where the PEG is covalently bonded to the ADIr of the present invention, via a linker, the linker may comprise a succinyl group, an amide group, an imide group, a carbamate group, an ester group, an epoxy group, a carboxyl group, a hydroxyl group, a carbohydrate, a tyrosine group, a cysteine group, a histidine group, a methylene group, or any combinations thereof. In one embodiment, the source of the succinyl group is succinimidyl succinate.

Another aspect of the present invention provides a polynucleotide encoding an isolated arginine deiminase described herein, vectors comprising the polynucleotide, and isolated host cells comprising the vectors.

An additional aspect of the present invention provides a composition comprising the isolated arginine deiminase having reduced cross-reactivity with patient anti-ADI-PEG 20 antibodies as described herein and a physiologically acceptable carrier. In certain embodiments, the compositions further comprise a chemotherapeutic agent. Exemplary chemotherapeutic agents include, but are not limited to, docetaxel, carboplatin, cyclophosphamide, gemcitabine, cisplatin, sorafenib, sunitinib, and everolimus.

Another aspect of the present invention provides a method of treating, ameliorating the symptoms of, or inhibiting the progression of a cancer comprising administering to a patient in need thereof a therapeutically effective amount of a composition comprising the isolated arginine deiminase having reduced cross-reactivity with patient anti-ADI-PEG 20 antibodies as described herein and a physiologically acceptable carrier, thereby treating, ameliorating the symptoms of, or inhibiting the progression of the cancer. In certain embodiments, the patient in need thereof has been determined to have anti-ADI-PEG 20 antibodies. In another embodiment, the cancer is selected from the group consisting of hepatocellular carcinoma, melanoma including metastatic melanoma, pancreatic cancer, prostate cancer, small cell lung cancer, mesothelioma, lymphocytic leukemia, chronic myelogenous leukemia, lymphoma, hepatoma, sarcoma, leukemia, acute myeloid leukemia, relapsed acute myeloid leukemia, breast cancer, ovarian cancer, colorectal cancer, gastric cancer, glioma, glioblastoma multiforme, non-small cell lung cancer (NSCLC), kidney cancer, bladder cancer, uterine cancer, esophageal cancer, brain cancer, head and neck cancers, cervical cancer, testicular cancer, and stomach cancer.

Another aspect of the invention provides a method of treating, ameliorating the symptoms of, or inhibiting the progression of a cancer comprising administering to a patient in need thereof a therapeutically effective amount of a composition comprising ADI-PEG 20, and after a period of time, administering to the patient a composition comprising the isolated arginine deiminase having reduced cross-reactivity with patient anti-ADI-PEG 20 antibodies as described herein and a physiologically acceptable carrier, thereby treating, ameliorating the symptoms of, or inhibiting the progression of the cancer. In this regard, the period of time may be determined, for example, by detecting a predetermined level of anti-ADI-PEG 20 antibodies in the patient and/or measuring or otherwise observing ADI activity in the patient, wherein the composition comprising the isolated arginine deiminase having reduced cross-reactivity with patient anti-ADI-PEG 20 antibodies is administered following detection of the predetermined level of said anti-ADI-PEG 20 antibodies and/or measurement or observation of a predetermined level of ADI activity in the patient.

Also included are isolated arginine deiminase proteins described herein for use in the preparation or manufacture of a medicament for treating, ameliorating the symptoms of, or inhibiting the progression of a cancer.

DETAILED DESCRIPTION

Embodiments of the present invention relate to selected ADI enzymes, which in some embodiments are engineered to have a small number of surface lysine residues, and conjugated with PEG through a stable linker. The selected ADI enzymes are chosen from a large number of ADI enzymes, from different organisms, based on their beneficial properties. These properties include the ability of the enzyme to establish and maintain low arginine concentrations in human blood through ADI conversion of arginine to citrulline and ammonia. In addition, the selected ADI molecules have reduced cross-reactivity toward anti-ADI-PEG 20 antibodies as compared to ADI-PEG 20, such antibodies possibly resulting from a patient's previous treatment with ADI-PEG 20.

In certain embodiments, the enzymes in this invention are pegylated to provide protection against renal clearance and proteolysis, as well as reduced immunogenicity or antigenicity. To increase the effectiveness of the pegylation, modifications to the enzymes may be engineered to reduce the number of surface lysine residues and therefore limit the number of available PEG attachment sites. This provides more complete and uniform pegylation at the remaining lysine attachment residues.

The PEG linker selected to attach methoxy-PEG to ADI is chosen to provide a chemically stable linkage. It is expected this will increase the molecule's bioactive lifetime. A chemically stable linker will also eliminate hydrolysis and reduce an immune response that might occur to a de-pegylated linker attached to the enzyme surface.

These cumulative specifications result in one or more molecules that effectively remove arginine from a patient's blood and are not neutralized or cleared by anti-ADI-PEG 20 antibodies from previous arginine depletion therapy. The molecules are pegylated so as to delay neutralization and clearance due to their own immunogenicity. These factors will permit their use instead of ADI-PEG 20 or in addition to ADI-PEG 20 (e.g., as a follow-on drug) to extend arginine depletion therapy and therefore increase effectiveness of arginine depletion treatment as an anti-cancer therapeutic.

Normal cells do not require arginine for growth, since they can synthesize arginine from citrulline in a two step process catalyzed by ASS and ASL. In contrast, certain cancers do not express ASS. Certain cancers do not express ASL, and other cancers may have diminished expression of, or may not express ASS and/or ASL. Therefore, these cancers are auxotrophic for arginine. This metabolic difference may be capitalized upon to develop a safe and effective therapy to treat these forms of cancer. ADI catalyzes the conversion of arginine to citrulline via the arginine dihydrolase pathway, and may thus be used to eliminate arginine.

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., *Current Protocols in Protein Science, Current Protocols in Molecular Biology* or *Current Protocols in Immunology*, John Wiley & Sons, New York, N.Y. (2009); Ausubel et al., *Short Protocols in Molecular Biology*, 3$^{rd}$ ed., Wiley & Sons, 1995; Sambrook and Russell, *Molecular Cloning: A Laboratory Manual* (3rd Edition, 2001); Maniatis et al. *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984) and other like references.

As used in this specification and the appended claims, the singular forms "a," "an" and "the" include plural references unless the content clearly dictates otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

By "statistically significant," it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

Each embodiment in this specification is to be applied mutatis mutandis to every other embodiment unless expressly stated otherwise.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well known and commonly used in the art. Standard techniques may be used for recombinant technology, molecular biological, microbiological, chemical syntheses, chemical analyses, pharmaceutical preparation, formulation, and delivery, and treatment of patients.

"Patient" or "subject" refers to an animal, in certain embodiments a mammal, and in a specific embodiment, a human.

"Biocompatible" refers to materials or compounds which are generally not injurious to biological functions and which will not result in any degree of unacceptable toxicity, including allergenic and disease states.

The term "reference sequence" refers generally to a nucleic acid coding sequence, or amino acid sequence, to which another sequence is being compared. All polypeptide and polynucleotide sequences described herein are included as references sequences, including those described by name and those described in the Tables and the Sequence Listing.

Throughout the present disclosure, the following abbreviations may be used: PEG, polyethylene glycol; ADI, arginine deiminase; SS, succinimidyl succinate; SSA, succinimidyl succinimide; SPA, succinimidyl propionate; NHS, N-hydroxy-succinimide; ASS1 or ASS, argininosuccinate synthetase; ASL, argininosuccinate lyase.

In the present invention, a polynucleotide encoding ADI may be derived, cloned, isolated, synthesized or produced from any source, including, for example, microorganisms, recombinant biotechnology or any combination thereof. For example, arginine deiminase may be cloned from microorganisms of the genera *Mycoplasma, Clostridium, Bacillus, Borrelia, Enterococcus, Streptococcus, Lactobacillus,* and/or *Giardia*. In certain embodiments, arginine deiminase is cloned from *Mycoplasma arthritidis, Mycoplasma pneumoniae, Mycoplasma hominis, Mycoplasma arginini, Steptococcus pyogenes, Steptococcus pneumoniae, Borrelia burgdorferi, Borrelia afzelii, Giardia intestinalis, Clostridium perfringens, Bacillus licheniformis, Enterococcus faecalis, Lactobacillus sake*, or any combination thereof. In other embodiments, the arginine deiminase is cloned from a species listed in Table 1. In particular, the ADI used in the present invention may comprise the amino acid sequence of any one of SEQ ID NOs: 1-32, or a variant or fragment or extension thereof having ADI activity (e.g., able to metabolize arginine into citrulline and ammonia). Some of the sequences provided in the sequence listing do not represent full-length ADI protein sequences. Thus, in certain embodiments, additional amino acid residues can be added to either end of the sequences provided herein to make a full-length protein having ADI activity. The specific amino acids to be added can be determined by the skilled person based on alignments of known ADI sequences. Such ADI molecules can be synthesized using known techniques. Illustrative "extended" ADI(r) are provided, for example, in SEQ ID NOs:26-32.

In certain embodiments, the ADI enzymes as described herein are compared to the benchmark ADI-PEG 20 molecule derived from *M. hominis*. As used herein, "ADI-PEG 20" refers to the ADI molecule known in the art and described for example in U.S. Pat. Nos. 6,183,738; 6,635,462; Ascierto P A, et al. (2005) Pegylated arginine deiminase treatment of patients with metastatic melanoma: results from phase I and II studies. J Clin Oncol 23(30): 7660-7668; Izzo F, et al. (2004) Pegylated arginine deiminase treatment of patients with unresectable hepatocellular carcinoma: results from phase I/II studies. J Clin Oncol 22(10): 1815-1822; Holtsberg F W, et al. (2002), Poly(ethylene glycol) (PEG) conjugated arginine deiminase: effects of PEG formulations on its pharmacological properties. J Control Release 80(1-3): 259-271; Kelly et al., (2012) British Journal of Cancer 106, 324-332. As would be recognized by the skilled artisan, this molecule is a pegylated (PEG 20,000) ADI enzyme derived from *M. hominis*, and has two substitutions (K112E; P210S) relative to the wild type *M. hominis* ADI enzyme.

The arginine deiminase enzymes as described herein were screened from a large number of ADI enzymes and have a reduced level of reactivity with anti-ADI-PEG 20 antibodies from patients. Anti-ADI-PEG 20 antibodies can appear in subjects treated with ADI-PEG 20 and can be measured using known methodologies. Reactivity to anti-ADI-PEG 20 antibodies can be determined for example using ELISA or other similar assays known to the skilled artisan.

In this regard, ADI-PEG 20 can be used as a comparison to assess cross-reactivity level to patient anti-ADI-PEG 20 antibodies. A cross-reactivity level that is statistically significantly lower than that of ADI-PEG 20 to patient anti-ADI-PEG 20 antibodies may be useful herein. In certain embodiments, the arginine deiminase enzymes as described herein have low or no cross-reactivity to anti-ADI-PEG 20 antibodies. In another embodiment, any reduction in reactivity to anti-ADI-PEG 20 antibodies as compared to reactivity with ADI-PEG 20 can be beneficial as such an ADI enzyme would improve treatment options for patients in need of arginine depletion therapy. Thus, the arginine deiminase enzymes as described herein have reduced cross-reactivity to patient anti-ADI-PEG 20 antibodies as compared to ADI-PEG 20 reactivity to such antibodies.

"ADIr" is used herein to refer to an ADI enzyme of the present invention having reduced cross-reactivity to anti-ADI-PEG 20 antibodies as compared to ADI-PEG 20 reactivity to such antibodies. "ADIr" nomenclature is used to distinguish the molecules identified herein from ADI and ADI-PEG 20 as known in the art.

The ADIr enzymes of the invention have characteristics or properties comparable to or better than those of ADI-PEG 20, in order to reduce and maintain low blood arginine levels for effective cancer treatment. Such properties include Kcat, Km, pH optimum, stability, in vivo proteolytic stability and lack of requirement for ions or cofactors not already present in the blood, or any combination thereof. In certain embodiments, an ADIr as described herein has properties that are about or at least 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or higher, than comparable properties of ADI-PEG 20. In other embodiments an ADIr described herein has properties that are about or at least about 100%, 105%, 110%, 120%, 140%, 150%, 160%, 180%, 200%, 220%, 240%, 250%, 260%, 280%, 300%, 320%, 340, 350%, 360%, 400%, 420%, 450%, 460%, 500%, 520%, 550% or higher than the specific property of ADI-PEG 20 being compared.

Thus, in certain embodiments, an ADIr has a Kcat that is about or at least about 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% of the Kcat of ADI-PEG 20, or better. In certain embodiments, an ADIr has a Kcat that is about or at least about 100%, 105%, 110%, 120%, 125%, 140%, 150%, 160%, 180%, 200%, 220%, 240%, 250%, 260%, 280%, 300%, 320%, 340, 350%, 360%, 400%, 420%, 450%, 460%, 500%, 520%, 550% or higher, times that of the ADI-PEG 20 Kcat. In certain embodiments, the Kcat of the ADIr enzymes described herein, or compositions comprising same, is about 0.5 $sec^{-1}$ to about 15 $sec^{-1}$, and in a further embodiment, is from about 1 $sec^{-1}$ to about 12 $sec^{-1}$, about 1 $sec^{-1}$ to about 10 $sec^{-1}$, about 1.5 $sec^{-1}$ to about 9 $sec^{-1}$, about 2 $sec^{-1}$ to about 8 $sec^{-1}$ or about 2.5 $sec^{-1}$ to about 7 $sec^{-1}$. In certain embodiments, the ADIr or ADIr-PEG in a composition has a Kcat of about 2.5 $sec^{-1}$ to about 7.5 $sec^{-1}$. In some embodiments, the ADIr or ADIr-PEG in a composition has a Kcat of about 2.5 $sec^{-1}$, about 3 $sec^{-1}$, about 3.5 $sec^{-1}$, about 4 $sec^{-1}$, about 4.5 $sec^{-1}$, about 5 $sec^{-1}$, about 5.5 $sec^{-1}$, about 6 $sec^{-1}$, about 6.5 $sec^{-1}$, about 7 $sec^{-1}$, about 7.2 $sec^{-1}$, about 7.5 $sec^{-1}$, about 8 $sec^{-1}$, about 10 $sec^{-1}$, about 15 $sec^{-1}$, about 20 $sec^{-1}$, about 25 $sec^{-1}$, about 30 $sec^{-1}$, about 35 $sec^{-1}$, about 40 $sec^{-1}$, about 45 $sec^{-1}$, about 50 $sec^{-1}$, about 55 $sec^{-1}$, about 60 $sec^{-1}$, about 65 $sec^{-1}$, about 70 $sec^{-1}$, about 75 $sec^{-1}$, about 80 $sec^{-1}$, about 85 $sec^{-1}$, about 90 $sec^{-1}$, about 95 $sec^{-1}$, or about 100 $sec^{-1}$.

Thus, in certain embodiments, an ADIr has a Km that is about or at least about 5%, 6%, 7%, 8%, 9%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% of the Km of ADI-PEG 20, or better. Thus, in certain embodiments, an ADIr has a Km that is about or at least about 100%, 105%, 110%, 120%, 130%, 140%, 150%, 160%, 180%, 200%, 220%, 240%, or 250% that of the Km of ADI-PEG 20. In one embodiment, an ADIr, or a pegylated formulation thereof, has a Km of from about 0.5 μM to about 50 μM, or about 1.6 μM to about 48 μM, or about 0.5 μM to about 15 μM, and in a further embodiment, is from about 1 μM to about 12 μM, about 1 μM to about 10 μM, about 1.5 μM to about 9 μM, about 1.5 μM to about 8 μM or about 1.5 μM to about 7 μM. In certain embodiments, the ADIr or ADIr-PEG in a composition has a Km of about 1.5 μM to about 6.5 μM. In some embodiments, the ADIr or pegylated formulation thereof has a Km of about 1.5 μM, about 1.6 μM, about 2 μM, about 2.5 μM, about 3 μM, about 3.5 μM, about 4 μM, about 4.5 μM, about 5 μM, about 5.5 μM, about 6 μM, about 6.5 μM, about 7 μM, about 8 μM, about 9 μM, about 10 μM, about 12 μM, about 14 μM, about 15 μM, about 16 μM, about 18 μM about 20 μM, about 22 μM, about 24 μM, about 25 μM, about 26 μM, about 28 μM, about 30 μM, about 32 μM, about 34 μM, about 35 μM, about 36 μM, about 38 µM, about 40 µM, about 42 µM, about 44 µM, about 45 µM, about 46 µM, about 48 µM, or about 50 µM.

In certain embodiments, an ADIr functions at a pH close to the physiological pH of human blood. Thus, in one embodiment, an ADIr functions at a pH of about 4 to about 10.8, or about 6 to about 8, or about 6.5 to about 7.5. In one embodiment, an ADIr has good enzyme activity at about pH 7.4.

In certain embodiments, an ADIr has stability during long term storage and temperature and proteolytic stability during treatment in the human body. In further embodiments, an ADIr does not require ions or cofactors for activity that are not already present in blood.

In certain embodiments, an ADIr described herein generally has an amino acid sequence sufficiently different from *M. hominis* so that there are surface residue changes which will reduce or eliminate antigenic sites for anti-ADI-PEG 20 antibodies. In one embodiment, there will be no cross reactivity between the selected ADIr molecule and existing anti-ADI-PEG 20 antibodies in a subject, and a completely new immune response will be generated in a subject rather than a maturation of the existing response to *M. hominis* ADI. Thus, in one embodiment, an ADIr as described herein has from 20%-85% sequence identity to *M. hominis* ADI as set forth in SEQ ID NO:1. In certain embodiments, an ADIr as described herein has even lower percent sequence identity to *M. hominis* ADI, such as 10% or 15% identity. In another embodiment, an ADIr as described herein has 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82% or even 83% identity to *M. hominis* ADI, and still has reduced cross-reactivity toward anti-ADI-PEG 20 antibodies.

In one embodiment, an ADIr as described herein has from about 25-140 surface residue changes as compared to *M. hominis* ADI. Surface residues can be identified from the crystal structure of *M. hominis* ADI and surface residues for ADI from other organisms can be determined by sequence homology. An ADIr as described herein may have about 25, 30, 35, 40, 45, 50, 55, 60, 65, 70, 75, 80, 85, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, or about 140 surface residue changes as compared to *M. hominis* ADI (see SEQ ID NO:1).

In another embodiment, an ADIr as described herein has from about 25-140 residue changes as compared to *M. hominis* ADI. Such residue changes need not only be of surface amino acid residues. Such residue changes (or additions or deletions) can be at either end of the molecule or may be at any residue of the ADI, such that the modified ADI has the desired ADI activity as described herein. Residues to be changed can be identified from the crystal structure of *M. hominis* ADI and residues for ADI from other organisms can be determined by sequence homology. An ADIr as described herein may have about 25, 30, 35, 40, 45, 50, 55, 60, 65, 70, 75, 80, 85, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, or about 140 amino acid residue changes as compared to *M. hominis* ADI (see SEQ ID NO:1).

From a large number of ADI enzymes, Table 1 lists 24 ADIr enzymes with their sequence percent identity relative to *M. hominis* ADI. From the literature, *M. hominis*, *M. arginini*, and *M. arthritidis* ADI amino acid sequences are closely related and these enzymes have good catalytic properties. More recently, additional ADI enzymes have been discovered that have sequences closely related to these three. More distantly related *Mycoplasma* ADI enzymes have been identified, although less is known about them. And even more distantly related ADI enzymes from bacterial and other sources exist.

In certain embodiments, the ADIr enzymes identified herein from a number of selected species, have surface lysine residues (in certain embodiments, up to 30 or more). However, in certain embodiments an ADIr enzyme may have many fewer surface lysine residues, such as just 2 lysine residues as in the case of *Mycobacterium bovis* ADI, or even no lysine residues (see e.g., ADI from *Mycobacterium* sp. MCS; GenBank No. ABG10381). Therefore, the ADIr enzymes identified herein that have reduced cross-reactivity with anti-ADI-PEG 20 antibodies, have about 0, 1, 2, 3, 4, 5, 10, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, or more surface lysine residues.

The terms "polypeptide," "protein" and "peptide" are used interchangeably and mean a polymer of amino acids not limited to any particular length. The terms do not exclude modifications such as myristoylation, sulfation, glycosylation, phosphorylation and addition or deletion of signal sequences. The terms "polypeptide" or "protein" means one or more chains of amino acids, wherein each chain comprises amino acids covalently linked by peptide bonds, and wherein said polypeptide or protein can comprise a plurality of chains non-covalently and/or covalently linked together by peptide bonds, having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. The terms "polypeptide" and "protein" specifically encompass the ADIr proteins of the present disclosure, or sequences that have deletions from, additions to, and/or substitutions of one or more amino acid of the ADIr proteins. In certain embodiments, the polypeptide is a "recombinant" polypeptide, produced by recombinant cell that comprises one or more recombinant DNA molecules, which are typically made of of heterologous polynucleotide sequences or combinations of polynucleotide sequences that would not otherwise be found in the cell.

The term "isolated protein" referred to herein means that a subject protein (1) is free of at least some other proteins with which it would typically be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein with which the "isolated protein" is associated in nature, (6) is operably associated (by covalent or noncovalent interaction) with a polypeptide with which it is not associated in nature, or (7) does not occur in nature. Such an isolated protein can be encoded by genomic DNA, cDNA, mRNA or other RNA, of may be of synthetic origin, or any combination thereof. In certain embodiments, the isolated protein is substantially free from proteins or polypeptides or other contaminants that are found in its natural environment that would interfere with its use (therapeutic, diagnostic, prophylactic, research or otherwise).

The term "variant" includes a polypeptide that differs from a reference polypeptide specifically disclosed herein (e.g., SEQ ID NOS:1-32) by one or more substitutions, deletions, additions and/or insertions. Variant polypeptides are biologically active, that is, they continue to possess the enzymatic or binding activity of a reference polypeptide. Such variants may result from, for example, genetic polymorphism and/or from human manipulation.

In many instances, a biologically active variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present invention and still obtain a functional molecule that encodes a variant or derivative polypeptide with desirable characteristics.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their utility.

In making such changes, the hydropathic index of amino acids may be considered. The importance of the hydropathic amino acid index in conferring interactive biologic function on a protein is generally understood in the art (Kyte & Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte & Doolittle, 1982). These values are: isoleucine (+4.5); valine (+4.2); leucine (+3.8); phenylalanine (+2.8); cysteine (+2.5); methionine (+1.9); alanine (+1.8); glycine (-0.4); threonine (-0.7); serine (-0.8); tryptophan (-0.9); tyrosine (-1.3); proline (-1.6); histidine (-3.2); glutamate (-3.5); glutamine (-3.5); aspartate (-3.5); asparagine (-3.5); lysine (-3.9); and arginine (-4.5). It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (-0.4); proline (-0.5±1); alanine (-0.5); histidine (-0.5); cysteine (-1.0); methionine (-1.3); valine (-1.5); leucine (-1.8); isoleucine (-1.8); tyrosine (-2.3); phenylalanine (-2.5); tryptophan (-3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

A variant may also, or alternatively, contain non-conservative changes. In a preferred embodiment, variant polypeptides differ from a native sequence by substitution, deletion or addition of fewer than about 10, 9, 8, 7, 6, 5, 4, 3, 2 amino acids, or even 1 amino acid. Variants may also (or alternatively) be modified by, for example, the deletion or addition of amino acids that have minimal influence on the immunogenicity, secondary structure, enzymatic activity, and/or hydropathic nature of the polypeptide.

In general, variants will display about or at least about 30%, 40%, 50%, 55%, 60%, 65%, 70%, 75%, 80%, 85%, 90%, 91%, 92%, 93%, 94%, 95%, 96%, 97%, 98%, 99% similarity or sequence identity or sequence homology to a reference polypeptide sequence (e.g., SEQ ID NOS:1-32). Moreover, sequences differing from the native or parent sequences by the addition (e.g., C-terminal addition, N-terminal addition, both), deletion, truncation, insertion, or substitution of about 1, 2, 3, 4, 5, 6, 7, 8, 9, 10, 11, 12, 13, 14, 15, 16, 17, 18, 19, 20, 30, 40, 50, 60, 70, 80, 90, 100 or more amino acids but which retain the properties or activities of a parent or reference polypeptide sequence are contemplated.

In some embodiments, variant polypeptides differ from reference sequence by at least one but by less than 50, 40, 30, 20, 15, 10, 8, 6, 5, 4, 3 or 2 amino acid residue(s). In other embodiments, variant polypeptides differ from a reference sequence by about or at least 0.5% or 1% but less than 20%, 15%, 10% or 5% of the residues. (If this comparison requires alignment, the sequences should be aligned for maximum similarity. "Looped" out sequences from deletions or insertions, or mismatches, are considered differences.).

The term "polypeptide fragment" refers to a polypeptide that has an amino-terminal deletion, a carboxyl-terminal deletion, and/or an internal deletion or substitution of a naturally-occurring or recombinantly-produced polypeptide. In certain embodiments, a polypeptide fragment can comprise an amino acid chain at least 5 to about 400 amino acids long. It will be appreciated that in certain embodiments, fragments are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, or 400 amino acids long. Particularly useful polypeptide fragments include functional domains, including the catalytic ADI domains of the ADIr described herein. In the case of an ADIr, useful fragments include, but are not limited to, the catalytic domain and the α-helical domain.

Many activated PEGs used for conjugation to ADI covalently bond to lysine residues. There are usually many fewer PEG molecules attached to ADI than there are lysine residues. Both the number and distribution of attachments can be heterogeneous from molecule to molecule. Any particular lysine residue will be modified in only a small fraction of the ADI molecules. This site modification heterogeneity and low PEG occupancy can result in problems with both drug characterization and the effectiveness of PEG shielding at antigenic sites. Therefore, in certain embodiments, the selected ADIr enzymes as described herein, are modified by lysine replacement with other residue types to reduce the number of lysine residues. This produces a more uniformly pegylated protein and increases the PEG occupancy at the remaining lysine residues. Specific lysine residues chosen to be changed to other residues will be selected in order to preserve enzyme activity. This more uniform pegylation is expected to provide increased protection against proteolysis in blood and increased shielding of antigenic sites from patient antibodies.

In certain embodiments, the ADIr of the present disclosure may be modified as described in U.S. Pat. No. 6,635,462. In particular, modifications of one or more of the naturally occurring amino acid residues of an ADIr can provide for an enzyme that is more easily renatured and formulated thereby improving the manufacture of ADIr and therapeutic compositions comprising the same. In one embodiment, the ADIr of the present disclosure is modified to remove one or more lysine residues (e.g., the lysine can be substituted with another amino acid or analogues thereof, or a non-natural amino acid). In particular, in one embodiment, the ADIr is modified to be free of the lysine at a position equivalent to 112, 374, 405 or 408 of SEQ ID NO:1 (*M. hominis* ADI), or a combination of one or more of these positions. In a further embodiment, the ADIr is modified to be free of one or more lysines, for example, 1, 2, 3, 4, 5, 6, 7, 8, 9, 10, 11, 12, 13, 14, 15, 16, 17, 18, 19, 20, 21, or more lysine residues, should they be present, can be substituted with another amino acid or analogues thereof, or a nonnatural amino acid. In one embodiment, an ADIr has 5 lysines substituted, for example, at an equivalent position to position 7, 88, 137, 209, and 380 of SEQ ID NO: 1. In another embodiment, an ADIr has 10 lysines substituted, for example, at positions equivalent to positions 7, 9, 59, 88, 115, 116, 137, 178, 209, and 380 of SEQ ID NO: 1. In yet another embodiment, an ADIr has 15 lysines substituted, for example, at positions equivalent to positions 7, 9, 59, 66, 88, 91, 93, 115, 116, 137, 141, 178, 209, 279, and at position 380 of SEQ ID NO: 1. In one embodiment, an ADIr comprises 21 lysines substituted, for example, at positions equivalent to positions 7, 9, 56, 59, 66, 88, 91, 93, 96, 115, 116, 137, 141, 178, 209, 254, 279, 325, 326, 380, and 406 of SEQ ID NO: 1.

A native ADIr may be found in microorganisms and is immunogenic and rapidly cleared from circulation in a patient. These problems may be overcome by modifying an ADIr. Thus, the present disclosure provides ADIr modified by a modifying agent, including, but not limited to macromolecule polymers, proteins, peptides, polysaccharides, or other compounds. Arginine deiminase as described herein and the modifying agent may be linked by either covalent bonds or non-covalent interaction to form a stable conjugate or a stable composition to achieve a desired effect. In certain embodiments, the modified ADIr retains the biological activity of an unmodified ADIr and has a longer half life in vivo and lower antigenicity than the unmodified, ADIr. In certain embodiments, the modified ADIr retains at least 30%, 35%, 40%, 45%, 50%, 55%, 60%, 65%, 70%, 75%, 80%, 85%, 90%, 95%, 96%, 97%, 98%, 99% or more of the biological activity of unmodified ADIr. Generally, the modified ADIr retains biological activity sufficient for therapeutic use.

In one embodiment, a modifying agent can be a polymer or a protein or a fragment thereof that is biocompatible and can increase the half life of ADIr in blood. The modifying agent can be either chemically coupled to ADIr or where applicable, linked to the ADIr via fusion protein expression.

Macromolecule polymers may include a non-peptide macromolecule polymer, which in certain embodiments, may have its own bioactivity. Suitable polymers include, but are not limited to, polyenol compounds, polyether compounds, polyvinylpyrrolidone, poly amino acids, copolymer of divinyl ether and maleic anhydride, N-(2-hydroxypropyl)-methacrylamide, polysaccharide, polyoxyethylated polyol, heparin or its fragment, poly-alkyl-ethylene glycol and its derivatives, copolymers of poly-alkyl-ethylene glycol and its derivatives, poly(vinyl ethyl ether), a,P-Poly[(2-hydroxyethyl)-DL-aspartamide], polycarboxylates, poly oxyethylene-oxymethylenes, polyacryloyl morpholines, copolymer of amino compounds and oxyolefin, poly hyaluronic acid, polyoxiranes, copolymer of ethanedioic acid and malonic acid, poly(1,3-dioxolane), ethylene and maleic hydrazide copolymer, poly sialic acid, cyclodextrin, etc. In certain embodiments, the polymer is polyethylene glycol.

The polyenol compounds as used herein include, but are not limited to, polyethylene glycol (including monomethoxy polyethylene glycol, monohydroxyl polyethylene glycol), polyvinyl alcohol, polyallyl alcohol, polybutenol and the like, and their derivatives, such as lipids.

The polyether compounds include, but are not limited to poly alkylene glycol $(HO((CH2)_xO)_nH)$, polypropylene glycol, polyoxyrehylene $(HO((CH_2)_2O)_nH)$, polyvinyl alcohol $((CH_2CHOH)_n)$.

Poly amino acids include, but are not limited to, polymers of one type of amino acid or copolymers of two or more types of amino acids, for example, polyalanine or polylysine, or block co-polymers thereof.

Polysaccharides include but are not limited to, glucosan and its derivatives, for example dextran sulfate, cellulose and its derivatives (including methyl cellulose and carboxymethyl cellulose), starch and its derivatives, polysucrose, etc.

In one specific embodiment of the present invention, ADIr is modified by coupling with proteins or peptides, wherein one or more proteins or peptides are directly or indirectly linked to ADIr. The proteins can either be naturally existing proteins or their fragments, including but not limited to naturally existing human serum proteins or their fragments, such as thyroxine-binding protein, transthyretin, a1-acid glycoprotein, transferrin, fibrinogen, immunoglobulin, Ig Fc regions, albumin, and fragments thereof. By "fragment" is meant any portion of a protein that is smaller than the whole protein but which retains the desired function of the protein. The ADIr as described herein may be directly or indirectly linked to a protein via a covalent bond. Direct linking means that one amino acid of ADIr is directly linked to one amino acid of the modifying protein, via a peptide bond or a disulfide bridge. Indirect linking refers to the linkages between a ADIr and a modifying protein, via originally existing chemical groups therebetween or specific chemical groups added through biological or chemical means, or the combination of the above-mentioned linkages.

In one particular embodiment, ADIr is modified by covalent attachment with PEG. ADIr covalently modified with PEG (with or without a linker) may be hereinafter referred to as "ADIr-PEG." When compared to unmodified ADIr, ADIr-PEG retains most of its enzymatic activity, is far less immunogenic or antigenic, has a greatly extended circulating half-life, and is much more efficacious in the treatment of tumors.

"Polyethylene glycol" or "PEG" refers to mixtures of condensation polymers of ethylene oxide and water, in a branched or straight chain, represented by the general formula $H(OCH_2CH_2)nOH$, wherein n is at least 4. "Polyethylene glycol" or "PEG" is used in combination with a numeric suffix to indicate the approximate weight average molecular weight thereof. For example, PEG5,000 refers to PEG having a total weight average molecular weight of about 5,000; PEG12,000 refers to PEG having a total weight average molecular weight of about 12,000; and PEG20,000 refers to PEG having a total weight average molecular weight of about 20,000.

In one embodiment of the present invention, the PEG has a total weight average molecular weight of about 1,000 to about 50,000; in one embodiment from about 3,000 to about 40,000, and in another embodiment from about 5,000 to about 30,000; in certain embodiments from about 8,000 to about 30,000; in other embodiments from about 11,000 to about 30,000; in additional embodiments, from about 12,000 to about 28,000; in still other embodiments, from about 16,000 to about 24,000; and in other embodiments, about 18,000 to about 22,000; in another embodiment, from 19,000 to about 21,000, and in one embodiment, the PEG has a total weight average molecular weight of about 20,000. Generally, PEG with a molecular weight of 30,000 or more is difficult to dissolve, and yields of the formulated product may be reduced. The PEG may be a branched or straight chain. Generally, increasing the molecular weight of the PEG decreases the immunogenicity of the ADIr. The PEG having a molecular weight described in this embodiment may be used in conjunction with ADIr, and, optionally, a biocompatible linker, to treat cancer, including, for example, acute myeloid leukemia, such as relapsed acute myeloid leukemia, breast cancer, ovarian cancer, colorectal cancer, gastric cancer, glioma, glioblastoma multiforme, non-small cell lung cancer (NSCLC), kidney cancer, bladder cancer, uterine cancer, esophageal cancer, brain cancer, head and neck cancers, cervical cancer, testicular cancer, stomach cancer and esophageal cancer.

In another embodiment of the present invention, the PEG has a total weight average molecular weight of about 1,000 to about 50,000; in certain embodiments about 3,000 to about 30,000; in other embodiments from about 3,000 to about 20,000; in one embodiment from about 4,000 to about 12,000; in still other embodiments from about 4,000 to about 10,000; in additional embodiments from about 4,000 to about 8,000; still further embodiments from about 4,000 to about 6,000; and about 5,000 in another embodiment. The PEG may be a branched or straight chain, and in certain embodiments is a straight chain. The PEG having a molecular weight described in this embodiment may be used in conjunction with ADIr, and optionally, a biocompatible linker, to treat graft versus host disease (GVHD) or cancer.

While ADIr-PEG is the illustrative modified ADIr described herein, as would be recognized by the skilled person ADIr may be modified with other polymers or appropriate molecules for the desired effect, in particular reducing antigenicity and increasing serum half-life.

ADIr may be covalently bonded to a modifying agent, such as PEG, with or without a linker, although a preferred embodiment utilizes a linker.

The linker used to covalently attach ADIr to a modifying agent, e.g. PEG, may be any biocompatible linker. As discussed above, "biocompatible" indicates that the compound or group is non-toxic and may be utilized in vitro or in vivo without causing injury, sickness, disease, or death. A modifying agent, such as PEG, can be bonded to the linker, for example, via an ether bond, a thiol bond, or an amide bond. The linker group includes, for example, a succinyl group, an amide group, an imide group, a carbamate group, an ester group, an epoxy group, a carboxyl group, a hydroxyl group, a carbohydrate, a tyrosine group, a cysteine group, a histidine group, a methylene group, and combinations thereof. In one embodiment, the source of the biocompatible linker is succinimidyl succinate (SS). Other suitable sources of linker may include an oxycarbonylimidazole group (including, for example, carbonylimidazole (CDI)), a nitro phenyl group (including, for example, nitrophenyl carbonate (NCP) or trichlorophenyl carbonate (TCP)), a trysylate group, an aldehyde group, an isocyanate group, a vinylsulfone group, or a primary amine. In another embodiment, the linker is derived from SS, SPA, SCM, or NHS; in certain embodiments, SS, SPA, or NHS are used, and in other embodiments, SS or SPA are used. Thus, in certain embodiments, potential linkers can be formed from methoxy-PEG succinimidyl succinate (SS), methoxy-PEG succinimidyl glutarate (SG), methoxy-PEG succinimidyl carbonate (SC), methoxy-PEG succinimidyl carboxymethyl ester (SCM), methoxy-PEG2 N-hydroxy succinimide (NHS), methoxy-PEG succinimidyl butanoate (SBA), methoxy-PEG succinimidyl propionate (SPA), methoxy-PEG succinimidyl glutaramide, and methoxy-PEG succinimidyl succinamide.

Alternatively, ADIr may be coupled directly to a modifying agent, such as PEG (i.e., without a linker) through an amino group, a sulfhydryl group, a hydroxyl group or a carboxyl group.

ADIr may be covalently bonded to PEG, via a biocompatible linker, using methods known in the art, as described, for example, by Park et al, Anticancer Res., 1:373-376 (1981); and Zaplipsky and Lee, Polyethylene Glycol Chemistry: Biotechnical and Biomedical Applications, J. M. Harris, ed., Plenum Press, NY, Chapter 21 (1992), the disclosures of which are hereby incorporated by reference herein in their entirety.

The attachment of PEG to ADIr increases the circulating half-life of ADIr. Generally, PEG is attached to a primary amine of ADIr. Selection of the attachment site of PEG, or other modifying agent, on the ADIr is determined by the role of each of the sites within the active domain of the protein, as would be known to the skilled artisan. PEG may be attached to the primary amines of ADIr without substantial loss of enzymatic activity. For example, the lysine residues present in ADIr are all possible points at which ADIr as described herein can be attached to PEG via a biocompatible linker, such as SS, SPA, SCM, SSA and/or NHS. PEG may also be attached to other sites on ADIr, as would be apparent to one skilled in the art in view of the present disclosure.

From 1 to about 30 PEG molecules may be covalently bonded to ADIr. In certain embodiments, ADIr is modified with one PEG molecule. In other embodiments, ADIr is modified with more than one PEG molecule. In one embodiment, ADIr is modified with about 1 to about 10, or from about 7 to about 15 PEG molecules, and in one embodiment from about 2 to about 8 or about 9 to about 12 PEG molecules. In another embodiment, the ADIr is modified with 2, 3, 4, 5, 6, 7, 8, 9, 10, 11, 12, 13, 14, or 15 PEG molecules. In one specific embodiment, ADIr is modified with 4.5-5.5 PEG molecules per ADIr. In another embodiment, ADIr is modified with 5±1.5 PEG molecules.

In another embodiment, about 15% to about 70% of the primary amino groups in ADIr are modified with PEG, in one embodiment about 20% to about 65%, about 25% to about 60%, or in certain embodiments about 30% to about 55%, or 45% to about 50%, and in other embodiments about 50% of the primary amino groups in arginine deiminase are modified with PEG. When PEG is covalently bonded to the end terminus of ADIr, it may be desirable to have only 1 PEG molecule utilized. Increasing the number of PEG units on ADIr increases the circulating half life of the enzyme. However, increasing the number of PEG units on ADIr decreases the specific activity of the enzyme. Thus, a balance needs to be achieved between the two, as would be apparent to one skilled in the art in view of the present disclosure.

In the present invention, a common feature of biocompatible linkers is that they attach to a primary amine of arginine deiminase via a succinimide group. Once coupled with ADIr, SS-PEG has an ester linkage next to the PEG, which may render this site sensitive to serum esterase, which may release PEG from ADIr in the body. SPA-PEG and PEG2-NHS do not have an ester linkage, so they are not sensitive to serum esterase.

In certain embodiments, a biocompatible linker is used in the present invention. PEG which is attached to the protein may be either a straight chain, as with SS-PEG, SPA-PEG and SC-PEG, or a branched chain of PEG may be used, as with PEG2-NHS.

In certain embodiments, pegylation sites associated with ADIr located at or adjacent to the catalytic region of the enzyme are modified. For purposes of the present invention, the phrase "pegylation site" may be defined as any site or position of ADI or a ADIr that may be covalently modified with polyethylene glycol. A "pegylation site" can be considered located at or adjacent the catalytic region of the enzyme where pegylation of the site results in a significant reduction in catalytic activity of the enzyme. The pegylation of such sites has traditionally resulted in the inactivation of the enzyme. For example, ADI from Mycoplasma hominis has a lysine at the 112 position which can be considered to be at or adjacent the catalytic region of the enzyme. The attachment of PEG to this lysine at the 112 position can inactivate the enzyme. In addition, ADI from Mycoplasma hominis has a cysteine at the 397 position which can be considered to be at or adjacent the catalytic region of the enzyme. The amino acid substitutions for cysteine at the 397 position can inactivate the enzyme. In particular, substituting alanine, histidine, arginine, serine, lysine or tyrosine for cysteine at the 397 position can result in a loss of all detectable enzyme activity. ADI from Mycoplasma hominis also has three lysines located near this conserved cysteine, in particular Lys374, Lys405 and Lys408. The attachment of PEG to Lys374, Lys405, Lys408 or combinations thereof can inactivate the enzyme.

It is to be understood that ADIr derived from other organisms may also have pegylation sites corresponding to 112 position of ADI from Mycoplasma hominis. In addition, ADI from some organisms may have lysines corresponding to the same general location as the 112 position of ADI from Mycoplasma hominis. The location of lysine in ADI from such organisms are known to the skilled person and are described in U.S. Pat. No. 6,635,462.

Thus, in one embodiment, the present invention provides for certain amino acid substitutions in the polypeptide chain of ADIr. These amino acid substitutions provide for modified ADIr that loses less activity when modified by a modifying agent, e.g., upon pegylation. By eliminating pegylation sites, or other known modification sites, at or adjacent to the catalytic region of enzyme, optimal modification, e.g., pegylation, can be achieved without the loss of activity.

It is to be understood that other embodiments of the invention are based on the understanding that certain structural characteristics of arginine deiminase may prevent or interfere with the proper and rapid renaturation when produced via recombinant technology. In particular, these structural characteristics hinder or prevent the enzyme from assuming an active conformation during recombinant production. For purposes of the present invention, the phrase "active conformation" may be defined as a three-dimensional structure that allows for enzymatic activity by unmodified or modified arginine deiminase. The active conformation may, in particular, be necessary for catalyzing the conversion of arginine into citrulline. The phrase "structural characteristic" may be defined as any trait, quality or property of the polypeptide chain resulting from a particular amino acid or combination of amino acids. For instance, arginine deiminase may contain an amino acid that results in a bend or kink in the normal peptide chain and thus hinders the enzyme from assuming an active conformation during renaturation of the enzyme. In particular, arginine deiminase from Mycoplasma hominis has a proline at the 210 position that may result in a bend or kink in the peptide chain, making it more difficult to renature the enzyme during recombinant production. It is to be understood that arginine deiminase derived from other organisms may also have sites corresponding to the 210 position of arginine deiminase from Mycoplasma hominis.

The present invention thus again provides for certain amino acid substitutions in the polypeptide chain of wild type arginine deiminases. Such amino acid substitutions can eliminate the problematic structural characteristics in the peptide chain of arginine deiminase. Such amino acid substitutions provide for improved renaturation of the modified arginine deiminase. These amino acid substitutions make possible rapid renaturing of modified arginine deiminases using reduced amounts of buffer. These amino acid substitutions may also provide for increased yields of renatured modified arginine deiminase. In one embodiment of the invention, the modified arginine deiminase has an amino acid substitution at P210 or the equivalent residue. As mentioned above, arginine deiminase derived from *Mycoplasma hominis* has the amino acid proline located at the 210 position. While not limiting the present invention, it is presently believed that the presence of the amino acid proline at position 210 results in a bend or kink in the normal polypeptide chain that increases the difficulty of renaturing (i.e., refolding) arginine deiminase. Substitutions for proline at position 210 make possible the rapid renaturation of modified arginine deiminase using reduced amounts of buffer. Substitutions for proline at position 210 may also provide for increased yields of renatured modified arginine deiminase. In one embodiment, the proline at position 210 is substituted with serine. It is to be understood that in accordance with this aspect of the invention, other substitutions at position 210 may be made. Examples of other substitutions include Pro210 to Thr210, Pro210 to Arg210, Pro210 to Asn210, Pro210 to Gln210 or Pro210 to Met210. By eliminating those structural characteristics associated with the amino acid of position 210 of the wild-type arginine deiminase, proper refolding of the enzyme can be achieved.

The methods of the present invention can involve either in vitro or in vivo applications. In the case of in vitro applications, including cell culture applications, the compounds described herein can be added to the cells in cultures and then incubated. The compounds of the present invention may also be used to facilitate the production of monoclonal and/or polyclonal antibodies, using antibody production techniques well known in the art. The monoclonal and/or polyclonal antibodies can then be used in a wide variety of diagnostic applications, as would be apparent to one skilled in the art.

The in vivo means of administration of the compounds of the present invention will vary depending upon the intended application. Administration of the ADIr compositions described herein, in pure form or in an appropriate pharmaceutical composition, can be carried out via any of the accepted modes of administration of agents for serving similar utilities. The pharmaceutical compositions can be prepared by combining ADIr, e.g., ADIr-PEG, ADIr-PEG 20, with an appropriate physiologically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. In addition, other pharmaceutically active ingredients (including other anti-cancer agents as described elsewhere herein) and/or suitable excipients such as salts, buffers and stabilizers may, but need not, be present within the composition. Administration may be achieved by a variety of different routes, including oral, parenteral, nasal, intravenous, intradermal, subcutaneous or topical. Modes of administration depend upon the nature of the condition to be treated or prevented. Thus, ADIr-PEG, e.g., ADIr-PEG 20, may be administered orally, intranasally, intraperitoneally, parenterally, intravenously, intralymphatically, intratumorly, intramuscularly, interstitially, intra-arterially, subcutaneously, intraocularly, intrasynovial, transepithelial, and transdermally. An amount that, following administration, reduces, inhibits, prevents or delays the progression and/or metastasis of a cancer is considered effective. In certain embodiment, the ADIr compositions herein increase median survival time of patients by a statistically significant amount. In one embodiment, the ADIr treatments described herein increase median survival time of a patient by 4 weeks, 5 weeks, 6 weeks, 7 weeks, 8 weeks, 9 weeks, 10 weeks, 15 weeks, 20 weeks, 25 weeks, 30 weeks, 40 weeks, or longer. In certain embodiments, ADIr treatments increase median survival time of a patient by 1 year, 2 years, 3 years, or longer. In one embodiment, the ADIr treatments described herein increase progression-free survival by 2 weeks, 3 weeks, 4 weeks, 5 weeks, 6 weeks, 7 weeks, 8 weeks, 9 weeks, 10 weeks or longer. In certain embodiments, the ADIr treatments described herein increase progression-free survival by 1 year, 2 years, 3 years, or longer.

In certain embodiments, the amount administered is sufficient to result in tumor regression, as indicated by a statistically significant decrease in the amount of viable tumor, for example, at least a 10%, 20%, 30%, 40%, 50% or greater decrease in tumor mass, or by altered (e.g., decreased with statistical significance) scan dimensions. In certain embodiments, the amount administered is sufficient to result in stable disease. In other embodiments, the amount administered is sufficient to result in clinically relevant reduction in symptoms of a particular disease indication known to the skilled clinician.

In certain embodiments the amount administered is sufficient to inhibit NO synthesis, inhibit angiogenesis, and or is sufficient to induce apoptosis in tumor cells or any combination thereof. NO synthesis, angiogenesis and apoptosis may be measured using methods known in the art, see, e.g., *Current Protocols in Immunology* or *Current Protocols in Molecular Biology*, John Wiley & Sons, New York, N.Y. (2009 and updates thereto); Ausubel et al., *Short Protocols in Molecular Biology*, 3$^{rd}$ ed., Wiley & Sons, 1995; and other like references. In one particular embodiment the amount administered inhibits NO synthesis and inhibits the growth of melanoma and complements, adds to, or synergizes with other chemotherapies as described herein, such as cisplatin. Accordingly, one embodiment of the present disclosure provides a method of treating melanoma by administering ADIr-PEG 20 in combination with cisplatin, wherein the treatment depletes endogenous nitric oxide (NO).

The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

The ADIr compositions may be administered alone or in combination with other known cancer treatments, such as radiation therapy, chemotherapy, transplantation, immunotherapy, hormone therapy, photodynamic therapy, etc. The compositions may also be administered in combination with antibiotics.

The ADIr compositions may also be administered alone or in combination with ADI-PEG 20 therapy. In certain embodiments, the ADIr as described herein are used in patients who have been treated with ADI-PEG 20 and who have developed anti-ADI-PEG 20 antibodies. Such patients no longer benefit from ADI-PEG 20 treatment as the enzyme is neutralized by the antibodies. Thus, in certain embodiments, the invention provides a method of treating, ameliorating the symptoms of, or inhibiting the progression of a cancer comprising administering to a patient in need thereof a therapeutically effective amount of a composition comprising ADI-PEG 20, and after a period of time, administering to the patient a composition comprising an ADIr as described herein, thereby treating, ameliorating the symptoms of, or inhibiting the progression of the cancer.

In one embodiment of the method, the period of time is determined by detecting a predetermined level of anti-ADI-PEG 20 antibodies in the patient, wherein the composition comprising an ADIr is administered following detection of the predetermined level of said anti-ADI-PEG 20 antibodies. In certain embodiments, threshold level(s) or predetermined levels of anti-ADI-PEG 20 antibodies in patients to be treated with ADI-PEG 20 and the ADIr of the present invention can be established. A "predetermined threshold level" (also referred to as "predetermined level" or "predetermined cut-off value"), or sometimes referred to as a predetermined cut off, of anti-ADI-PEG 20 antibodies may be established using methods known in the art, for example, using Receiver Operator Characteristic curves or "ROC" curves. In one embodiment, even very low levels of anti-ADI-PEG 20 antibodies is deemed sufficient to warrant switching treatment from ADI-PEG 20 to an ADIr-PEG of the present invention. In certain embodiments, an appropriate level of anti-ADI-PEG 20 that will determine when to terminate ADI-PEG 20 treatment and begin treatment with an ADIr-PEG of the present invention can be determined by the skilled clinician.

In some embodiments, the period of time is determined by detecting or otherwise observing ADI activity in the patient, wherein the composition is administered following detection or observation of a predetermined level of ADI activity. In particular embodiments, the composition is administered following detection or observation of a reduced level of ADI activity in the patient. ADI activity can be measured directly, for example, by assaying a biological sample for at least one indicator of ADI activity, or indirectly, for example, by observing the desired or intended effect of the ADI-PEG 20 treatment. In certain embodiments, an appropriate level of ADI activity that will determine when to terminate ADI-PEG 20 treatment and begin treatment with an ADIr-PEG of the present invention can be determined by the skilled clinician.

Typical routes of administering these and related pharmaceutical compositions thus include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques.

Pharmaceutical compositions according to certain embodiments of the present invention are formulated so as to allow the active ingredients contained therein to be bioavailable upon administration of the composition to a patient. Compositions that will be administered to a subject or patient may take the form of one or more dosage units, where for example, a tablet may be a single dosage unit, and a container of a herein described ADIr composition in aerosol form may hold a plurality of dosage units. Actual methods of preparing such dosage forms are known, or will be apparent, to those skilled in this art; for example, see *Remington: The Science and Practice of Pharmacy*, 20th Edition (Philadelphia College of Pharmacy and Science, 2000). The composition to be administered will, in any event, contain a therapeutically effective amount of an ADIr-PEG of the present disclosure, such as ADIr-PEG 20, for treatment of a disease or condition of interest in accordance with teachings herein. In certain embodiments, the pharmaceutical or therapeutic compositions are sterile and/or pyrogen-free.

A pharmaceutical composition may be in the form of a solid or liquid. In one embodiment, the carrier(s) are particulate, so that the compositions are, for example, in tablet or powder form. The carrier(s) may be liquid, with the compositions being, for example, anoral oil, injectable liquid or an aerosol, which is useful in, for example, inhalatory administration. When intended for oral administration, the pharmaceutical composition is generally either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions, whether they be solutions, suspensions or other like form, may include one or more of the following adjuvants: sterile diluents such as water for injection, saline solution, in certain embodiments, physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition intended for either parenteral or oral administration should contain an amount of ADIr as herein disclosed, such as ADIr-PEG 20, such that a suitable dosage will be obtained. Typically, this amount is at least 0.01% of ADIr in the composition. When intended for oral administration, this amount may be varied to be between 0.1 and about 70% of the weight of the composition. Certain oral pharmaceutical compositions contain between about 4% and about 75% of ADIr-PEG. In certain embodiments, pharmaceutical compositions and preparations according to the present invention are prepared so that a parenteral dosage unit contains between 0.01 to 10% by weight of ADIr-PEG prior to dilution.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. The pharmaceutical composition may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule. The pharmaceutical composition in solid or liquid form may include an agent that binds to ADIr-PEG and thereby assists in the delivery of the compound. Suitable agents that may act in this capacity include monoclonal or polyclonal antibodies, one or more proteins or a liposome. The pharmaceutical composition may consist essentially of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The pharmaceutical compositions may be prepared by methodology well known in the pharmaceutical art. For example, a pharmaceutical composition intended to be administered by injection can be prepared by combining a composition that comprises ADIr-PEG as described herein and optionally, one or more of salts, buffers and/or stabilizers, with sterile, distilled water so as to form a solution. A surfactant may be added to facilitate the formation of a homogeneous solution or suspension. Surfactants are compounds that non-covalently interact with the ADIr-PEG composition so as to facilitate dissolution or homogeneous suspension of the ADIr-PEG in the aqueous delivery system.

The compositions may be administered in a therapeutically effective amount, which will vary depending upon a variety of factors including the activity of the specific compound (e.g., ADIr-PEG) employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

A therapeutically effective amount of one of the compounds of the present invention is an amount that is effective to inhibit tumor growth. Generally, treatment is initiated with small dosages which can be increased by small increments until the optimum effect under the circumstances is achieved. Generally, a therapeutic dosage of compounds of the present invention may be from about 1 to about 200 mg/kg twice a week to about once every two weeks. For example, the dosage may be about 1 mg/kg once a week as a 2 ml intravenous injection to about 20 mg/kg once every 3 days. In a further embodiment, the dose may be from about 50 IU/m$^2$ to about 700 IU/m$^2$, administered about once every 3 days, about once a week, about twice a week, or about once every 2 weeks. In certain embodiments, the dose may be about 50 IU/m$^2$, 60 IU/m$^2$, 70 IU/m$^2$, 80 IU/m$^2$, 90 IU/m$^2$, 100 IU/m$^2$, 110 IU/m$^2$, 120 IU/m$^2$, 130 IU/m$^2$, 140 IU/m$^2$, 150 IU/m$^2$, 160 IU/m$^2$, 170 IU/m$^2$, 180 IU/m$^2$, 190 IU/m$^2$, 200 IU/m$^2$, 210 IU/m$^2$, 220 IU/m$^2$, 230 IU/m$^2$, 240 IU/m$^2$, 250 IU/m$^2$, 260 IU/m$^2$, 270 IU/m$^2$, 280 IU/m$^2$, 290 IU/m$^2$, 300 IU/m$^2$, 310 IU/m$^2$, about 320 IU/m$^2$, about 330 IU/m$^2$, 340 IU/m$^2$ about 350 IU/m$^2$, 360 IU/m$^2$, 370 IU/m$^2$, 380 IU/m$^2$, 390 IU/m$^2$, 400 IU/m$^2$, 410 IU/m$^2$, 420 IU/m$^2$, 430 IU/m$^2$, 440 IU/m$^2$, 450 IU/m$^2$, 500 IU/m$^2$, 550 IU/m$^2$, 600 IU/m$^2$, 620 IU/m$^2$, 630 IU/m$^2$, 640 IU/m$^2$, 650 IU/m$^2$, 660 IU/m$^2$, 670 IU/m$^2$, 680 IU/m$^2$, 690 IU/m$^2$, or about 700 IU/m$^2$ administered about once every 3 days, about once a week, about twice a week, or about once every 2 weeks. In certain embodiments, the dose may be modified as desired by the skilled clinician.

The optimum dosage with ADIr-SS-PEG5,000 may be about twice a week, while the optimum dosage with ADIr-SS-PEG20,000 may be from about once a week to about once every two weeks. In certain embodiments, the optimum dosage with ADIr-SS-PEG20,000 may be about twice a week.

ADIr-PEG may be mixed with a phosphate buffered saline solution, or any other appropriate solution known to those skilled in the art, prior to injection. In one embodiment, a liquid composition comprising ADIr-PEG comprises about 10 to about 12 mg of ADIr, about 20 to about 40 mg of polyethylene glycol, 1.27 mg+5% monobasic sodium phosphate, USP; about 3 mg+5% dibasic sodium phosphate, USP; 7.6 mg+5% sodium chloride, USP; at a pH of about 6.6 to about 7; in an appropriate amount of water for injection (e.g., about 1 ml or about 2 ml). In one embodiment, a liquid composition comprising an ADIr-PEG comprises histidine-HCl, and in certain embodiments, the composition buffer is from about 0.0035 M Histidine-HCl to about 0.35 M Histidine-HCl. In one particular embodiment, the composition is formulated in a buffer comprising 0.035 M Histidine-HCl at pH 6.8 with 0.13 M sodium chloride. In another embodiment, the composition is formulated in a buffer comprising 0.02 M sodium phosphate buffer at pH 6.8 with 0.13 M sodium chloride.

In one embodiment, a composition comprising ADIr or ADIr-PEG has a pH of about 5 to about 9, about 6 to about 8, or about 6.5 to about 7.5. In some embodiments, the composition comprising ADIr has a pH of about 6.8±1.0.

In one embodiment, free PEG in a composition comprising ADIr-PEG is between 1-10%, and in a further embodiment, is less than 7%, less than 6%, less than 5%, less than 4%, less than 3%, less than 2% or less than 1% of the total PEG. In certain embodiments, the unmodified ADIr in a composition comprising ADIr-PEG is less than about 1%, 0.9%, 0.8%, 0.7%, 0.6%, 0.5%, 0.4%, 0.3%, 0.2% or less than 0.1%. Generally, compositions comprising ADIr-PEG have total impurities less than or equal to about 4%, 3%, 2%, 1.5%, 1% or 0.5%. In one embodiment, the endotoxin limit meets the requirements stated in USP, i.e., ≤50 EU/mL.

In one embodiment, the free sulfhydryl in a composition comprising ADIr or ADIr-PEG is greater than about 90%. In some embodiments, the free sulfhydryl in a composition comprising ADIr or ADIr-PEG is about 91%, about 92%, about 93%, about 94% or about 95%, about 96% about 97%, about 98% about 99% or more.

In one embodiment, the ADIr or ADIr-PEG in a composition has a Km of from about 0.1 µM or 0.5 µM to about 15 µM, and in a further embodiment, is from about 1 µM to about 12 µM, about 1 µM to about 10 µM, about 1.5 µM to about 9 µM, about 1.5 µM to about 8 µM or about 1.5 µM to about 7 µM. In certain embodiments, the ADIr or ADIr-PEG in a composition has a Km of about 1.0 µM to about 10 µM or about 1.5 µM to about 6.5 µM. In some embodiments, the ADIr or ADIr-PEG in a composition has a Km of about, at least about, or less than about 0.1 µM, about 0.5 µM, about 1.0 µM, about 1.5 µM, about 2 µM, about 2.5 µM, about 3 µM, about 3.5 µM, about 4 µM, about 4.5 µM, about 5 µM, about 5.5 µM, about 6 µM, about 6.5 µM, or about 7 µM, or about 8 µM, or about 9 µM, or about 10 µM.

In one embodiment, the ADIr or ADIr-PEG in a composition has a Kcat of from about 0.5 sec$^{-1}$ to about 80 sec$^{-1}$, or about 0.5 sec$^{-1}$ to about 70 sec$^{-1}$, or about 0.5 sec$^{-1}$ to about 60 sec$^{-1}$, or about 0.5 sec$^{-1}$ to about 50 sec$^{-1}$, or about 0.5 sec$^{-1}$ to about 40 sec$^{-1}$, or about 0.5 sec$^{-1}$ to about 30 sec$^{-1}$, or about 0.5 sec$^{-1}$ to about 20 sec$^{-1}$, or about 0.5 sec$^{-1}$ to about 15 sec$^{-1}$, and in a further embodiment, is from about 0.5 sec$^{-1}$ to about 80 sec$^{-1}$, or about 1 sec$^{-1}$ to about 80 sec$^{-1}$, or about 5 sec$^{-1}$ to about 80 sec$^{-1}$, or about 10 sec$^{-1}$ to about 80 sec$^{-1}$, or about 20 sec$^{-1}$ to about 80 sec$^{-1}$, or about 30 sec$^{-1}$ to about 80 sec$^{-1}$, or about 40 sec$^{-1}$ to about 80 sec$^{-1}$, or about 50 sec$^{-1}$ to about 80 sec$^{-1}$, or about 60 sec$^{-1}$ to about 80 sec$^{-1}$, or about 70 sec$^{-1}$ to about 80 sec$^{-1}$, or about 1 sec$^{-1}$ to about 12 sec$^{-1}$, about 1 sec$^{-1}$ to about 10 sec$^{-1}$, about 1.5 sec$^{-1}$ to about 9 sec$^{-1}$, about 2 sec$^{-1}$ to about 8 sec$^{-1}$ or about 2.5 sec$^{-1}$ to about 7 sec$^{-1}$. In certain embodiments, the ADIr or ADIr-PEG in a composition has a Kcat of about 2.5 sec$^{-1}$ to about 7.5 sec$^{-1}$. In some embodiments, the ADIr or ADIr-PEG in a composition has a Kcat of about or at least about 2.5 sec$^{-1}$, about 3 sec$^{-1}$, about 3.5 sec$^{-1}$, about 4 sec$^{-1}$, about 4.5 sec$^{-1}$, about 5 sec$^{-1}$, about 5.5 sec$^{-1}$, about 6 sec$^{-1}$, about 6.5 sec$^{-1}$, about 7 sec$^{-1}$, about 7.5 sec$^{-1}$ or about 8 sec$^{-1}$, about 10 sec$^{-1}$, about 15 sec$^{-1}$, about 20 sec$^{-1}$, about 25 sec$^{-1}$, about 30 sec$^{-1}$, about 35 sec$^{-1}$, about 40 sec$^{-1}$, about 45 sec$^{-1}$, about 50 sec$^{-1}$, about 55 sec$^{-1}$, about 60 sec$^{-1}$, about 65 sec$^{-1}$, about 70 sec$^{-1}$, about 75 sec$^{-1}$, about 80 sec$^{-1}$, about 85 sec$^{-1}$, about 90 sec$^{-1}$, about 95 sec$^{-1}$, or about 100 sec$^{-1}$.

In one embodiment, the ADIr or ADIr-PEG in a composition has a conductivity (also referred to in the art as specific conductance) of about 5 mS/cm to about 20 mS/cm, and in further embodiments, from about 5 mS/cm to about 15 mS/cm, about 7 mS/cm to about 15 mS/cm, about 9 mS/cm to about 15 mS/cm or about 10 mS/cm to about 15 mS/cm. In some embodiments, the ADIr or ADIr-PEG in a composition has a conductivity of about 9 mS/cm, about 10 mS/cm, about 11 mS/cm, about 12 mS/cm or about 13 mS/cm, about 14 mS/cm or about 15 mS/cm. In certain embodiments, the ADIr or ADIr-PEG in a composition has a conductivity of about 13 mS/cm±1.0 mS/cm.

In one embodiment, the ADIr or ADIr-PEG in a composition has an osmolality of about 50 mOsm/kg to about 500 mOsm/kg, about 100 mOsm/kg to about 400 mOsm/kg, about 150 mOsm/kg to about 350 mOsm/kg, about 200 mOsm/kg to about 350 mOsm/kg or about 250 mOsm/kg to about 350 mOsm/kg. In certain embodiments, the ADIr or ADIr-PEG in a composition has an osmolality of about 300±30 mOsm/kg.

In one embodiment, the protein concentration is about 11.0±1.0 mg/mL. In certain embodiments, the protein concentration is between about 8 and about 15 mg/mL. In another embodiment, the protein concentration is about 8, 9, 10, 10.5, 11, 11.5, 12, 12.5, 13, 13.5, 14, or 15 mg/mL.

In one embodiment, the specific enzyme activity is between about 5.0 and 90 IU/mg or between about 5 and 55 IU/mg, where 1 IU is defined as the amount of enzyme that converts one pmol of arginine into one pmol of citrulline and 1 µmol of ammonia in one minute at 37° C. and the potency is 100±20 IU/mL. In another embodiment, the specific enzyme activity is about 5.5, 6, 6.5, 7, 7.5, 8, 8.5, 9.0, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 35, 40, 45, 50, 55, 55, 60, 65, 70, 75, 80, 85, 90, 95, or 100±2.0 IU/mg. In one particular embodiment, the specific enzyme activity is 9±2.0 IU/mg.

Compositions comprising ADIr-PEG of the present disclosure may also be administered simultaneously with, prior to, or after administration of one or more other therapeutic agents, including ADI-PEG 20. Such combination therapy may include administration of a single pharmaceutical dosage formulation which contains a compound of the invention and one or more additional active agents, as well as administration of compositions comprising ADIr-PEG (e.g., ADIr-PEG 20) of the invention and each active agent in its own separate pharmaceutical dosage formulation. For example, ADIr-PEG as described herein and the other active agent can be administered to the patient together in a single oral dosage composition such as a tablet or capsule, or each agent administered in separate oral dosage formulations. Similarly, ADIr-PEG as described herein and the other active agent can be administered to the patient together in a single parenteral dosage composition such as in a saline solution or other physiologically acceptable solution, or each agent administered in separate parenteral dosage formulations, by the same or different routes (e.g., one by injection, one by oral). Where separate dosage formulations are used, the compositions comprising ADIr-PEG and one or more additional active agents can be administered at essentially the same time, i.e., concurrently, or at separately staggered times, i.e., sequentially and in any order; combination therapy is understood to include all these regimens.

Thus, in certain embodiments, also contemplated is the administration of the ADIr compositions of this disclosure in combination with one or more other therapeutic agents. Such therapeutic agents may be accepted in the art as a standard treatment for a particular disease state as described herein, such as a particular cancer or GVHD. Exemplary therapeutic agents contemplated include cytokines, growth factors, steroids, NSAIDs, DMARDs, anti-inflammatories, chemotherapeutics, radiotherapeutics, autophagy inhibitors, or other active and ancillary agents.

In certain embodiments, the ADIr compositions disclosed herein may be administered in conjunction with any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and docetaxel (TAXOTERE®, Rhne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid derivatives such as Targretin™ (bexarotene), Panretin™ (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin. Further chemotherapeutic agents include sorafenib and other protein kinase inhibitors such as afatinib, axitinib, bevacizumab, cetuximab, crizotinib, dasatinib, erlotinib, fostamatinib, gefitinib, imatinib, lapatinib, lenvatinib, mubritinib, nilotinib, panitumumab, pazopanib, pegaptanib, ranibizumab, ruxolitinib, trastuzumab, vandetanib, vemurafenib, and sunitinib; sirolimus (rapamycin), everolimus and other mTOR inhibitors. Pharmaceutically acceptable salts, acids or derivatives of any of the above are also contemplated for use herein.

In certain embodiments, the ADIr compositions disclosed herein may be administered in conjunction with any number of autophagy inhibitors. In some preferred embodiments, the autophagy inhibitor is selected from the group consisting of: chloroquine, 3-methyladenine, hydroxychloroquine (Plaquenil™), bafilomycin A1,5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels, adenosine, N6-mercaptopurine riboside, wortmannin, and vinblastine. In addition, antisense or siRNA that inhibits expression of proteins essential for autophagy, such as for example ATG5, may also be used.

In one embodiment, the combination of ADIr-PEG with one or more therapeutic agents acts complementary, additively, or synergistically. In this regard, complementary or synergizing agents are described herein, which include a therapeutic agent (e.g., chemotherapeutic agent, autophagy inhibitor, mTOR inhibitor, or any other therapeutic agent used for the treatment of cancer, GVHD, or inflammatory bowel disease as described herein) that is capable of acting complementary or synergistically with ADIr-PEG as provided herein, where such complementarity or synergy manifests as a detectable effect that is greater (i.e., in a statistically significant manner relative to an appropriate control condition) in magnitude than the effect that can be detected when the chemotherapeutic agent is present but the ADIr-PEG composition is absent, and/or when the ADIr-PEG is present but the chemotherapeutic agent is absent. Methods for measuring synergy and complementarity are known in the art (see e.g., Cancer Res Jan. 15, 2010 70; 440).

The compositions comprising ADIr, and optionally other therapeutic agents, as described herein may be used in therapeutic methods for treating cancer and methods for preventing metastasis of a cancer. Thus, the present invention provides for methods for treating, ameliorating the symptoms of, or inhibiting the progression of or prevention of a variety of different cancers. In another embodiment, the present disclosure provides methods for treating, ameliorating the symptoms of, or inhibiting the progression of GVHD. In particular the present disclosure provides methods for treating, ameliorating the symptoms of, or inhibiting the progression of a cancer or GVHD in a patient comprising administering to the patient a therapeutically effective amount of ADIr composition as described herein, optionally, following treatment with ADI-PEG 20, particularly where a patient develops anti-ADI-PEG 20 antibodies, thereby treating, ameliorating the symptoms of, or inhibiting the progression of the cancer or GVHD. Thus, the ADIr compositions described herein may be administered to an individual afflicted with inflammatory bowel disease (e.g., Crohn's disease; ulcerative colitis), GVHD or a cancer, including, but not limited to hepatocellular carcinoma, leukemia (e.g. acute myeloid leukemia and relapsed acute myeloid leukemia), melanoma including metastatic melanoma, sarcomas (including, but not limited to, metastatic sarcomas, uterine leiomyosarcoma), pancreatic cancer, prostate cancer (such as, but not limited to, hormone refractory prostate cancer), mesothelioma, lymphatic leukemia, chronic myelogenous leukemia, lymphoma, small cell lung cancer, breast cancer, ovarian cancer, colorectal cancer, gastric cancer (including, but not limited to, gastric adenocarcinoma), glioma, glioblastoma multi-form, retinoblastoma, neuroblastoma, non-small cell lung cancer (NSCLC), kidney cancer (including but not limited to renal cell carcinoma), bladder cancer, uterine cancer, esophageal cancer, brain cancer, head and neck cancers (including, but not limited to, squamous cell carcinoma of the head and neck; cancer of the tongue), cervical cancer, testicular cancer, gallbladder, cholangiocarcinoma, and stomach cancer.

In another embodiment, the present disclosure provides a method of treating, ameliorating the symptoms of, or inhibiting the progression of a cancer in a patient comprising administering to the patient a composition comprising ADIr, and optionally one or more other therapeutic agents, as described herein, wherein the cancer is deficient in ASS, ASL, or both. In this regard, ASS or ASL deficiency may be a reduction in expression as measured by mRNA expression or protein expression, or may be a reduction in protein activity, and generally comprises a statistically significant reduction in expression or activity as determined by the skilled person. Reduced ASS or ASL expression or activity may be a reduction in expression or activity of about 5%, 10%, 15%, 20%, 25%, 30%, 35%, 40%, 45%, 50%, 55%, 60%, 65%, 70%, or more, as compared to expression or activity in an appropriate control sample known to be cancer free. In certain embodiments, ASS or ASL expression or activity is reduced by at least twofold as compared to expression or activity in a non-cancer control sample.

In certain embodiments, the reduced expression or activity of ASS or ASL results from methylation of the ASS or ASL promoter or inhibition of the ASS or ASL promoter. In another embodiment the reduction in expression or activity of ASS or ASL results from a DNA mutation (e.g., one or more point mutations, small deletions, insertions, and the like) or a chromosomal abnormality resulting in deletion of the gene. In one embodiment, the cancer is ASS or ASL negative, meaning no expression or activity is observed.

Reduction in ASS or ASL expression or activity may be measured using any methods known in the art, such as but not limited to, quantitative PCR, immunohistochemistry, enzyme activity assays (e.g., assay to measure conversion of citrulline into argininosuccinate or conversion of argininosuccinate into arginine and fumarate), and the like.

Thus, the present invention provides methods for treating, ameliorating the symptoms of, or inhibiting the progression of a cancer in a patient comprising administering to the patient a composition comprising ADIr as described herein, wherein the cancer exhibits reduced expression or activity of ASS or ASL, or both, wherein the cancer includes, but is not limited to hepatocellular carcinoma, leukemia (e.g. acute myeloid leukemia and relapsed acute myeloid leukemia), melanoma including metastatic melanoma, sarcomas (including, but not limited to, metastatic sarcomas, uterine leiomyosarcoma), pancreatic cancer, prostate cancer (such as, but not limited to, hormone refractory prostate cancer), mesothelioma, lymphatic leukemia, chronic myelogenous leukemia, lymphoma, small cell lung cancer, breast cancer, ovarian cancer, colorectal cancer, gastric cancer (including, but not limited to, gastric adenocarcinoma), glioma, glioblastoma multi-form, retinoblastoma, neuroblastoma, non-small cell lung cancer (NSCLC), kidney cancer (including but not limited to renal cell carcinoma), bladder cancer, uterine cancer, esophageal cancer, brain cancer, head and neck cancers (including, but not limited to, squamous cell carcinoma of the head and neck; cancer of the tongue), cervical cancer, testicular cancer, gallbladder, cholangiocarcinoma, and stomach cancer.

Various studies in the literature have shown that ASS is deficient in the following tumors: acute myelogenous leukemia (AML), bladder, breast, colorectal, gastric, glioblastoma, HCC, lymphoma, melanoma, mesothelioma, non-small cell lung, ovarian, pancreatic, prostate, renal, sarcoma, and small cell lung. Accordingly, treatment of these ASS-deficient cancers is specifically contemplated herein, with ADIr-PEG alone or in combination with other treatments, including treatment first with ADI-PEG 20.

The present invention further provides methods for treating, ameliorating the symptoms of, or inhibiting the progression of cancer in a patient comprising administering to the patient a composition comprising ADIr as described herein (e.g., ADIr-PEG and in particular ADIr-PEG 20), in combination with an autophagy inhibitor. In one embodiment, the present invention provides methods for treating cancer in a patient comprising administering to the patient a therapeutically effective amount of a composition comprising ADIr as described herein in combination with autophagy inhibitor wherein the cancer is pancreatic cancer or small cell lung cancer.

In certain embodiments, the present invention provides methods of treatment where administration of the compositions comprising ADIr described herein depletes arginine in the plasma for at least one month, 2 months, 3 months, 4 months, 5 months, 6 months or longer. In another embodiment, the present invention provides methods of treatment where administration of the compositions comprising ADIr described herein depletes arginine in the plasma for at least one month, 2 months, 3 months, 4 months, 5 months, 6 months or longer after terminating treatment with ADI-PEG 20 following detection of anti-ADI-PEG 20 antibodies.

EXAMPLES

Example 1

Screening and Selection of ADI Enzymes that have Low Cross-Reactivity with Patient Anti-ADI-PEG 20 Antibodies This example describes the screening and selection of ADI enzymes that have low cross-reactivity with patient anti-ADI-PEG 20 antibodies.

From a large number of ADI enzymes, Table 1 lists 24 ADI enzymes selected for their sequence percent identity relative to *M. hominis* ADI. From the literature, *M. hominis*, *M. arginini*, and *M. arthritidis* ADI amino acid sequences are closely related and these enzymes have good catalytic properties. More recently, additional ADI enzymes have been discovered that have sequences closely related to these three. More distantly related *Mycoplasma* ADI enzymes have been identified, although less is known about them. Even more distantly related ADI enzymes from bacterial and other sources exist.

TABLE 1

Selected ADI Sequences with Varying Degrees of Similarity to *M. hominis* ADI

| ORGANISM | PERCENT IDENTITY | SEQUENCE ACCESSION NUMBER | SEQ ID NO: |
|---|---|---|---|
| Mycoplasma hominis | 100.0% | gi\|728876 | 1 |
| Mycoplasma phocicerebrale | 82.1% | gi\|154184333 | 2 |
| Mycoplasma arginini | 82.1% | gi\|728875 | 3 |
| Mycoplasma arthritidis | 80.4% | gi\|238692486 | 4 |
| Mycoplasma orale | 77.8% | gi\|2170494 | 5 |
| Mycoplasma gateae | 76.8% | gi\|148361415 | 6 |
| Mycoplasma phocidae | 75.3% | gi\|154184335 | 7 |
| Mycoplasma columbinum | 58.2% | gi\|343491689 | 8 |
| Mycoplasma iowae | 55.2% | gi\|350546321 | 9 |
| Mycoplasma crocodyli | 52.3% | gi\|291600396 | 10 |
| Mycqplasma fermentans | 52.0% | gi\|238809916 | 11 |
| Mycoplasma penetrans | 51.7% | gi\|26554060 | 12 |
| Mycoplasma gallisepticum | 51.5% | gi\|31544533 | 13 |
| Mycoplasma alligatoris | 50.8% | gi\|292552899 | 14 |
| Mycoplasma pneumoniae | 50.7% | gi\|440453687 | 15 |
| Mycoplasma mobile | 47.3% | gi\|47458387 | 16 |
| Streptococcus pyogenes | 37.7% | gi\|15675444 | 17 |
| Enterococcus faecalis | 37.1% | gi\|60389809 | 18 |
| Mycoplasma capricolum | 36.6% | gi\|83319656 | 19 |
| Halothermothrix orenii | 34.8% | gi\|254803235 | 20 |
| Staphylococcus aureus | 33.8% | gi\|123549453 | 21 |
| Pseudomonas plecoglossicida | 28.7% | gi\|154183755 | 22 |
| Pseudomonas putida | 27.5% | gi\|431801013 | 23 |
| Pseudomonas aeruginosa | 27.0% | gi\|452183609 | 24 |
| Mycobacterium bovis | 26.8% | gi\|378770764 | 25 |

Several of the protein sequences available in the public databases may not have been full-length ADI sequences. In those cases, the publicly available sequences were extended where needed to make full-length ADI based on known ADI sequences. In certain cases, the ADI proteins were modified elsewhere (e.g., C251S substitution). These synthesized ADI sequences are provided in SEQ ID NOs:26-32 and correspond to the extended and/or modified ADI sequences of *Mycoplasma arginini* (C251S), *Mycoplasma arthritidis* (C251S), *Mycoplasma phocicerebrale, Mycoplasma gateae, Mycoplasma phocidae, H. orenii*, and *Mycobacterium bovis*.

A number of ADI enzymes from a variety of organisms were characterized to determine which enzymes would be expected to remove and maintain low concentrations of arginine in patient blood, even in the presence of anti-ADI-PEG 20 antibodies. Table 2 (below) lists a selected subset of ADI enzymes from Table 1 that were studied. As detailed below, the data from these studies show that ADI from a number of species that are closely related to *M. hominis*, based on sequence identity, have sufficiently good enzyme catalytic properties and reduced cross-reactivity with anti-ADI-PEG 20 antibodies.

ADI Preparation.

Recombinant ADI enzymes were cloned, expressed, and purified for testing according to standard protocols, as described, for example, in Gallego et al., PLOS One, 7(10): e47886, 2012; Monstadt and Holldorf, Biochem. J. 273:739-745, 1990; Joo Noh et al., Molecules and Cells. 13:137-143, 2002; and Sugimura et al., Infection and Immunity. 58:2510-2515, 1990.

Human Anti-ADI-PEG20 Antibody Purification.

Anti-ADI-PEG20 antibody was purified from plasma samples of patients who had received ADI-PEG20 during a clinical study. A total of 60 ml of plasma was pooled from 8 different patients that had reached high titer (titer>/=4) against ADI-PEG20 as determined by an ELISA assay. A two-step purification was used, a Protein "A" chromatography (GE Healthcare) followed by an ADI affinity chromatography. ~20 mg of purified antibody was obtained and stored at −80° C. in aliquots until needed.

ADI Enzyme Assays.

Arginine deiminase (ADI) catalyzes the conversion of L-arginine to L-citrulline and ammonia. The amount of L-citrulline can be detected by a colorimetric endpoint assay (see, for example, Knipp and Vasak, Analytical Biochem. 286:257-264, 2000) and compared to a standard curve of known amounts of L-citrulline in order to calculate the specific activity of ADI expressed as IU/mg of protein. One IU of enzyme activity is defined as the amount of enzyme that produces 1 µmol of citrulline per minute at the pH and temperature being tested. Standard assay conditions were performed at 37° C. in Physiological HEPES Buffer (PHB) 50 mM HEPES, 160 mM NaCl pH 7.4 (Lang and Zander, Clin Chem Lab Med. 37:563-571, 1999) plus 0.1% BSA. All samples and standards were run in duplicate or triplicate where conditions permitted.

Km and Kcat values were determined by using a variation of the activity assay described above. As with the activity assay, all reactions were run at 37° C. in PHB plus 0.1% BSA. Enzyme concentration, reaction time, and substrate concentration range were adjusted for each of the ADI or ADIr constructs to account for their differences in activity. In general, 2 nM enzyme, 5 minute reaction time, and a 0-160 µM arginine was used as starting conditions. When optimizing the conditions, particular attention was paid towards the amount of substrate consumed as a percentage of total substrate added to the reaction. The lower limit of detection is 1 µM of citrulline with the lower limit of quantitation being 2 µM. A citrulline standard curve was run on every plate and used to quantify the citrulline produced by the enzymatic reaction.

Activity assays were also performed to assess enzymatic activity in the presence of anti-ADI-PEG20 (antibody neutralization profiles). These assays were performed as described above and in the presence of 800 nM, 400 nM, 200 nM, 100 nM, 50 nM, 25 nM, 12.5 nM, and 0 nM of anti-ADI-PEG20 antibodies.

Calculations.

The citrulline concentration (µM) produced in each reaction well was calculated and averaged using the citrulline standard curve. The velocity of each reaction was then calculated in µM/min/50 nM ADI. Specific activity (IU/mg or µmols product/min/mg ADI) was calculated by multiplying this value by the "IU" factor (IU factor was calculated from the molecular weight of the ADI and the reaction volume). The results are summarized in Table 2 below.

TABLE 2

Selected ADI Sequences and Properties

| ORGANISM | SEQUENCE PERCENT IDENTITY | SPECIFIC ACTIVITY (IU/MG)*** | NUMBER OF SURFACE RESIDUE CHANGES* | REDUCED AB CROSS-REACTIVITY**** |
|---|---|---|---|---|
| Mycoplasma hominis | 100.0 | + | 0 | — |
| Mycoplasma phocicerebrale | 82.1 | + | 33 | Y |

TABLE 2-continued

Selected ADI Sequences and Properties

| ORGANISM | SEQUENCE PERCENT IDENTITY | SPECIFIC ACTIVITY (IU/MG)*** | NUMBER OF SURFACE RESIDUE CHANGES* | REDUCED AB CROSS-REACTIVITY**** |
|---|---|---|---|---|
| Mycoplasma arginini | 82.1 | + | 50 | Y |
|

```
Ala Val Arg Ala Phe Leu Leu Ser Lys Pro Thr His Glu Met Val Glu
        115                 120                 125

Phe Met Met Ser Gly Ile Thr Lys Tyr Glu Leu Gly Val Glu Ser Glu
    130                 135                 140

Asn Glu Leu Ile Val Asp Pro Met Pro Asn Leu Tyr Phe Thr Arg Asp
145                 150                 155                 160

Pro Phe Ala Ser Val Gly Asn Gly Val Thr Ile His Phe Met Arg Tyr
                165                 170                 175

Ile Val Arg Arg Arg Glu Thr Leu Phe Ala Arg Phe Val Phe Arg Asn
            180                 185                 190

His Pro Lys Leu Val Lys Thr Pro Trp Tyr Tyr Asp Pro Ala Met Lys
        195                 200                 205

Met Pro Ile Glu Gly Gly Asp Val Phe Ile Tyr Asn Asn Glu Thr Leu
    210                 215                 220

Val Val Gly Val Ser Glu Arg Thr Asp Leu Asp Thr Ile Thr Leu Leu
225                 230                 235                 240

Ala Lys Asn Ile Lys Ala Asn Lys Glu Val Glu Phe Lys Arg Ile Val
                245                 250                 255

Ala Ile Asn Val Pro Lys Trp Thr Asn Leu Met His Leu Asp Thr Trp
            260                 265                 270

Leu Thr Met Leu Asp Lys Asn Lys Phe Leu Tyr Ser Pro Ile Ala Asn
        275                 280                 285

Asp Val Phe Lys Phe Trp Asp Tyr Asp Leu Val Asn Gly Gly Ala Glu
    290                 295                 300

Pro Gln Pro Gln Leu Asn Gly Leu Pro Leu Asp Lys Leu Leu Ala Ser
305                 310                 315                 320

Ile Ile Asn Lys Glu Pro Val Leu Ile Pro Ile Gly Gly Ala Gly Ala
                325                 330                 335

Thr Glu Met Glu Ile Ala Arg Glu Thr Asn Phe Asp Gly Thr Asn Tyr
            340                 345                 350

Leu Ala Ile Lys Pro Gly Leu Val Ile Gly Tyr Asp Arg Asn Glu Lys
        355                 360                 365

Thr Asn Ala Ala Leu Lys Ala Ala Gly Ile Thr Val Leu Pro Phe His
    370                 375                 380

Gly Asn Gln Leu Ser Leu Gly Met Gly Asn Ala Arg Cys Met Ser Met
385                 390                 395                 400

Pro Leu Ser Arg Lys Asp Val Lys Trp
                405

<210> SEQ ID NO 2
<211> LENGTH: 392
<212> TYPE: PRT
<213> ORGANISM: Mycoplasma phocicerebrale

<400> SEQUENCE: 2

Ile His Val Tyr Ser Glu Ile Gly Glu Leu Glu Thr Val Leu Val His
1               5                   10                  15

Glu Pro Gly Arg Glu Ile Asp Tyr Ile Thr Pro Ala Arg Leu Asp Glu
            20                  25                  30

Leu Leu Phe Ser Ala Ile Leu Glu Ser His Asp Ala Arg Lys Glu His
        35                  40                  45

Gln Ser Phe Val Lys Gln Leu Lys Asp Asn Gly Ile Asn Val Val Glu
    50                  55                  60

Leu Thr Asp Leu Val Ala Glu Thr Phe Asp Leu Ala Ser Lys Glu Glu
65                  70                  75                  80
```

Gln Glu Lys Leu Ile Glu Glu Phe Leu Glu Asp Ser Glu Pro Val Leu
                85                  90                  95

Ser Glu Ala His Lys Thr Ala Val Arg Lys Phe Leu Thr Ser Arg Lys
            100                 105                 110

Ser Thr Arg Glu Met Val Glu Phe Met Met Ala Gly Ile Thr Lys Tyr
            115                 120                 125

Asp Leu Gly Ile Glu Ala Asp His Glu Leu Ile Val Asp Pro Met Pro
        130                 135                 140

Asn Leu Tyr Phe Thr Arg Asp Pro Phe Ala Ser Val Gly Asn Gly Val
145                 150                 155                 160

Thr Ile His Tyr Met Arg Tyr Lys Val Arg Gln Arg Glu Thr Leu Phe
                165                 170                 175

Ser Arg Phe Val Phe Ser Asn His Pro Lys Leu Val Lys Thr Pro Trp
            180                 185                 190

Tyr Tyr Asp Pro Ala Met Lys Met Ser Ile Glu Gly Gly Asp Val Phe
        195                 200                 205

Ile Tyr Asn Asn Asp Thr Leu Val Val Gly Val Ser Glu Arg Thr Asp
        210                 215                 220

Leu Glu Thr Ile Thr Leu Leu Ala Lys Asn Ile Lys Ala Asn Lys Glu
225                 230                 235                 240

Val Glu Phe Lys Arg Ile Val Ala Ile Asn Val Pro Lys Trp Thr Asn
                245                 250                 255

Leu Met His Leu Asp Thr Trp Leu Thr Met Leu Asp Lys Asp Lys Phe
            260                 265                 270

Leu Tyr Ser Pro Ile Ala Asn Asp Val Phe Lys Phe Trp Asp Tyr Asp
            275                 280                 285

Leu Val Asn Gly Gly Ala Glu Pro Gln Pro Lys Glu Asn Gly Leu Pro
        290                 295                 300

Leu Glu Gly Leu Leu Gln Ser Ile Ile Asn Lys Lys Pro Val Leu Ile
305                 310                 315                 320

Pro Ile Ala Gly Asn Asn Ala Ser His Ile Asp Ile Glu Arg Glu Thr
                325                 330                 335

His Phe Asp Gly Thr Asn Tyr Leu Ala Ile Lys Pro Gly Val Val Ile
            340                 345                 350

Gly Tyr Ala Arg Asn Glu Lys Thr Asn Ala Ala Leu Ala Ala Ala Gly
            355                 360                 365

Ile Lys Val Leu Pro Phe His Gly Asn Gln Leu Ser Leu Gly Met Gly
        370                 375                 380

Asn Ala Arg Cys Met Ser Met Pro
385                 390

<210> SEQ ID NO 3
<211> LENGTH: 410
<212> TYPE: PRT
<213> ORGANISM: Mycoplasma arginini

<400> SEQUENCE: 3

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Lys Gln Phe Val Ala Glu

```
            50                  55                  60
Leu Lys Ala Asn Asp Ile Asn Val Val Glu Leu Ile Asp Leu Val Ala
 65                  70                  75                  80

Glu Thr Tyr Asp Leu Ala Ser Gln Glu Ala Lys Asp Lys Leu Ile Glu
                 85                  90                  95

Glu Phe Leu Glu Asp Ser Glu Pro Val Leu Ser Glu Glu His Lys Val
                100                 105                 110

Val Val Arg Asn Phe Leu Lys Ala Lys Lys Thr Ser Arg Glu Leu Val
            115                 120                 125

Glu Ile Met Met Ala Gly Ile Thr Lys Tyr Asp Leu Gly Ile Glu Ala
        130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Ile Asn Thr Pro Trp Tyr Tyr Asp Pro Ser Leu
        195                 200                 205

Lys Leu Ser Ile Glu Gly Gly Asp Val Phe Ile Tyr Asn Asn Asp Thr
210                 215                 220

Leu Val Val Gly Val Ser Glu Arg Thr Asp Leu Gln Thr Val Thr Leu
225                 230                 235                 240

Leu Ala Lys Asn Ile Val Ala Asn Lys Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Ala
    290                 295                 300

Glu Pro Gln Pro Val Glu Asn Gly Leu Pro Leu Glu Gly Leu Leu Gln
305                 310                 315                 320

Ser Ile Ile Asn Lys Lys Pro Val Leu Ile Pro Ile Ala Gly Glu Gly
                325                 330                 335

Ala Ser Gln Met Glu Ile Glu Arg Glu Thr His Phe Asp Gly Thr Asn
            340                 345                 350

Tyr Leu Ala Ile Arg Pro Gly Val Val Ile Gly Tyr Ser Arg Asn Glu
        355                 360                 365

Lys Thr Asn Ala Ala Leu Glu Ala Ala Gly Ile Lys Val Leu Pro Phe
    370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 4
<211> LENGTH: 409
<212> TYPE: PRT
<213> ORGANISM: Mycoplasma arthritidis

<400> SEQUENCE: 4

Met Ser Val Phe Asp Ser Lys Phe Lys Gly Ile His Val Tyr Ser Glu
 1               5                  10                  15
```

-continued

```
Ile Gly Glu Leu Glu Thr Val Leu Val His Pro Gly Lys Glu Ile
             20                  25                  30

Asp Tyr Ile Thr Pro Ala Arg Leu Asp Glu Leu Leu Phe Ser Ala Ile
         35                  40                  45

Leu Glu Ser His Asp Ala Arg Lys Glu His Lys Glu Phe Val Ala Glu
     50                  55                  60

Leu Lys Lys Arg Gly Ile Asn Val Val Glu Leu Val Asp Leu Ile Val
 65                  70                  75                  80

Glu Thr Tyr Asp Leu Ala Ser Lys Glu Ala Lys Glu Lys Leu Leu Glu
                 85                  90                  95

Glu Phe Leu Asp Asp Ser Val Pro Val Leu Ser Asp Glu His Arg Ala
            100                 105                 110

Ala Val Lys Lys Phe Leu Gln Ser Gln Lys Ser Thr Arg Ser Leu Val
        115                 120                 125

Glu Tyr Met Ile Ala Gly Ile Thr Lys His Asp Leu Lys Ile Glu Ser
    130                 135                 140

Asp Leu Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Val Asn Thr Pro Trp Tyr Tyr Asp Pro Ala Glu
        195                 200                 205

Gly Leu Ser Ile Glu Gly Gly Asp Val Phe Ile Tyr Asn Asn Asp Thr
    210                 215                 220

Leu Val Val Gly Val Ser Glu Arg Thr Asp Leu Gln Thr Ile Thr Leu
225                 230                 235                 240

Leu Ala Lys Asn Ile Lys Ala Asn Lys Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Asp
    290                 295                 300

Ala Pro Gln Pro Val Asp Asn Gly Leu Pro Leu Glu Asp Leu Leu Lys
305                 310                 315                 320

Ser Ile Ile Gly Lys Lys Pro Thr Leu Ile Pro Ile Ala Gly Ala Gly
                325                 330                 335

Ala Ser Gln Ile Asp Ile Glu Arg Glu Thr His Phe Asp Gly Thr Asn
            340                 345                 350

Tyr Leu Ala Val Ala Pro Gly Ile Val Ile Gly Tyr Ala Arg Asn Glu
        355                 360                 365

Lys Thr Asn Ala Ala Leu Glu Ala Ala Gly Ile Thr Val Leu Pro Phe
    370                 375                 380

Arg Gly Asn Gln Leu Ser Leu Gly Met Gly Asn Ala Arg Cys Met Ser
385                 390                 395                 400

Met Pro Leu Ser Arg Lys Asp Val Lys
                405

<210> SEQ ID NO 5
<211> LENGTH: 408
<212> TYPE: PRT
```

```
<213> ORGANISM: Mycoplasma orale
<220> FEATURE:
<221> NAME/KEY: misc_feature
<222> LOCATION: (201)..(201)
<223> OTHER INFORMATION: Xaa can be any naturally occurring amino acid
<220> FEATURE:
<221> NAME/KEY: misc_feature
<222> LOCATION: (263)..(263)
<223> OTHER INFORMATION: Xaa can be any naturally occurring amino acid
<220> FEATURE:
<221> NAME/KEY: misc_feature
<222> LOCATION: (272)..(272)
<223> OTHER INFORMATION: Xaa can be any naturally occurring amino acid
<220> FEATURE:
<221> NAME/KEY: misc_feature
<222> LOCATION: (294)..(294)
<223> OTHER INFORMATION: Xaa can be any naturally occurring amino acid

<400> SEQUENCE: 5
```

Ser Val Phe Ser Asp Lys Phe Asn Gly Ile His Val Tyr Ser Glu Ile
1               5                   10                  15

Gly Asp Leu Glu Ser Val Leu Val His Glu Pro Gly Lys Glu Ile Asp
            20                  25                  30

Tyr Ile Thr Pro Ala Arg Leu Asp Glu Leu Leu Phe Ser Ala Ile Leu
        35                  40                  45

Glu Ser Thr Asp Ala Arg Lys Glu His Lys Glu Phe Val Glu Ile Leu
    50                  55                  60

Lys Lys Gln Gly Ile Asn Val Val Glu Leu Val Asp Leu Val Val Glu
65                  70                  75                  80

Thr Tyr Asn Leu Val Asp Lys Lys Thr Gln Glu Lys Leu Leu Lys Asp
                85                  90                  95

Phe Leu Asp Asp Ser Glu Pro Val Leu Ser Pro Glu His Arg Lys Ala
            100                 105                 110

Val Glu Lys Phe Leu Lys Ser Leu Lys Ser Thr Lys Glu Leu Ile Gln
        115                 120                 125

Tyr Met Met Ala Gly Ile Thr Lys Tyr Asp Leu Gly Ile Lys Ala Asp
    130                 135                 140

Lys Glu Leu Ile Val Asp Pro Met Pro Asn Leu Tyr Phe Thr Arg Asp
145                 150                 155                 160

Pro Phe Ala Ser Val Gly Asn Gly Val Thr Ile His Tyr Met Arg Tyr
                165                 170                 175

Lys Val Arg Gln Arg Glu Thr Leu Phe Ser Lys Phe Ile Phe Thr Asn
            180                 185                 190

His Pro Lys Leu Val Lys Thr Pro Xaa Tyr Tyr Asp Pro Ala Met Lys
        195                 200                 205

Leu Ser Ile Glu Gly Gly Asp Val Phe Ile Tyr Asn Asn Asp Thr Leu
    210                 215                 220

Val Val Gly Val Ser Glu Arg Thr Asp Leu Glu Thr Ile Thr Leu Leu
225                 230                 235                 240

Ala Lys Asn Ile Lys Ala Asn Lys Glu Cys Glu Phe Lys Arg Ile Val
                245                 250                 255

Ala Ile Asn Val Pro Lys Xaa Thr Asn Leu Met His Leu Asp Thr Xaa
            260                 265                 270

Leu Thr Met Leu Asp Lys Asp Lys Phe Leu Tyr Ser Pro Ile Ala Asn
        275                 280                 285

Asp Val Phe Lys Phe Xaa Asp Tyr Asp Leu Val Asn Gly Gly Ser Asn
    290                 295                 300

Pro Glu Pro Val Val Asn Gly Leu Pro Leu Asp Lys Leu Leu Glu Ser
305                 310                 315                 320

```
Ile Ile Asn Lys Lys Pro Val Leu Ile Pro Ile Ala Gly Lys Gly Ala
            325                 330                 335

Thr Glu Ile Glu Thr Ala Val Glu Thr His Phe Asp Gly Thr Asn Tyr
        340                 345                 350

Leu Ala Ile Lys Pro Gly Val Val Val Gly Tyr Ser Arg Asn Val Lys
            355                 360                 365

Thr Asn Ala Ala Leu Glu Ala Asn Gly Ile Lys Val Leu Pro Phe Lys
        370                 375                 380

Gly Asn Gln Leu Ser Leu Gly Met Gly Asn Ala Arg Cys Met Ser Met
385                 390                 395                 400

Pro Leu Ser Arg Lys Asp Val Lys
            405

<210> SEQ ID NO 6
<211> LENGTH: 391
<212> TYPE: PRT
<213> ORGANISM: Mycoplasma gateae

<400> SEQUENCE: 6

Ile His Val Tyr Ser Glu Ile Gly Glu Leu Glu Ser Val Leu Val His
1               5                   10                  15

Glu Pro Gly Arg Glu Ile Asp Tyr Ile Thr Pro Ala Arg Leu Asp Glu
            20                  25                  30

Leu Leu Phe Ser Ala Ile Leu Glu Ser His Asp Ala Arg Lys Glu His
        35                  40                  45

Lys Leu Phe Val Ser Glu Leu Lys Ala Asn Asp Ile Asn Val Val Glu
    50                  55                  60

Leu Thr Asp Leu Val Thr Glu Thr Tyr Asp Leu Ala Ser Gln Glu Ala
65                  70                  75                  80

Lys Asp Asn Leu Ile Glu Glu Phe Leu Glu Asp Ser Glu Pro Val Leu
                85                  90                  95

Thr Glu Glu Leu Lys Ser Val Val Arg Thr Tyr Leu Lys Ser Ile Lys
            100                 105                 110

Ser Thr Arg Glu Leu Ile Gln Met Met Met Ala Gly Ile Thr Lys Tyr
        115                 120                 125

Asp Leu Gly Ile Glu Ala Asp His Glu Leu Ile Val Asp Pro Met Pro
    130                 135                 140

Asn Leu Tyr Phe Thr Arg Asp Pro Phe Ala Ser Val Gly Asn Gly Val
145                 150                 155                 160

Thr Ile His Tyr Met Arg Tyr Lys Val Arg Gln Arg Glu Thr Leu Phe
                165                 170                 175

Ser Arg Phe Val Phe Ser Asn His Pro Lys Leu Val Asn Thr Pro Trp
            180                 185                 190

Tyr Tyr Asp Pro Ser Leu Lys Leu Ser Ile Glu Gly Gly Asp Val Phe
        195                 200                 205

Ile Tyr Asn Asn Asn Thr Leu Val Val Gly Val Ser Glu Arg Thr Asp
    210                 215                 220

Leu Glu Thr Val Thr Leu Leu Ala Lys Asn Ile Val Ala Asn Lys Glu
225                 230                 235                 240

Cys Glu Phe Lys Arg Ile Val Ala Ile Asn Val Pro Lys Trp Thr Asn
                245                 250                 255

Leu Met His Leu Asp Thr Trp Leu Thr Met Leu Asp Lys Asp Lys Phe
            260                 265                 270

Leu Tyr Ser Pro Ile Ala Asn Asp Val Phe Lys Phe Trp Asp Tyr Asp
```

```
            275                 280                 285
Leu Val Asn Gly Gly Glu Glu Pro Gln Pro Val Glu Asn Gly Leu Pro
    290                 295                 300

Leu Glu Gly Leu Leu Glu Ser Ile Ile Asn Lys Lys Pro Ile Leu Ile
305                 310                 315                 320

Pro Ile Ala Gly Glu Gly Ala Ser Gln Ile Asp Ile Glu Arg Glu Thr
                325                 330                 335

His Phe Asp Gly Thr Asn Tyr Leu Ala Ile Arg Pro Gly Val Val Ile
            340                 345                 350

Gly Tyr Ser Arg Asn Glu Lys Thr Asn Ala Ala Leu Glu Ala Ala Gly
        355                 360                 365

Ile Lys Val Leu Pro Phe His Gly Asn Gln Leu Ser Leu Gly Met Gly
370                 375                 380

Asn Ala Arg Cys Met Ser Met
385                 390

<210> SEQ ID NO 7
<211> LENGTH: 392
<212> TYPE: PRT
<213> ORGANISM: Mycoplasma phocidae

<400> SEQUENCE: 7

Ile His Val Tyr Ser Glu Ile Gly Glu Leu Gln Thr Val Leu Val His
1               5                   10                  15

Glu Pro Gly Arg Glu Ile Glu Tyr Ile Thr Pro Ala Arg Leu Asp Glu
                20                  25                  30

Leu Leu Phe Ser Ala Ile Leu Glu Ser His Asp Ala Arg Lys Glu His
            35                  40                  45

Gln Glu Phe Val Ala Glu Leu Lys Lys Asn Asn Ile Asn Val Val Glu
        50                  55                  60

Leu Thr Asp Leu Val Ser Glu Thr Tyr Asp Met Val Ser Lys Glu Lys
65                  70                  75                  80

Gln Glu Lys Leu Ile Glu Glu Phe Leu Glu Asp Ser Glu Pro Val Leu
                85                  90                  95

Ser Glu Glu His Lys Gly Leu Val Arg Lys Phe Leu Lys Ser Leu Lys
            100                 105                 110

Ser Ser Lys Glu Leu Ile Gln Tyr Met Met Ala Gly Ile Thr Lys His
        115                 120                 125

Asp Leu Asn Ile Glu Ala Asp His Glu Leu Ile Val Asp Pro Met Pro
    130                 135                 140

Asn Leu Tyr Phe Thr Arg Asp Pro Phe Ala Ser Val Gly Asn Gly Val
145                 150                 155                 160

Thr Ile His Tyr Met Arg Tyr Lys Val Arg Gln Arg Glu Thr Leu Phe
                165                 170                 175

Ser Arg Phe Ile Phe Ala Asn His Pro Lys Leu Met Asn Thr Pro Leu
            180                 185                 190

Tyr Tyr Asn Pro Asp Met Lys Leu Ser Ile Glu Gly Gly Asp Val Phe
        195                 200                 205

Val Tyr Asn Asn Glu Thr Leu Val Val Gly Val Ser Glu Arg Thr Asp
    210                 215                 220

Leu Asp Thr Ile Thr Leu Leu Ala Lys Asn Ile Lys Ala Asn Lys Glu
225                 230                 235                 240

Arg Glu Phe Lys Arg Ile Val Ala Ile Asn Val Pro Lys Trp Thr Asn
                245                 250                 255
```

-continued

```
Leu Met His Leu Asp Thr Trp Leu Thr Met Leu Asp Lys Asp Lys Phe
            260                 265                 270

Leu Tyr Ser Pro Ile Ala Asn Asp Val Phe Lys Phe Trp Asp Tyr Asp
        275                 280                 285

Leu Val Asn Gly Gly Asp Glu Pro Gln Pro Lys Val Asn Gly Leu Pro
    290                 295                 300

Leu Glu Lys Leu Leu Glu Ser Ile Ile Asn Lys Lys Pro Ile Leu Ile
305                 310                 315                 320

Pro Ile Ala Gly Thr Ser Ala Ser Asn Ile Asp Val Glu Arg Glu Thr
                325                 330                 335

His Phe Asp Gly Thr Asn Tyr Leu Ala Ile Ala Pro Gly Val Val Ile
            340                 345                 350

Gly Tyr Ser Arg Asn Val Lys Thr Asn Glu Ala Leu Glu Ala Ala Gly
        355                 360                 365

Ile Lys Val Leu Pro Phe Lys Gly Asn Gln Leu Ser Leu Gly Met Gly
    370                 375                 380

Asn Ala Arg Cys Met Ser Met Pro
385                 390

<210> SEQ ID NO 8
<211> LENGTH: 401
<212> TYPE: PRT
<213> ORGANISM: Mycoplasma columbinum

<400> SEQUENCE: 8

Met Ser Lys Ile Asn Val Tyr Ser Glu Ile Gly Glu Leu Lys Glu Val
1

```
Lys Asn Asn Lys Glu Ala Lys Phe Lys Ile Val Ala Ile Asn Val
                245                 250                 255

Pro Pro Met Pro Asn Leu Met His Leu Asp Thr Trp Leu Thr Met Val
        260                 265                 270

Asp Lys Asp Lys Phe Leu Tyr Ser Pro Asn Met Leu Ser Val Leu Lys
            275                 280                 285

Val Trp Glu Ile Asp Leu Ser Lys Glu Ile Glu Met Val Glu Thr Asn
290                 295                 300

Lys Pro Leu Ala Asp Val Leu Glu Ser Ile Ile Gly Val Lys Pro Val
305                 310                 315                 320

Leu Ile Pro Ile Ala Gly Lys Gly Ala Thr Gln Leu Asp Ile Asp Ile
                325                 330                 335

Glu Thr His Phe Asp Gly Thr Asn Tyr Leu Thr Ile Ala Pro Gly Val
            340                 345                 350

Val Val Gly Tyr Ser Arg Asn Ile Lys Thr Glu Ala Ala Leu Arg Ala
        355                 360                 365

Ala Gly Val Thr Val Leu Ser Phe Glu Gly Asn Gln Leu Ser Leu Gly
    370                 375                 380

Met Gly Ser Ala Arg Cys Met Ser Met Pro Leu Val Arg Glu Asp Val
385                 390                 395                 400

Lys

<210> SEQ ID NO 9
<211> LENGTH: 407
<212> TYPE: PRT
<213> ORGANISM: Mycoplasma iowae

<400> SEQUENCE: 9

Met Gly Asn Asn Ile Pro Lys Lys Ile Asn Val Phe Ser Glu Ile Gly
1               5                   10                  15

Asn Leu Lys Arg Val Leu Val His Thr Pro Gly Lys Glu Ile Glu Tyr
            20                  25                  30

Val Thr Pro Gln Arg Leu Asp Glu Leu Leu Phe Ser Ala Ile Leu Asp
        35                  40                  45

Pro Val Arg Ala Arg Glu Glu His Lys Glu Phe Ile Lys Ile Leu Glu
    50                  55                  60

Ser Gln Gly Val Glu Val Val Gln Leu Val Asp Leu Thr Ala Glu Thr
65                  70                  75                  80

Tyr Asp Val Ala Glu Ser Gln Ala Lys Glu Asn Phe Ile Gln Lys Trp
                85                  90                  95

Leu Asp Glu Ser Leu Pro Lys Leu Thr Asp Glu Asn Arg Asn Lys Val
            100                 105                 110

Tyr Ser Leu Leu Lys Ser Leu Glu Lys Asp Pro Lys Glu Met Ile Arg
        115                 120                 125

Lys Met Met Ser Gly Val Leu Ala Ser Glu Ile Gly Val Lys Ser Asp
    130                 135                 140

Val Glu Leu Ile Val Asp Pro Met Pro Asn Leu Tyr Phe Thr Arg Asp
145                 150                 155                 160

Pro Phe Ala Ser Val Gly Asn Gly Ile Thr Leu His Arg Met Phe Arg
                165                 170                 175

Pro Thr Arg Arg Arg Glu Thr Ile Phe Ala Asp Phe Ile Phe Ser Asn
            180                 185                 190

His Pro Glu Tyr Lys Ser Thr Gln Lys Tyr Tyr Glu Arg Glu Asp Lys
        195                 200                 205
```

```
Phe Ser Leu Glu Gly Gly Asp Val Phe Ile Tyr Asn Asn Lys Thr Leu
    210                 215                 220

Val Val Gly Val Ser Glu Arg Thr Glu Lys Gly Ala Ile Lys Ala Leu
225                 230                 235                 240

Ala Lys Ala Val Gln Asn Asn Ser Asn Met Ser Phe Glu Lys Ile Tyr
                245                 250                 255

Ala Ile Asn Val Pro Lys Met Ser Asn Leu Met His Leu Asp Thr Trp
                260                 265                 270

Leu Thr Met Leu Asp Thr Asp Lys Phe Leu Tyr Ser Pro Asn Met Met
            275                 280                 285

Gly Val Leu Lys Ile Trp Glu Ile Asp Leu Ser Asp Lys Ser Leu Lys
    290                 295                 300

Trp Lys Glu Ile Arg Asp Ser Leu Asp His Phe Leu Ser Thr Ile Ile
305                 310                 315                 320

Gly Lys Lys Ala Ile Thr Val Pro Val Ala Gly Lys Asp Ala Met Gln
                325                 330                 335

Phe Glu Ile Asp Ile Glu Thr His Phe Asp Ala Thr Asn Phe Ile Ala
                340                 345                 350

Val Ala Pro Gly Val Val Ile Gly Tyr Asp Arg Asn Lys Lys Thr Asn
            355                 360                 365

Glu Ala Leu Lys Glu Ala Gly Ile Lys Val Leu Ser Trp Asn Gly Asp
    370                 375                 380

Gln Leu Ser Leu Gly Met Gly Ser Ala Arg Cys Met Thr Met Pro Leu
385                 390                 395                 400

Tyr Arg Glu Glu Leu Lys Lys
                405

<210> SEQ ID NO 10
<211> LENGTH: 402
<212> TYPE: PRT
<213> ORGANISM: Mycoplasma crocodyli

<400> SEQUENCE: 10

Met Asn Lys Ile Asn Val Tyr Ser Glu Val Gly Lys Leu Lys Glu Val
1               5                   10                  15

Leu Val His Thr Pro Gly Asp Glu Ile Arg Arg Ile Ser Pro Ser Arg
            20                  25                  30

Leu Glu Glu Leu Leu Phe Ser Ala Ile Leu Glu Pro Asp Ser Ala Ile
        35                  40                  45

Glu Glu His Lys Arg Phe Leu Lys Ile Leu Glu Asp Asn Asn Ile Lys
    50                  55                  60

Val Ile Gln Leu Asp Gln Leu Val Ala Asp Thr Tyr Glu Leu Val Asn
65                  70                  75                  80

Pro Ser Val Arg Asp Ala Phe Ile Glu Lys Trp Leu Asn Glu Ser Glu
                85                  90                  95

Pro Lys Leu Asp Lys Lys Leu Arg Glu Lys Val Lys Glu Tyr Leu Leu
            100                 105                 110

His Thr Gln Lys Thr Val Gly Thr Lys Arg Met Val Arg Ile Met Met
        115                 120                 125

Ala Gly Val Asp Arg Val Glu Leu Gly Val Glu Leu Asp Arg Gln Leu
    130                 135                 140

Val Val Asp Pro Met Pro Asn Leu Tyr Phe Thr Arg Asp Pro Phe Ala
145                 150                 155                 160

Ser Ala Gly Asn Gly Ile Ser Leu Asn Asn Met Lys Tyr Val Thr Arg
```

```
                165                 170                 175
Lys Arg Glu Thr Ile Phe Ser Glu Phe Ile Phe Glu Asn His Pro Asp
            180                 185                 190

Tyr Lys Thr Thr Pro His Trp Phe Asp Arg Leu Asp Lys Gly Asn Ile
        195                 200                 205

Glu Gly Gly Asp Val Phe Ile Tyr Asn Arg Thr Thr Leu Val Ile Gly
    210                 215                 220

Ile Ser Glu Arg Thr Asn Lys Asp Ala Leu Leu Thr Ile Ala Asn Asn
225                 230                 235                 240

Ile Lys Ser Asn Lys Glu Ser Lys Phe Glu Arg Ile Val Ala Val Asn
                245                 250                 255

Val Pro Pro Met Pro Asn Leu Met His Leu Asp Thr Trp Leu Thr Met
            260                 265                 270

Val Asp His Asp Lys Phe Leu Tyr Ser Pro Asn Met Met Lys Thr Leu
        275                 280                 285

Lys Phe Trp Thr Ile Asp Leu Thr Lys Pro Ile Lys Met Val Glu Leu
    290                 295                 300

Glu Glu Ser Leu Ser Asp Met Ile Glu Thr Ile Ile Gly Lys Lys Pro
305                 310                 315                 320

Val Leu Ile Pro Ile Ala Gly His Asp Ala Ser Pro Leu Asp Val Asp
                325                 330                 335

Ile Glu Thr His Phe Asp Gly Thr Asn Tyr Leu Thr Ile Ala Pro Gly
            340                 345                 350

Val Val Val Gly Tyr Ser Arg Asn Lys Leu Thr Glu Lys Ala Leu Thr
        355                 360                 365

Lys Ala Gly Val Lys Val Leu Ser Phe Glu Gly Asn Gln Leu Ser Leu
    370                 375                 380

Gly Met Gly Ser Ala Arg Cys Met Ser Met Pro Leu Val Arg Glu Asp
385                 390                 395                 400

Ile Lys

<210> SEQ ID NO 11
<211> LENGTH: 430
<212> TYPE: PRT
<213> ORGANISM: Mycoplasma fermentans

<400> SEQUENCE: 11

Met Gln Ile Ile Ala Lys Ile Asp Leu Leu Thr Asn Met Leu Ile Phe
1               5                   10                  15

Met Lys Ile Tyr Phe Ile Gly Arg Leu Ile Met Lys Lys Ile Asn Val
            20                  25                  30

Tyr Ser Glu Tyr Gly Lys Leu Lys Glu Val Leu Val His Thr Pro Gly
        35                  40                  45

Asp Glu Ile Arg Arg Ile Ala Pro Ser Arg Leu Asp Glu Leu Leu Phe
    50                  55                  60

Ser Ala Ile Leu Glu Pro Asp Ser Ala Ile Ala Glu His Lys Arg Phe
65                  70                  75                  80

Val Gln Leu Leu Lys Asp Asn Gly Ile Lys Val Ile Gln Leu Asp Glu
                85                  90                  95

Leu Phe Ala Lys Thr Phe Asp Leu Val Ser Glu Ser Val Lys Gln Ser
            100                 105                 110

Leu Ile Glu Arg Trp Leu Asp Glu Cys Glu Pro Lys Leu Asp Ala Thr
        115                 120                 125

Leu Arg Ala Lys Val Lys Glu Tyr Ile Leu Glu Leu Lys Ala Lys Ser
```

```
            130                 135                 140
Ser Lys Lys Met Val Arg Val Met Ala Gly Ile Asp Lys Lys Glu
145                 150                 155                 160

Leu Gly Ile Glu Leu Asp Arg Asp Leu Val Val Asp Pro Met Pro Asn
                165                 170                 175

Leu Tyr Phe Thr Arg Asp Pro Phe Ala Ser Val Gly Asn Gly Ile Ser
                180                 185                 190

Leu His His Met Lys Tyr Val Thr Arg Gln Arg Glu Thr Ile Phe Ser
                195                 200                 205

Glu Phe Ile Phe Asp Asn Asn Leu Asp Tyr Asn Thr Val Pro Arg Trp
                210                 215                 220

Phe Asp Arg Lys Asp Glu Gly Arg Ile Glu Gly Asp Val Phe Ile
225                 230                 235                 240

Tyr Ser Ala Asp Thr Leu Val Val Gly Val Ser Glu Arg Thr Asn Lys
                245                 250                 255

Glu Ala Ile Asn Val Met Ala Arg Lys Ile Ala Ala Asp Lys Glu Val
                260                 265                 270

Lys Phe Lys Arg Ile Tyr Ala Ile Asn Val Pro Pro Met Pro Asn Leu
                275                 280                 285

Met His Leu Asp Thr Trp Leu Thr Met Leu Asp Lys Asn Lys Phe Leu
                290                 295                 300

Tyr Ser Pro Asn Met Leu Ser Val Leu Lys Val Trp Arg Ile Asp Leu
305                 310                 315                 320

Asn Asp Pro Asp Phe Val Trp His Glu Ile Glu Gly Ser Leu Glu Glu
                325                 330                 335

Ile Leu Glu Gln Ile Ile Gly Met Lys Pro Ile Leu Ile Pro Ile Ala
                340                 345                 350

Gly Lys Gly Ala Ser Gln Leu Asp Ile Asp Ile Glu Thr His Phe Asp
                355                 360                 365

Gly Thr Asn Tyr Leu Thr Ile Ala Pro Ser Val Val Gly Tyr Ser
                370                 375                 380

Arg Asn Glu Lys Thr Glu Lys Ala Leu Lys Ala Ala Lys Val Lys Val
385                 390                 395                 400

Leu Ser Phe Glu Gly Asn Gln Leu Ser Leu Gly Met Gly Ser Ala Arg
                405                 410                 415

Cys Met Ser Met Pro Leu Ile Arg Glu Asp Ile Lys Lys Lys
                420                 425                 430

<210> SEQ ID NO 12
<211> LENGTH: 452
<212> TYPE: PRT
<213> ORGANISM: Mycoplasma penetrans

<400> SEQUENCE: 12

Met Val Ile Thr Ile Ala Leu Asn Ile Leu Asn Lys Ile Tyr Phe Lys
1               5                   10                  15

Pro Gln Asn Arg Ser Ile Leu Lys Leu Tyr Arg Leu Pro Ser Leu Cys
                20                  25                  30

Thr Gln Ile Ser Ile Phe Ile Gly Gly Lys Met Ser Ser Ile Asp Lys
                35                  40                  45

Asn Ser Leu Gly Asn Gly Ile Asn Val Tyr Ser Glu Ile Gly Glu Leu
                50                  55                  60

Lys Glu Val Leu Val His Thr Pro Gly Asp Glu Ile Arg Tyr Thr Ala
65                  70                  75                  80
```

```
Pro Ser Arg Leu Glu Glu Leu Leu Phe Ser Ala Val Leu Lys Ala Asp
                85                  90                  95

Thr Ala Ile Glu Glu His Lys Gly Phe Val Lys Ile Leu Gln Asn Asn
            100                 105                 110

Gly Ile Lys Val Ile Gln Leu Cys Asp Leu Val Ala Glu Thr Tyr Glu
        115                 120                 125

Leu Cys Ser Lys Glu Val Arg Asn Ser Phe Ile Glu Gln Tyr Leu Asp
    130                 135                 140

Glu Ala Leu Pro Val Leu Lys Lys Glu Ile Arg Pro Val Val Lys Asp
145                 150                 155                 160

Tyr Leu Leu Ser Phe Pro Thr Val Gln Met Val Arg Lys Met Met Ser
                165                 170                 175

Gly Ile Leu Ala Asn Glu Leu Asn Ile Lys Gln Asp Asn Pro Leu Ile
            180                 185                 190

Ile Asp Gly Met Pro Asn Leu Tyr Phe Thr Arg Asp Pro Phe Ala Ser
        195                 200                 205

Met Gly Asn Gly Val Ser Ile Asn Cys Met Lys Tyr Pro Thr Arg Lys
    210                 215                 220

Arg Glu Val Ile Phe Ser Arg Phe Val Phe Thr Asn Asn Pro Lys Tyr
225                 230                 235                 240

Lys Asn Thr Pro Arg Tyr Phe Asp Ile Val Gly Asn Asn Gly Thr Ile
                245                 250                 255

Glu Gly Gly Asp Ile Phe Ile Tyr Asn Ser Lys Thr Leu Val Ile Gly
            260                 265                 270

Asn Ser Glu Arg Thr Asn Phe Ala Ala Ile Glu Ser Val Ala Lys Asn
        275                 280                 285

Ile Gln Ala Asn Lys Asp Cys Thr Phe Glu Arg Ile Val Val Ile Asn
    290                 295                 300

Val Pro Pro Met Pro Asn Leu Met His Leu Asp Thr Trp Leu Thr Met
305                 310                 315                 320

Leu Asp Tyr Asp Lys Phe Leu Tyr Ser Pro Asn Met Met Asn Val Leu
                325                 330                 335

Lys Ile Trp Glu Ile Asp Leu Asn Val Lys Pro Val Lys Phe Val Glu
            340                 345                 350

Lys Lys Gly Thr Leu Glu Glu Val Leu Tyr Ser Ile Ile Asp Lys Lys
        355                 360                 365

Pro Ile Leu Ile Pro Ile Ala Gly Lys Gly Ala Asn Gln Leu Asp Ile
    370                 375                 380

Asp Ile Glu Thr His Phe Asp Gly Thr Asn Tyr Leu Thr Ile Ala Pro
385                 390                 395                 400

Gly Val Val Val Gly Tyr Glu Arg Asn Glu Lys Thr Gln Lys Ala Leu
                405                 410                 415

Val Glu Ala Gly Ile Lys Val Leu Ser Phe Asn Gly Ser Gln Leu Ser
            420                 425                 430

Leu Gly Met Gly Ser Ala Arg Cys Met Ser Met Pro Leu Ile Arg Glu
        435                 440                 445

Asn Leu Lys Lys
    450

<210> SEQ ID NO 13
<211> LENGTH: 408
<212> TYPE: PRT
<213> ORGANISM: Mycoplasma gallisepticum

<400> SEQUENCE: 13
```

```
Met Arg Arg Lys Phe Met Phe Asn Lys Ile Arg Val Tyr Ser Glu Ile
1               5                   10                  15

Gly Lys Leu Arg Lys Val Leu Val His Thr Pro Gly Lys Glu Leu Asp
            20                  25                  30

Tyr Val Thr Pro Gln Arg Leu Asp Glu Leu Leu Phe Ser Ser Leu Leu
        35                  40                  45

Asn Pro Ile Lys Ala Arg Gln Glu His Glu Thr Phe Ile Lys Leu Leu
    50                  55                  60

Glu Asp His Asp Val Glu Cys Val Gln Leu Ser Thr Leu Thr Ala Gln
65                  70                  75                  80

Thr Phe Gln Ala Val Asn Ser Lys Ile Gln Glu Glu Phe Ile Asn Arg
            85                  90                  95

Trp Leu Asp Glu Cys Leu Pro Val Leu Ser Glu Ile Asn Arg Leu Lys
        100                 105                 110

Val Tyr Asp Tyr Leu Lys Ser Leu Ala Thr Asn Pro Gln Val Met Ile
    115                 120                 125

Arg Lys Met Met Ser Gly Ile Leu Ala Lys Glu Val Gly Ile Gln Ser
        130                 135                 140

Glu Val Glu Leu Val Ala Asp Pro Met Pro Asn Leu Tyr Phe Thr Arg
145                 150                 155                 160

Asp Pro Phe Ala Ser Ile Gly Lys Gly Ile Thr Leu His Ser Met Phe
            165                 170                 175

His Pro Thr Arg Lys Arg Glu Thr Ile Phe Ala Asp Phe Ile Phe Ser
        180                 185                 190

His His Pro Glu Tyr Lys Asn Ala Pro Lys Tyr Tyr Ser Arg Glu Asp
    195                 200                 205

Lys Tyr Ser Ile Glu Gly Gly Asp Leu Phe Val Tyr Asp Lys Thr
    210                 215                 220

Leu Val Ile Gly Val Ser Glu Arg Thr Glu Lys Lys Ala Ile Gln Ser
225                 230                 235                 240

Leu Ala Glu Lys Leu Arg Gln Asn Asp Glu Thr Ser Phe Glu Lys Ile
            245                 250                 255

Tyr Ala Ile Asn Val Pro Lys Met Ser Asn Leu Met His Leu Asp Thr
        260                 265                 270

Trp Leu Thr Met Leu Asp Tyr Asp Lys Phe Leu Tyr Ser Pro Asn Met
    275                 280                 285

Met Gly Val Leu Lys Ile Trp Glu Ile Asp Leu Ile His Pro Thr Leu
        290                 295                 300

Ile Trp Arg Glu Leu Asn Glu Ser Leu Glu Gly Phe Leu Ser Met Val
305                 310                 315                 320

Ile Gly Lys Lys Ala Thr Leu Ile Pro Val Ala Gly Glu Asp Ser Thr
            325                 330                 335

Gln Ile Glu Ile Asp Val Glu Thr Asn Phe Asp Ala Thr Asn Phe Leu
        340                 345                 350

Val Ile Gln Pro Gly Val Val Gly Tyr Asp Arg Asn Tyr Lys Thr
    355                 360                 365

Asn Gln Ala Leu Arg Asp Ala Gly Val Lys Val Ile Ser Trp Asn Gly
    370                 375                 380

Asp Gln Leu Ser Leu Gly Met Gly Ser Ala Arg Cys Met Ser Met Pro
385                 390                 395                 400

Leu Tyr Arg Asp Pro Ile Lys Lys
                405
```

<210> SEQ ID NO 14
<211> LENGTH: 402
<212> TYPE: PRT
<213> ORGANISM: Mycoplasma alligatoris

<400> SEQUENCE: 14

```
Met Ser Lys Ile Asn Val Tyr Ser Glu Val Gly Arg Leu Lys Glu Val
1               5                   10                  15

Leu Val His Thr Pro Gly Asp Glu Ile Arg Arg Ile Ser Pro Thr Arg
            20                  25                  30

Leu Glu Glu Leu Leu Phe Ser Ala Ile Leu Glu Pro Asp Thr Ala Ile
        35                  40                  45

Glu Glu His Lys Arg Phe Leu Asn Val Leu Glu Lys Asn Gly Ile Lys
    50                  55                  60

Ala Ile Gln Leu Asp Glu Leu Val Ala Gln Thr Tyr Asp Gln Val Asp
65                  70                  75                  80

Gln Lys Ile Lys Asp Glu Phe Ile Asp Gln Trp Leu Gln Glu Ala Lys
                85                  90                  95

Pro Val Leu Asn Asp Gln Leu Lys Lys Leu Val Lys Asn Tyr Leu Leu
            100                 105                 110

Lys Ser Gln Lys Glu Phe Ser Thr Lys Lys Met Val Arg Ile Met Met
        115                 120                 125

Ala Gly Ile Asp Lys Lys Glu Ile Asn Ile Asp Leu Asp Arg Asp Leu
    130                 135                 140

Val Val Asp Pro Met Pro Asn Leu Tyr Phe Thr Arg Asp Pro Phe Ala
145                 150                 155                 160

Ser Val Gly Asn Gly Ile Ser Leu His Asn Met Lys Tyr Gln Thr Arg
                165                 170                 175

Lys Arg Glu Thr Ile Phe Ala Gln Phe Ile Phe Lys Tyr Asn Lys Asp
            180                 185                 190

Tyr Lys Thr Thr Pro His Trp Phe Asp Arg Phe Asp His Gly Ser Ile
        195                 200                 205

Glu Gly Gly Asp Val Phe Val Tyr Thr Lys Asp Thr Leu Val Ile Gly
    210                 215                 220

Ile Ser Glu Arg Thr Thr Lys Glu Ala Val Leu Asn Ile Ala Lys Lys
225                 230                 235                 240

Ile Lys Ala Asn Thr Asp Ser Lys Phe Lys Lys Ile Val Ala Ile Asn
                245                 250                 255

Val Pro Pro Met Pro Asn Leu Met His Leu Asp Thr Trp Ile Thr Met
            260                 265                 270

Val Asp His Asp Lys Phe Leu Tyr Ser Pro Asn Met Met Lys Ser Leu
        275                 280                 285

Lys Phe Trp Leu Ile Asp Leu Ser Lys Glu Ile Lys Met Val Glu Leu
    290                 295                 300

Glu Glu Ser Leu Ser Asn Met Leu Glu Ala Ile Ile Gly Lys Lys Pro
305                 310                 315                 320

Ile Leu Ile Pro Ile Ala Gly Lys Asn Ala Ser Gln Leu Asp Ile Asp
                325                 330                 335

Ile Glu Thr His Phe Asp Gly Thr Asn Tyr Leu Thr Ile Ala Pro Gly
            340                 345                 350

Val Val Val Gly Tyr Ser Arg Asn Lys Leu Thr Gln Lys Ala Leu Glu
        355                 360                 365

Asp Ala Gly Val Lys Val Leu Ser Phe Asp Gly Asn Gln Leu Ser Leu
    370                 375                 380
```

Gly Met Gly Ser Ala Arg Cys Met Ser Met Pro Leu Val Arg Glu Asp
385                 390                 395                 400

Ile Lys

<210> SEQ ID NO 15
<211> LENGTH: 438
<212> TYPE: PRT
<213> ORGANISM: Mycoplasma pneumoniae

<400> SEQUENCE: 15

Met Ser Lys Lys Gln Leu Val Lys Thr Asp Gly His Asn Gln Leu Asp
1               5                   10                  15

Gln Pro Asn Thr Lys Ala Leu Gln Leu Lys Lys Gln Phe Asn Ser
            20                  25                  30

Gly Val Arg Val Thr Ser Glu Ile Ser Phe Leu Arg Glu Val Ile Ala
            35                  40                  45

His His Pro Gly Ile Glu Thr Glu Arg Val Ile Asp Asn Gln Thr Phe
        50                  55                  60

Gly Ser Ala Met Tyr Leu Glu Arg Ala Gln Lys Glu His Gln Leu Phe
65                  70                  75                  80

Ile Lys Ile Leu Arg Gln His Gly Thr Lys Val His Tyr Leu Gln Asp
                85                  90                  95

Leu Leu Glu Ala Leu Ser Ala Ala Asp Pro Asn Val Arg Gln Asp
            100                 105                 110

Phe Ile Lys Asn Phe Leu Leu Glu Ser Gly Ile Lys Ser Val Ser Thr
            115                 120                 125

Phe Glu Ala Cys Leu Asn Phe Phe Arg Ser Leu Asp Ser Leu Val Asp
        130                 135                 140

Val Ile Lys Val Met Phe Gly Gly Ile Lys Val Ser Asp Val Pro Pro
145                 150                 155                 160

Ile Thr Pro Gln Arg Phe Ala Asp Ile His Val Ser Asn Ser Pro Phe
                165                 170                 175

Leu Ile Lys Pro Leu Ser Phe Ser Leu Tyr Pro His Lys Phe Phe Asn
            180                 185                 190

Thr Leu Gly Thr Gly Val Ala Leu Phe Val Thr Asn Asp Ser Glu Leu
        195                 200                 205

Lys Arg His Ser Leu Val Tyr Glu Tyr Ile Met Arg Phe His Pro Arg
210                 215                 220

Phe Asp Gly Val Lys Leu Tyr Thr Asn Arg Asp Phe Lys Asn Cys Leu
225                 230                 235                 240

Ile Asn Ser Ser Asp Ile Ile Gln Ile Ser Asn Glu Ile Leu Leu Ile
                245                 250                 255

Gly Ile Ser His Asp Thr Asp Val Leu Gly Ile Glu Ser Leu Ala Arg
            260                 265                 270

Asn Leu Leu Ser Asp His Thr Asn Pro Ile Lys Gln Ile Ile Ala Ile
        275                 280                 285

Asn Ile His Lys Phe Gly Ala Lys Thr Asn Leu Asn Lys Leu Ile Ala
    290                 295                 300

Met Val Asp Val Asp Lys Phe Ile Ile Ala Arg Lys Val Leu Gln Ala
305                 310                 315                 320

Thr Glu Ile Phe Glu Leu Thr Ala Thr Ala Gln Arg Asp Val Asp Gly
                325                 330                 335

Leu Ala Gln Ile Lys Phe Lys Pro Leu Lys Phe Asn Phe Gly Glu Ile
            340                 345                 350

Ile Glu Ala Ile Ile Asp Lys Gln Pro Arg Phe Val Ile Gly Gly
                355                 360                 365

Gly Asp Glu Val Ala Glu Arg Lys Glu Leu Leu Asp Cys Gly Met Gly
370                 375                 380

Val Leu Asn Leu Ser Pro Gly Glu Ile Val Val Phe Asp Arg Asn His
385                 390                 395                 400

Tyr Thr Asn Asn Leu Leu Asn Glu Leu Gly Leu Ile Ile His Lys Ile
                405                 410                 415

Pro Ala Ser Glu Leu Ser Arg Gly Pro Ser Gly Pro Leu Glu Met Val
                420                 425                 430

Cys Ser Leu Trp Arg Glu
                435

<210> SEQ ID NO 16
<211> LENGTH: 409
<212> TYPE: PRT
<213> ORGANISM: Mycoplasma mobile

<400> SEQUENCE: 16

Met Lys Asp Thr Lys Asp Ile Ile Asn Val Phe Ser Glu Ile Gly Glu
1               5                   10                  15

Leu Lys Lys Val Leu Ile His Thr Pro Gly Asn Glu Leu Lys Tyr Val
                20                  25                  30

Ser Pro Tyr Arg Leu Asp Glu Leu Phe Ser Asn Val Leu Glu Trp
                35                  40                  45

Arg Glu Ala Lys Lys Glu His Asn Glu Phe Ile Gln Lys Leu Lys Ser
                50                  55                  60

Glu Gly Val Glu Pro Val Glu Leu Thr Asp Leu Val Ala Glu Ser Phe
65                  70                  75                  80

Glu Glu Ser Ser Ile Lys Val Lys Asn Asp Phe Ile Arg Gln Tyr Leu
                85                  90                  95

Asp Glu Ala Thr Pro Ile Leu Asp Gly Leu Thr Lys Gln Lys Leu Leu
                100                 105                 110

Pro Phe Phe Leu Asp Ile Lys His Ser Thr Arg Lys Thr Ile Glu Leu
                115                 120                 125

Met Met Ser Gly Ile Thr Gln Lys Asp Ile Ser Ile Ser His Ile Glu
                130                 135                 140

Arg Glu Leu Ile Ile Asp Pro Met Pro Asn Leu Tyr Phe Ser Arg Asp
145                 150                 155                 160

Asn Phe Ile Ser Ile Gly Asn Ser Val Ile Ile Ser Asn Met Lys Tyr
                165                 170                 175

Lys Thr Arg Lys Arg Glu Thr Ile Phe Thr Asp Phe Ile Phe Lys Asn
                180                 185                 190

His Pro Leu Tyr Lys Lys Val Asn Met Ala Phe Glu Arg Lys Asp Leu
                195                 200                 205

Asn Asn Gln Ile Ser Ile Glu Gly Gly Asp Val Leu Val Tyr Ser
                210                 215                 220

Lys Glu Ile Leu Ile Ile Gly Ile Ser Glu Arg Thr Thr Met Ser Ala
225                 230                 235                 240

Ile Leu Glu Leu Ala Glu Asn Phe Lys Lys Thr Lys Arg Ser Phe Lys
                245                 250                 255

Lys Ile Tyr Gly Val Glu Val Pro Lys Met Lys Asn Leu Met His Leu
                260                 265                 270

Asp Thr Trp Leu Thr Met Ile Asp Tyr Asp Lys Phe Ile Tyr Ser Pro

```
            275                 280                 285
Asn Val Leu Thr Asp Leu Lys Phe Trp Glu Ile Asn Leu Asp Tyr Glu
290                 295                 300

Lys Ile Ser Ser Lys Glu Leu His Ala Ser Leu Ser Glu Phe Leu Lys
305                 310                 315                 320

Leu Ile Ile Gly Lys Asp Pro Ile Leu Ile Pro Ile Gly Gly Lys Gly
                325                 330                 335

Ala Ser Gln Ile Thr Ile Asp Ile Glu Thr Asn Phe Val Ala Ala Asn
                340                 345                 350

Tyr Leu Val Ile Arg Pro Gly Val Val Ile Gly Tyr Ser Arg Asn Tyr
                355                 360                 365

Glu Thr Gln Lys Ala Leu Glu Gly His Gly Val Lys Val Ile Ala Phe
370                 375                 380

Glu Gly Asn Gln Leu Ser Leu Gly Met Gly Ser Ser Arg Cys Met Ser
385                 390                 395                 400

Met Pro Leu Ile Arg Ser Asn Leu Lys
                405

<210> SEQ ID NO 17
<211> LENGTH: 411
<212> TYPE: PRT
<213> ORGANISM: Streptococcus pyogenes

<400> SEQUENCE: 17

Met Thr Ala Gln Thr Pro Ile His Val Tyr Ser Glu Ile Gly Lys Leu
1               5                   10                  15

Lys Lys Val Leu Leu His Arg Pro Gly Lys Glu Ile Glu Asn Leu Met
                20                  25                  30

Pro Asp Tyr Leu Glu Arg Leu Leu Phe Asp Asp Ile Pro Phe Leu Glu
            35                  40                  45

Asp Ala Gln Lys Glu His Asp Ala Phe Ala Gln Ala Leu Arg Asp Glu
        50                  55                  60

Gly Ile Glu Val Leu Tyr Leu Glu Thr Leu Ala Ala Glu Ser Leu Val
65                  70                  75                  80

Thr Pro Glu Ile Arg Glu Ala Phe Ile Asp Glu Tyr Leu Ser Glu Ala
                85                  90                  95

Asn Ile Arg Gly Arg Ala Thr Lys Lys Ala Ile Arg Glu Leu Leu Met
                100                 105                 110

Ala Ile Glu Asp Asn Gln Glu Leu Ile Glu Lys Thr Met Ala Gly Val
            115                 120                 125

Gln Lys Ser Glu Leu Pro Glu Ile Pro Ala Ser Glu Lys Gly Leu Thr
        130                 135                 140

Asp Leu Val Glu Ser Asn Tyr Pro Phe Ala Ile Asp Pro Met Pro Asn
145                 150                 155                 160

Leu Tyr Phe Thr Arg Asp Pro Phe Ala Thr Ile Gly Thr Gly Val Ser
                165                 170                 175

Leu Asn His Met Phe Ser Glu Thr Arg Asn Arg Glu Thr Leu Tyr Gly
                180                 185                 190

Lys Tyr Ile Phe Thr His His Pro Ile Tyr Gly Gly Gly Lys Val Pro
            195                 200                 205

Met Val Tyr Asp Arg Asn Glu Thr Thr Arg Ile Glu Gly Gly Asp Glu
        210                 215                 220

Leu Val Leu Ser Lys Asp Val Leu Ala Val Gly Ile Ser Gln Arg Thr
225                 230                 235                 240
```

```
Asp Ala Ala Ser Ile Glu Lys Leu Leu Val Asn Ile Phe Lys Gln Asn
            245                 250                 255

Leu Gly Phe Lys Lys Val Leu Ala Phe Glu Phe Ala Asn Asn Arg Lys
        260                 265                 270

Phe Met His Leu Asp Thr Val Phe Thr Met Val Asp Tyr Asp Lys Phe
    275                 280                 285

Thr Ile His Pro Glu Ile Glu Gly Asp Leu Arg Val Tyr Ser Val Thr
290                 295                 300

Tyr Asp Asn Glu Glu Leu His Ile Val Glu Lys Gly Asp Leu Ala
305                 310                 315                 320

Glu Leu Leu Ala Ala Asn Leu Gly Val Glu Lys Val Asp Leu Ile Arg
                325                 330                 335

Cys Gly Gly Asp Asn Leu Val Ala Ala Gly Arg Glu Gln Trp Asn Asp
            340                 345                 350

Gly Ser Asn Thr Leu Thr Ile Ala Pro Gly Val Val Val Tyr Asn
        355                 360                 365

Arg Asn Thr Ile Thr Asn Ala Ile Leu Glu Ser Lys Gly Leu Lys Leu
    370                 375                 380

Ile Lys Ile His Gly Ser Glu Leu Val Arg Gly Arg Gly Pro Arg
385                 390                 395                 400

Cys Met Ser Met Pro Phe Glu Arg Glu Asp Ile
                405                 410

<210> SEQ ID NO 18
<211> LENGTH: 408
<212> TYPE: PRT
<213> ORGANISM: Enterococcus faecalis

<400> SEQUENCE: 18

Met Ser His Pro Ile Asn Val Phe Ser Glu Ile Gly Lys Leu Lys Thr
1               5                   10                  15

Val Met Leu His Arg Pro Gly Lys Glu Leu Glu Asn Leu Met Pro Asp
            20                  25                  30

Tyr Leu Glu Arg Leu Leu Phe Asp Asp Ile Pro Phe Leu Glu Lys Ala
        35                  40                  45

Gln Ala Glu His Asp Ala Phe Ala Glu Leu Leu Arg Ser Lys Asp Ile
    50                  55                  60

Glu Val Val Tyr Leu Glu Asp Leu Ala Ala Glu Ala Leu Ile Asn Glu
65                  70                  75                  80

Glu Val Arg Arg Gln Phe Ile Asp Gln Phe Leu Glu Glu Ala Asn Ile
                85                  90                  95

Arg Ser Glu Ser Ala Lys Glu Lys Val Arg Glu Leu Met Leu Glu Ile
            100                 105                 110

Asp Asp Asn Glu Glu Leu Ile Gln Lys Ala Ile Ala Gly Ile Gln Lys
        115                 120                 125

Gln Glu Leu Pro Lys Tyr Glu Gln Glu Phe Leu Thr Asp Met Val Glu
    130                 135                 140

Ala Asp Tyr Pro Phe Ile Ile Asp Pro Met Pro Asn Leu Tyr Phe Thr
145                 150                 155                 160

Arg Asp Asn Phe Ala Thr Met Gly His Gly Ile Ser Leu Asn His Met
                165                 170                 175

Tyr Ser Val Thr Arg Gln Arg Glu Thr Ile Phe Gly Gln Tyr Ile Phe
            180                 185                 190

Asp Tyr His Pro Arg Phe Ala Gly Lys Glu Val Pro Arg Val Tyr Asp
        195                 200                 205
```

-continued

```
Arg Ser Glu Ser Thr Arg Ile Glu Gly Gly Asp Glu Leu Ile Leu Ser
    210                 215                 220

Lys Glu Val Val Ala Ile Gly Ile Ser Gln Arg Thr Asp Ala Ala Ser
225                 230                 235                 240

Ile Glu Lys Ile Ala Arg Asn Ile Phe Glu Gln Lys Leu Gly Phe Lys
                245                 250                 255

Asn Ile Leu Ala Phe Asp Ile Gly Glu His Arg Lys Phe Met His Leu
            260                 265                 270

Asp Thr Val Phe Thr Met Ile Asp Tyr Asp Lys Phe Thr Ile His Pro
        275                 280                 285

Glu Ile Glu Gly Gly Leu Val Val Tyr Ser Ile Thr Glu Lys Ala Asp
    290                 295                 300

Gly Asp Ile Gln Ile Thr Lys Glu Lys Asp Thr Leu Asp Asn Ile Leu
305                 310                 315                 320

Cys Lys Tyr Leu His Leu Asp Asn Val Gln Leu Ile Arg Cys Gly Ala
                325                 330                 335

Gly Asn Leu Thr Ala Ala Ala Arg Glu Gln Trp Asn Asp Gly Ser Asn
            340                 345                 350

Thr Leu Ala Ile Ala Pro Gly Glu Val Val Val Tyr Asp Arg Asn Thr
        355                 360                 365

Ile Thr Asn Lys Ala Leu Glu Glu Ala Gly Val Lys Leu Asn Tyr Ile
    370                 375                 380

Pro Gly Ser Glu Leu Val Arg Gly Arg Gly Gly Pro Arg Cys Met Ser
385                 390                 395                 400

Met Pro Leu Tyr Arg Glu Asp Leu
                405

<210> SEQ ID NO 19
<211> LENGTH: 403
<212> TYPE: PRT
<213> ORGANISM: Mycoplasma capricolum

<400> SEQUENCE: 19

Met Glu Lys Lys Ile Asn Val Phe Ser Glu Ile Gly Thr Leu Lys Thr
1               5                   10                  15

Val Leu Val His Arg Pro Gly Asp Glu Ile Glu Asn Leu Thr Pro Glu
            20                  25                  30

Leu Leu Glu Arg Leu Leu Phe Asp Asp Val Pro Phe Lys Asp Val Ala
        35                  40                  45

Val Lys Glu His Asp Ala Phe Thr Lys Ile Met Arg Asp Asn Gly Val
    50                  55                  60

Glu Val Leu Tyr Ile Glu Lys Leu Ala Ala Glu Thr Leu Asp Gln His
65                  70                  75                  80

Pro Asp Leu Arg Glu Lys Phe Ile Asp Gln Phe Ile Ser Glu Ala Asn
                85                  90                  95

Ile Glu Asp Lys Tyr Lys Glu Lys Tyr Arg Asp Phe Ile Ser Ser Leu
            100                 105                 110

Asp Asn Tyr Arg Met Ile Lys Lys Met Ile Ala Gly Thr Lys Lys Leu
        115                 120                 125

Glu Leu Gly Ile Asp Glu Gly Tyr Lys Ala Tyr Pro Phe Ile Ala Asp
    130                 135                 140

Pro Leu Pro Asn Val Leu Phe Gln Arg Asp Pro Phe Ser Ser Val Gly
145                 150                 155                 160

Phe Gly Ile Thr Met Asn Arg Met Trp Ser Val Thr Arg Asn Arg Glu
```

```
                    165                 170                 175
Thr Ile Phe Pro Asp Leu Val Phe Lys His His Asn Arg Phe Ala Asn
                180                 185                 190
Gln Val Pro Tyr Tyr Tyr Glu Arg Asp Trp Lys Glu Thr Ile Glu
            195                 200                 205
Gly Gly Asp Ile Leu Val Leu Asn Lys Glu Thr Leu Ile Ile Gly Val
        210                 215                 220
Thr Gln Arg Thr Thr Leu Lys Ala Ile Glu Lys Phe Ser Glu Arg Leu
225                 230                 235                 240
Phe Asn Asp Pro Glu Ser Ser Tyr Ser Lys Val Ile Ala Leu Asp Leu
            245                 250                 255
Pro Lys Ser Arg Ala Phe Met His Leu Asp Thr Val Phe Thr Asn Ile
            260                 265                 270
Asp Tyr Asp Lys Phe Ile Ala His Pro Leu Ile Phe Asp Cys Ile Asp
        275                 280                 285
Glu Phe Lys Ile Tyr Glu Val Ser Lys Gln Gly Thr Lys Glu Val Lys
        290                 295                 300
Lys Thr Leu Ile Glu Leu Leu Ser Asp Ala Ala Gly Arg Glu Val Gln
305                 310                 315                 320
Ile Ile Arg Cys Gly Gly Asn Asp Val Val Gly Ala Ser Arg Glu Gln
                325                 330                 335
Trp Asn Asp Gly Thr Asn Val Val Ala Leu Arg Pro Gly Lys Val Ile
            340                 345                 350
Ala Tyr Glu Arg Asn Trp Ile Thr Ile Asp Leu Leu Arg Lys Ala Gly
            355                 360                 365
Val Glu Val Leu Thr Ile Ala Ser Ser Glu Leu Ser Arg Gly Arg Gly
        370                 375                 380
Gly Pro Arg Cys Met Thr Met Pro Leu Trp Arg Glu Asp Leu Gln Glu
385                 390                 395                 400
Ile Lys Arg

<210> SEQ ID NO 20
<211> LENGTH: 410
<212> TYPE: PRT
<213> ORGANISM: Halothermothrix orenii

<400> SEQUENCE: 20

Met Phe Lys Lys Ser Pro Leu Asn Val Thr Ser Glu Ile Gly Lys Leu
1               5                   10                  15
Lys Lys Val Leu Leu His Arg Pro Gly His Glu Ile Glu Asn Leu Thr
            20                  25                  30
Pro Asp Leu Leu Glu Arg Leu Leu Phe Asp Asp Ile Pro Tyr Leu Lys
        35                  40                  45
Val Ala Gln Glu Glu His Asp Ala Phe Ala Gln Thr Leu Arg Asp Asn
    50                  55                  60
Gly Val Glu Val Leu Tyr Leu His Glu Leu Ala Ala Glu Ala Ile Gln
65                  70                  75                  80
Glu Asp Glu Ile Arg Lys Lys Phe Ile Glu Gln Phe Leu Asp Glu Ala
                85                  90                  95
Gly Val Ile Gly Lys Gly Ala Arg Gln Val Leu Lys Glu Tyr Phe Ala
            100                 105                 110
Asp Met Asp Asn Glu Thr Leu Ile Arg Lys Met Met Ala Gly Val Arg
        115                 120                 125
Lys Lys Glu Ile Pro Ala Ile Glu Lys Val Ala Ser Leu Asn Asp Met
```

Val Glu Glu Asp Tyr Pro Phe Val Leu Asp Pro Met Pro Asn Leu Tyr
145                 150                 155                 160

Phe Thr Arg Asp Pro Phe Ala Thr Ile Gly Thr Gly Ile Thr Leu Asn
                165                 170                 175

His Met Arg Thr Glu Thr Arg Asn Arg Glu Val Ile Phe Ala Glu Tyr
            180                 185                 190

Ile Phe Ser Tyr His Pro Asp Phe Lys Asp Thr Glu Ile Pro Phe Trp
        195                 200                 205

Phe Asp Arg Asn Glu Thr Thr Ser Ile Glu Gly Gly Asp Glu Leu Ile
    210                 215                 220

Leu Ser Asp Lys Val Leu Ala Met Gly Ile Ser Glu Arg Thr Asp Ala
225                 230                 235                 240

Ala Ser Ile Glu Lys Val Ala Arg Asn Ile Phe Thr Asp Gly Gln Pro
                245                 250                 255

Phe Glu Thr Ile Leu Ala Phe Lys Ile Pro Glu Lys Arg Ala Phe Met
                260                 265                 270

His Leu Asp Thr Val Phe Thr Met Val Asp Tyr Asp Lys Phe Thr Ile
            275                 280                 285

His Ala Glu Ile Glu Gly Pro Leu Lys Val Tyr Ser Ile Thr Lys Gly
        290                 295                 300

Asp Asn Asp Glu Leu Lys Ile Asp Glu Lys Ala Thr Leu Glu Asp
305                 310                 315                 320

Thr Leu Lys Lys Tyr Leu Gly Leu Asp Glu Val Thr Leu Ile Arg Cys
                325                 330                 335

Ala Gly Gly Asp Tyr Ile Asp Ala Gly Arg Glu Gln Trp Asn Asp Gly
                340                 345                 350

Ser Asn Thr Leu Ala Ile Ala Pro Gly Glu Val Val Val Tyr Asn Arg
            355                 360                 365

Asn His Thr Thr Asn Arg Leu Leu Glu Glu His Gly Ile Lys Leu His
        370                 375                 380

Val Ile Pro Ser Ser Glu Leu Ser Arg Gly Arg Gly Pro Arg Cys
385                 390                 395                 400

Met Ser Met Pro Leu Val Arg Glu Asp Ile
                405                 410

<210> SEQ ID NO 21
<211> LENGTH: 411
<212> TYPE: PRT
<213> ORGANISM: Staphylococcus aureus

<400> SEQUENCE: 21

Met Thr Asp Gly Pro Ile Lys Val Asn Ser Glu Ile Gly Ala Leu Lys
1               5                   10                  15

Thr Val Leu Leu Lys Arg Pro Gly Lys Glu Leu Glu Asn Leu Val Pro
                20                  25                  30

Asp Tyr Leu Asp Gly Leu Leu Phe Asp Ile Pro Tyr Leu Glu Val
            35                  40                  45

Ala Gln Lys Glu His Asp His Phe Ala Gln Val Leu Arg Glu Glu Gly
        50                  55                  60

Val Glu Val Leu Tyr Leu Glu Lys Leu Ala Ala Glu Ser Ile Glu Asn
65                  70                  75                  80

Pro Gln Val Arg Ser Glu Phe Ile Asp Asp Val Leu Ala Glu Ser Lys
                85                  90                  95

```
Lys Thr Ile Leu Gly His Glu Glu Ile Lys Ala Leu Phe Ala Thr
            100                 105                 110

Leu Ser Asn Gln Glu Leu Val Asp Lys Ile Met Ser Gly Val Arg Lys
        115                 120                 125

Glu Glu Ile Asn Pro Lys Cys Thr His Leu Val Glu Tyr Met Asp Asp
130                 135                 140

Lys Tyr Pro Phe Tyr Leu Asp Pro Met Pro Asn Leu Tyr Phe Thr Arg
145                 150                 155                 160

Asp Pro Gln Ala Ser Ile Gly His Gly Ile Thr Ile Asn Arg Met Phe
                165                 170                 175

Trp Arg Ala Arg Arg Glu Ser Ile Phe Ile Gln Tyr Ile Val Lys
        180                 185                 190

His His Pro Arg Phe Lys Asp Ala Asn Ile Pro Ile Trp Leu Asp Arg
            195                 200                 205

Asp Cys Pro Phe Asn Ile Glu Gly Gly Asp Glu Leu Val Leu Ser Lys
        210                 215                 220

Asp Val Leu Ala Ile Gly Val Ser Glu Arg Thr Ser Ala Gln Ala Ile
225                 230                 235                 240

Glu Lys Leu Ala Arg Arg Ile Phe Glu Asn Pro Gln Ala Thr Phe Lys
                245                 250                 255

Lys Val Val Ala Ile Glu Ile Pro Thr Ser Arg Thr Phe Met His Leu
            260                 265                 270

Asp Thr Val Phe Thr Met Ile Asp Tyr Asp Lys Phe Thr Met His Ser
        275                 280                 285

Ala Ile Leu Lys Ala Glu Gly Asn Met Asn Ile Phe Ile Ile Glu Tyr
        290                 295                 300

Asp Asp Val Asn Lys Asp Ile Ala Ile Lys Gln Ser Ser His Leu Lys
305                 310                 315                 320

Asp Thr Leu Glu Asp Val Leu Gly Ile Asp Ile Gln Phe Ile Pro
                325                 330                 335

Thr Gly Asn Gly Asp Val Ile Asp Gly Ala Arg Glu Gln Trp Asn Asp
            340                 345                 350

Gly Ser Asn Thr Leu Cys Ile Arg Pro Gly Val Val Thr Tyr Asp
        355                 360                 365

Arg Asn Tyr Val Ser Asn Asp Leu Leu Arg Gln Lys Gly Ile Lys Val
370                 375                 380

Ile Glu Ile Ser Gly Ser Glu Leu Val Arg Gly Arg Gly Pro Arg
385                 390                 395                 400

Cys Met Ser Gln Pro Leu Phe Arg Glu Asp Ile
                405                 410

<210> SEQ ID NO 22
<211> LENGTH: 417
<212> TYPE: PRT
<213> ORGANISM: Pseudomonas plecoglossicida

<400> SEQUENCE: 22

Met Ser Ala Glu Lys Gln Lys Tyr Gly Val His Ser Glu Ala Gly Lys
1               5                   10                  15

Leu Arg Lys Val Met Val Cys Ala Pro Gly Leu Ala His Lys Arg Leu
            20                  25                  30

Thr Pro Ser Asn Cys Asp Glu Leu Leu Phe Asp Asp Val Ile Trp Val
        35                  40                  45

Asp Gln Ala Lys Arg Asp His Phe Asp Phe Val Thr Lys Met Arg Glu
    50                  55                  60
```

```
Arg Gly Val Asp Val Leu Glu Met His Asn Leu Leu Thr Asp Ile Val
 65                  70                  75                  80

Gln Asn Pro Glu Ala Leu Lys Trp Ile Leu Asp Arg Lys Ile Thr Pro
                 85                  90                  95

Asp Thr Val Gly Val Gly Leu Thr Asn Glu Val Arg Ser Trp Leu Glu
            100                 105                 110

Gly Gln Glu Pro Arg His Leu Ala Glu Phe Leu Ile Gly Gly Val Ala
        115                 120                 125

Gly Gln Asp Leu Pro Glu Ser Glu Gly Ala Ser Val Val Lys Met Tyr
    130                 135                 140

Asn Asp Tyr Leu Gly His Ser Ser Phe Ile Leu Pro Pro Leu Pro Asn
145                 150                 155                 160

Thr Gln Phe Thr Arg Asp Thr Thr Cys Trp Ile Tyr Gly Gly Val Thr
                165                 170                 175

Leu Asn Pro Met Tyr Trp Pro Ala Arg Arg Gln Glu Thr Leu Leu Thr
            180                 185                 190

Thr Ala Ile Tyr Lys Phe His Pro Glu Phe Thr Lys Ala Asp Phe Gln
        195                 200                 205

Val Trp Tyr Gly Asp Pro Asp Gln Glu His Gly Gln Ala Thr Leu Glu
    210                 215                 220

Gly Gly Asp Val Met Pro Ile Gly Lys Gly Ile Val Leu Ile Gly Met
225                 230                 235                 240

Gly Glu Arg Thr Ser Arg Gln Ala Ile Gly Gln Leu Ala Gln Asn Leu
                245                 250                 255

Phe Ala Lys Gly Ala Val Glu Gln Ile Val Ala Gly Leu Pro Lys
            260                 265                 270

Ser Arg Ala Ala Met His Leu Asp Thr Val Phe Ser Phe Cys Asp Arg
        275                 280                 285

Asp Leu Val Thr Val Phe Pro Glu Val Val Arg Glu Ile Val Pro Phe
    290                 295                 300

Ile Ile Arg Pro Asp Glu Ser Lys Pro Tyr Gly Met Asp Val Arg Arg
305                 310                 315                 320

Glu Asn Lys Ser Phe Ile Glu Val Val Gly Gln Leu Gly Val Lys
                325                 330                 335

Leu Arg Val Val Glu Thr Gly Gly Asn Ser Phe Ala Ala Glu Arg Glu
            340                 345                 350

Gln Trp Asp Asp Gly Asn Asn Val Ala Leu Glu Pro Gly Val Val
        355                 360                 365

Ile Gly Tyr Asp Arg Asn Thr Tyr Thr Asn Thr Leu Leu Arg Lys Ala
    370                 375                 380

Gly Ile Glu Val Ile Thr Ile Ser Ala Gly Glu Leu Gly Arg Gly Arg
385                 390                 395                 400

Gly Gly Gly His Cys Met Thr Cys Pro Ile Val Arg Asp Pro Ile Asn
                405                 410                 415

Tyr

<210> SEQ ID NO 23
<211> LENGTH: 417
<212> TYPE: PRT
<213> ORGANISM: Pseudomonas putida

<400> SEQUENCE: 23

Met Ser Ala Glu Lys Gln Lys Tyr Gly Val His Ser Glu Ala Gly Lys
1               5                  10                  15
```

Leu Arg Lys Val Met Val Cys Ser Pro Gly Leu Ala His Lys Arg Leu
            20                  25                  30

Thr Pro Ser Asn Cys Asp Glu Leu Phe Asp Val Ile Trp Val
            35                  40                  45

Asp Gln Ala Lys Arg Asp His Phe Asp Phe Val Thr Lys Met Arg Glu
 50                  55                  60

Arg Gly Val Asp Val Leu Glu Met His Asn Leu Leu Thr Asp Ile Val
 65                  70                  75                  80

Gln Gln Pro Glu Ala Leu Lys Trp Ile Leu Asp Arg Lys Ile Thr Ser
            85                  90                  95

Asp Thr Val Gly Val Gly Leu Thr Asn Glu Val Arg Ser Trp Leu Glu
            100                 105                 110

Gly Leu Glu Pro Arg His Leu Ala Glu Phe Leu Ile Gly Gly Val Ala
            115                 120                 125

Gly Gln Asp Leu Pro Glu Ser Glu Gly Ala Ser Val Val Lys Met Tyr
 130                 135                 140

Asn Asp Tyr Leu Gly His Ser Ser Phe Ile Leu Pro Pro Leu Pro Asn
145                 150                 155                 160

Thr Gln Phe Thr Arg Asp Thr Thr Cys Trp Ile Tyr Gly Gly Val Thr
            165                 170                 175

Leu Asn Pro Met Tyr Trp Pro Ala Arg Arg Gln Glu Thr Leu Leu Thr
            180                 185                 190

Thr Ala Ile Tyr Lys Phe His Lys Glu Phe Thr Gly Ala Asp Phe Gln
            195                 200                 205

Val Trp Tyr Gly Asp Pro Asp Lys Asp His Gly Asn Ala Thr Leu Glu
            210                 215                 220

Gly Gly Asp Val Met Pro Ile Gly Lys Gly Ile Val Leu Ile Gly Met
225                 230                 235                 240

Gly Glu Arg Thr Ser Arg Gln Ala Ile Gly Gln Leu Ala Gln Asn Leu
            245                 250                 255

Phe Ala Lys Gly Ala Val Glu Lys Val Ile Val Ala Gly Leu Pro Lys
            260                 265                 270

Ser Arg Ala Ala Met His Leu Asp Thr Val Phe Ser Phe Cys Asp Arg
            275                 280                 285

Asp Leu Val Thr Val Phe Pro Glu Val Val Lys Glu Ile Val Pro Phe
            290                 295                 300

Ile Ile Arg Pro Asp Glu Ser Lys Pro Tyr Gly Met Asp Val Arg Arg
305                 310                 315                 320

Glu Asn Lys Ser Phe Ile Glu Val Val Gly Glu Gln Leu Gly Val Lys
            325                 330                 335

Leu Arg Val Val Glu Thr Gly Gly Asn Ser Phe Ala Ala Glu Arg Glu
            340                 345                 350

Gln Trp Asp Asp Gly Asn Asn Val Val Ala Met Glu Pro Gly Val Val
            355                 360                 365

Ile Gly Tyr Asp Arg Asn Thr Tyr Thr Asn Thr Leu Leu Arg Lys Ala
            370                 375                 380

Gly Ile Glu Val Ile Thr Ile Ser Ala Gly Glu Leu Gly Arg Gly Arg
385                 390                 395                 400

Gly Gly Gly His Cys Met Thr Cys Pro Ile Val Arg Asp Pro Ile Asp
            405                 410                 415

Tyr

```
<210> SEQ ID NO 24
<211> LENGTH: 418
<212> TYPE: PRT
<213> ORGANISM: Pseudomonas aeruginosa

<400> SEQUENCE: 24
```

| | | | | | | | | | | | | | | |
|---|---|---|---|---|---|---|---|---|---|---|---|---|---|---|
| Met | Ser | Thr | Glu | Lys | Thr | Lys | Leu | Gly | Val | His | Ser | Glu | Ala | Gly | Lys |
| 1 | | | | 5 | | | | | 10 | | | | | 15 | |
| Leu | Arg | Lys | Val | Met | Val | Cys | Ser | Pro | Gly | Leu | Ala | His | Gln | Arg | Leu |
| | | | 20 | | | | | 25 | | | | | 30 | | |
| Thr | Pro | Ser | Asn | Cys | Asp | Glu | Leu | Leu | Phe | Asp | Asp | Val | Ile | Trp | Val |
| | | 35 | | | | | 40 | | | | | 45 | | | |
| Asn | Gln | Ala | Lys | Arg | Asp | His | Phe | Asp | Phe | Val | Thr | Lys | Met | Arg | Glu |
| 50 | | | | | 55 | | | | | 60 | | | | | |
| Arg | Gly | Ile | Asp | Val | Leu | Glu | Met | His | Asn | Leu | Leu | Thr | Glu | Thr | Ile |
| 65 | | | | 70 | | | | | 75 | | | | | 80 | |
| Gln | Asn | Pro | Glu | Ala | Leu | Lys | Trp | Ile | Leu | Asp | Arg | Lys | Ile | Thr | Ala |
| | | | | 85 | | | | | 90 | | | | | 95 | |
| Asp | Ser | Val | Gly | Leu | Gly | Leu | Thr | Ser | Glu | Leu | Arg | Ser | Trp | Leu | Glu |
| | | | 100 | | | | | 105 | | | | | 110 | | |
| Ser | Leu | Glu | Pro | Arg | Lys | Leu | Ala | Glu | Tyr | Leu | Ile | Gly | Gly | Val | Ala |
| | | | 115 | | | | | 120 | | | | | 125 | | |
| Ala | Asp | Asp | Leu | Pro | Ala | Ser | Glu | Gly | Ala | Asn | Ile | Leu | Lys | Met | Tyr |
| | 130 | | | | | 135 | | | | | 140 | | | | |
| Arg | Glu | Tyr | Leu | Gly | His | Ser | Ser | Phe | Leu | Leu | Pro | Pro | Leu | Pro | Asn |
| 145 | | | | | 150 | | | | | 155 | | | | | 160 |
| Thr | Gln | Phe | Thr | Arg | Asp | Thr | Thr | Cys | Trp | Ile | Tyr | Gly | Gly | Val | Thr |
| | | | | 165 | | | | | 170 | | | | | 175 | |
| Leu | Asn | Pro | Met | Tyr | Trp | Pro | Ala | Arg | Arg | Gln | Glu | Thr | Leu | Leu | Thr |
| | | | 180 | | | | | 185 | | | | | 190 | | |
| Thr | Ala | Ile | Tyr | Lys | Phe | His | Pro | Glu | Phe | Ala | Asn | Ala | Glu | Phe | Glu |
| | | | 195 | | | | | 200 | | | | | 205 | | |
| Ile | Trp | Tyr | Gly | Asp | Pro | Asp | Lys | Asp | His | Gly | Ser | Ser | Thr | Leu | Glu |
| | 210 | | | | | 215 | | | | | 220 | | | | |
| Gly | Gly | Asp | Val | Met | Pro | Ile | Gly | Asn | Gly | Val | Val | Leu | Ile | Gly | Met |
| 225 | | | | | 230 | | | | | 235 | | | | | 240 |
| Gly | Glu | Arg | Ser | Ser | Arg | Gln | Ala | Ile | Gly | Gln | Val | Ala | Gln | Ser | Leu |
| | | | | 245 | | | | | 250 | | | | | 255 | |
| Phe | Ala | Lys | Gly | Ala | Ala | Glu | Arg | Val | Ile | Val | Ala | Gly | Leu | Pro | Lys |
| | | | 260 | | | | | 265 | | | | | 270 | | |
| Ser | Arg | Ala | Ala | Met | His | Leu | Asp | Thr | Val | Phe | Ser | Phe | Cys | Asp | Arg |
| | | 275 | | | | | 280 | | | | | 285 | | | |
| Asp | Leu | Val | Thr | Val | Phe | Pro | Glu | Val | Val | Lys | Glu | Ile | Val | Pro | Phe |
| | 290 | | | | | 295 | | | | | 300 | | | | |
| Ser | Leu | Arg | Pro | Asp | Ala | Ser | Ser | Pro | Tyr | Gly | Met | Ser | Ile | Arg | Arg |
| 305 | | | | | 310 | | | | | 315 | | | | | 320 |
| Glu | Glu | Lys | Thr | Phe | Leu | Glu | Val | Val | Ala | Glu | Ser | Leu | Gly | Leu | Lys |
| | | | | 325 | | | | | 330 | | | | | 335 | |
| Lys | Leu | Arg | Val | Val | Glu | Thr | Gly | Gly | Asn | Ser | Phe | Ala | Ala | Glu | Arg |
| | | | 340 | | | | | 345 | | | | | 350 | | |
| Glu | Gln | Trp | Asp | Asp | Gly | Asn | Asn | Val | Val | Cys | Leu | Glu | Pro | Gly | Val |
| | | 355 | | | | | 360 | | | | | 365 | | | |
| Val | Val | Gly | Tyr | Asp | Arg | Asn | Thr | Tyr | Thr | Asn | Thr | Leu | Leu | Arg | Lys |
| | 370 | | | | | 375 | | | | | 380 | | | | |

Ala Gly Val Glu Val Ile Thr Ile Ser Ala Ser Glu Leu Gly Arg Gly
385                 390                 395                 400

Arg Gly Gly Gly His Cys Met Thr Cys Pro Ile Ile Arg Asp Pro Ile
            405                 410                 415

Asp Tyr

<210> SEQ ID NO 25
<211> LENGTH: 402
<212> TYPE: PRT
<213> ORGANISM: Mycobacterium bovis

<400> SEQUENCE: 25

Met Gly Val Glu Leu Gly Ser Asn Ser Glu Val Gly Ala Leu Arg Val
1               5                   10                  15

Val Ile Leu His Arg Pro Gly Ala Glu Leu Arg Arg Leu Thr Pro Arg
            20                  25                  30

Asn Thr Asp Gln Leu Leu Phe Asp Gly Leu Pro Trp Val Ser Arg Ala
        35                  40                  45

Gln Asp Glu His Asp Glu Phe Ala Glu Leu Leu Ala Ser Arg Gly Ala
    50                  55                  60

Glu Val Leu Leu Leu Ser Asp Leu Leu Thr Glu Ala Leu His His Ser
65                  70                  75                  80

Gly Ala Ala Arg Met Gln Gly Ile Ala Ala Val Asp Ala Pro Arg
                85                  90                  95

Leu Gly Leu Pro Leu Ala Gln Glu Leu Ser Ala Tyr Leu Arg Ser Leu
            100                 105                 110

Asp Pro Gly Arg Leu Ala His Val Leu Thr Ala Gly Met Thr Phe Asn
        115                 120                 125

Glu Leu Pro Ser Asp Thr Arg Thr Asp Val Ser Leu Val Leu Arg Met
130                 135                 140

His His Gly Gly Asp Phe Val Ile Glu Pro Leu Pro Asn Leu Val Phe
145                 150                 155                 160

Thr Arg Asp Ser Ser Ile Trp Ile Gly Pro Arg Val Val Ile Pro Ser
                165                 170                 175

Leu Ala Leu Arg Ala Arg Val Arg Glu Ala Ser Leu Thr Asp Leu Ile
            180                 185                 190

Tyr Ala His His Pro Arg Phe Thr Gly Val Arg Arg Ala Tyr Glu Ser
        195                 200                 205

Arg Thr Ala Pro Val Glu Gly Gly Asp Val Leu Leu Leu Ala Pro Gly
    210                 215                 220

Val Val Ala Val Gly Val Gly Glu Arg Thr Thr Pro Ala Gly Ala Glu
225                 230                 235                 240

Ala Leu Ala Arg Ser Leu Phe Asp Asp Leu Ala His Thr Val Leu
                245                 250                 255

Ala Val Pro Ile Ala Gln Gln Arg Ala Gln Met His Leu Asp Thr Val
            260                 265                 270

Cys Thr Met Val Asp Thr Asp Thr Met Val Met Tyr Ala Asn Val Val
        275                 280                 285

Asp Thr Leu Glu Ala Phe Thr Ile Gln Arg Thr Pro Asp Gly Val Thr
    290                 295                 300

Ile Gly Asp Ala Ala Pro Phe Ala Glu Ala Ala Lys Ala Met Gly
305                 310                 315                 320

Ile Asp Lys Leu Arg Val Ile His Thr Gly Met Asp Pro Val Val Ala
                325                 330                 335

```
Glu Arg Glu Gln Trp Asp Asp Gly Asn Asn Thr Leu Ala Leu Ala Pro
                340                 345                 350

Gly Val Val Ala Tyr Glu Arg Asn Val Gln Thr Asn Ala Arg Leu
            355                 360                 365

Gln Asp Ala Gly Ile Glu Val Leu Thr Ile Ala Gly Ser Glu Leu Gly
    370                 375                 380

Thr Gly Arg Gly Gly Pro Arg Cys Met Ser Cys Pro Ala Ala Arg Asp
385                 390                 395                 400

Pro Leu

<210> SEQ ID NO 26
<211> LENGTH: 410
<212> TYPE: PRT
<213> ORGANISM: Artificial Sequence
<220> FEATURE:
<223> OTHER INFORMATION: Mycoplasma arginini arginine deiminase with
      flanking synthesized residues added

<400> SEQUENCE: 26

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Lys Gln Phe Val Ala Glu
    50                  55                  60

Leu Lys Ala Asn Asp Ile Asn Val Val Glu Leu Ile Asp Leu Val Ala
65                  70                  75                  80

Glu Thr Tyr Asp Leu Ala Ser Gln Glu Ala Lys Asp Lys Leu Ile Glu
                85                  90                  95

Glu Phe Leu Glu Asp Ser Glu Pro Val Leu Ser Glu Glu His Lys Val
            100                 105                 110

Val Val Arg Asn Phe Leu Lys Ala Lys Lys Thr Ser Arg Glu Leu Val
        115                 120                 125

Glu Ile Met Met Ala Gly Ile Thr Lys Tyr Asp Leu Gly Ile Glu Ala
    130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Ile Asn Thr Pro Trp Tyr Tyr Asp Pro Ser Leu
        195                 200                 205

Lys Leu Ser Ile Glu Gly Gly Asp Val Phe Ile Tyr Asn Asn Asp Thr
    210                 215                 220

Leu Val Val Gly Val Ser Glu Arg Thr Asp Leu Gln Thr Val Thr Leu
225                 230                 235                 240

Leu Ala Lys Asn Ile Val Ala Asn Lys Glu Ser Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285
```

```
Asn Asp Val Phe Lys Phe Trp Asp Tyr Asp Leu Val Asn Gly Gly Ala
    290                 295                 300
Glu Pro Gln Pro Val Glu Asn Gly Leu Pro Leu Glu Gly Leu Leu Gln
305                 310                 315                 320
Ser Ile Ile Asn Lys Lys Pro Val Leu Ile Pro Ile Ala Gly Glu Gly
                325                 330                 335
Ala Ser Gln Met Glu Ile Glu Arg Glu Thr His Phe Asp Gly Thr Asn
                340                 345                 350
Tyr Leu Ala Ile Arg Pro Gly Val Val Ile Gly Tyr Ser Arg Asn Glu
                355                 360                 365
Lys Thr Asn Ala Ala Leu Glu Ala Ala Gly Ile Lys Val Leu Pro Phe
    370                 375                 380
His Gly Asn Gln Leu Ser Leu Gly Met Gly Asn Ala Arg Cys Met Ser
385                 390                 395                 400
Met Pro Leu Ser Arg Lys Asp Val Lys Trp
                405                 410

<210> SEQ ID NO 27
<211> LENGTH: 410
<212> TYPE: PRT
<213> ORGANISM: Artificial Sequence
<220> FEATURE:
<223> OTHER INFORMATION: mycoplasma arthritidis arginine deiminase with
      flanking synthesized residues added

<400> SEQUENCE: 27

Met Ser Val Phe Asp Ser Lys Phe Lys Gly Ile His Val Tyr Ser Glu
1               5                   10                  15
Ile Gly Glu Leu Glu Thr Val Leu Val His Glu Pro Gly Lys Glu Ile
                20                  25                  30
Asp Tyr Ile Thr Pro Ala Arg Leu Asp Glu Leu Leu Phe Ser Ala Ile
                35                  40                  45
Leu Glu Ser His Asp Ala Arg Lys Glu His Lys Glu Phe Val Ala Glu
    50                  55                  60
Leu Lys Lys Arg Gly Ile Asn Val Val Glu Leu Val Asp Leu Ile Val
65                  70                  75                  80
Glu Thr Tyr Asp Leu Ala Ser Lys Glu Ala Lys Glu Lys Leu Leu Glu
                85                  90                  95
Glu Phe Leu Asp Asp Ser Val Pro Val Leu Ser Asp Glu His Arg Ala
                100                 105                 110
Thr Val Lys Lys Phe Leu Gln Ser Gln Lys Ser Thr Arg Ser Leu Val
                115                 120                 125
Glu Tyr Met Ile Ala Gly Ile Thr Lys His Asp Leu Lys Ile Glu Ser
    130                 135                 140
Asp Leu Glu Leu Ile Val Asp Pro Met Pro Asn Leu Tyr Phe Thr Arg
145                 150                 155                 160
Asp Pro Phe Ala Ser Val Gly Asn Gly Val Thr Ile His Tyr Met Arg
                165                 170                 175
Tyr Lys Val Arg Gln Arg Glu Thr Leu Phe Ser Arg Phe Val Phe Ser
                180                 185                 190
Asn His Pro Lys Leu Val Asn Thr Pro Trp Tyr Tyr Asp Pro Ala Glu
                195                 200                 205
Gly Leu Thr Ile Glu Gly Gly Asp Val Phe Ile Tyr Asn Asn Asp Thr
    210                 215                 220
Leu Val Val Gly Val Ser Glu Arg Thr Asp Leu Gln Thr Ile Thr Leu
225                 230                 235                 240
```

```
Leu Ala Lys Asn Ile Lys Ala Asn Lys Glu Ser Glu Phe Lys Arg Ile
                245                 250                 255
Val Ala Ile Asn Val Pro Lys Trp Thr Asn Leu Met His Leu Asp Thr
            260                 265                 270
Trp Leu Thr Met Leu Asp Lys Asp Lys Phe Leu Tyr Ser Pro Ile Ala
        275                 280                 285
Asn Asp Val Phe Lys Phe Trp Asp Tyr Asp Leu Val Asn Gly Gly Asp
    290                 295                 300
Ala Pro Gln Pro Val Asp Asn Gly Leu Pro Leu Glu Asp Leu Leu Lys
305                 310                 315                 320
Ser Ile Ile Gly Lys Lys Pro Thr Leu Ile Pro Ile Ala Gly Ala Gly
                325                 330                 335
Ala Ser Gln Ile Asp Ile Glu Arg Glu Thr His Phe Asp Gly Thr Asn
            340                 345                 350
Tyr Leu Ala Val Ala Pro Gly Ile Val Ile Gly Tyr Ala Arg Asn Glu
        355                 360                 365
Lys Thr Asn Ala Ala Leu Glu Ala Ala Gly Ile Thr Val Leu Pro Phe
    370                 375                 380
Arg Gly Asn Gln Leu Ser Leu Gly Met Gly Asn Ala Arg Cys Met Ser
385                 390                 395                 400
Met Pro Leu Ser Arg Lys Asp Val Lys Trp
                405                 410

<210> SEQ ID NO 28
<211> LENGTH: 410
<212> TYPE: PRT
<213> ORGANISM: Artificial Sequence
<220> FEATURE:
<223> OTHER INFORMATION: mycoplasma phocicerebrale arginine deiminase
      with flanking synthesized residues added

<400> SEQUENCE: 28

Met Ser Val Phe Asp Ser Lys Phe Asn Gly Ile His Val Tyr Ser Glu
1               5                   10                  15
Ile Gly Glu Leu Glu Thr Val Leu Val His Glu Pro Gly Arg Glu Ile
            20                  25                  30
Asp Tyr Ile Thr Pro Ala Arg Leu Asp Glu Leu Leu Phe Ser Ala Ile
        35                  40                  45
Leu Glu Ser His Asp Ala Arg Lys Glu His Gln Ser Phe Val Lys Gln
    50                  55                  60
Leu Lys Asp Asn Gly Ile Asn Val Val Glu Leu Thr Asp Leu Val Ala
65                  70                  75                  80
Glu Thr Phe Asp Leu Ala Ser Lys Glu Gln Glu Lys Leu Ile Glu
                85                  90                  95
Glu Phe Leu Glu Asp Ser Glu Pro Val Leu Ser Glu Ala His Lys Thr
            100                 105                 110
Ala Val Arg Lys Phe Leu Thr Ser Arg Lys Ser Thr Arg Glu Met Val
        115                 120                 125
Glu Phe Met Met Ala Gly Ile Thr Lys Tyr Asp Leu Gly Ile Glu Ala
    130                 135                 140
Asp His Glu Leu Ile Val Asp Pro Met Pro Asn Leu Tyr Phe Thr Arg
145                 150                 155                 160
Asp Pro Phe Ala Ser Val Gly Asn Gly Val Thr Ile His Tyr Met Arg
                165                 170                 175
Tyr Lys Val Arg Gln Arg Glu Thr Leu Phe Ser Arg Phe Val Phe Ser
```

```
                     180                 185                 190
Asn His Pro Lys Leu Val Lys Thr Pro Trp Tyr Tyr Asp Pro Ala Met
            195                 200                 205

Lys Met Ser Ile Glu Gly Gly Asp Val Phe Ile Tyr Asn Asn Asp Thr
    210                 215                 220

Leu Val Val Gly Val Ser Glu Arg Thr Asp Leu Glu Thr Ile Thr Leu
225                 230                 235                 240

Leu Ala Lys Asn Ile Lys Ala Asn Lys Glu Val Glu Phe Lys Arg Ile
            245                 250                 255

Val Ala Ile Asn Val Pro Lys Trp Thr Asn Leu Met His Leu Asp Thr
        260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Ala
        290                 295                 300

Glu Pro Gln Pro Lys Glu Asn Gly Leu Pro Leu Glu Gly Leu Leu Gln
305                 310                 315                 320

Ser Ile Ile Asn Lys Lys Pro Val Leu Ile Pro Ile Ala Gly Asn Asn
            325                 330                 335

Ala Ser His Ile Asp Ile Glu Arg Glu Thr His Phe Asp Gly Thr Asn
        340                 345                 350

Tyr Leu Ala Ile Lys Pro Gly Val Val Ile Gly Tyr Ala Arg Asn Glu
        355                 360                 365

Lys Thr Asn Ala Ala Leu Ala Ala Ala Gly Ile Lys Val Leu Pro Phe
370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 29
<211> LENGTH: 410
<212> TYPE: PRT
<213> ORGANISM: Artificial Sequence
<220> FEATURE:
<223> OTHER INFORMATION: mycoplasma gateae arginine deiminase with
      flanking synthesized residues added

<400> SEQUENCE: 29

Met Ser Val Phe Asp Ser Lys Phe Asn Gly Ile His Val Tyr Ser Glu
1               5                   10                  15

Ile Gly Glu Leu Glu Ser Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Lys Leu Phe Val Ser Glu
    50                  55                  60

Leu Lys Ala Asn Asp Ile Asn Val Val Glu Leu Thr Asp Leu Val Thr
65                  70                  75                  80

Glu Thr Tyr Asp Leu Ala Ser Gln Glu Ala Lys Asp Asn Leu Ile Glu
                85                  90                  95

Glu Phe Leu Glu Asp Ser Glu Pro Val Leu Thr Glu Glu Leu Lys Ser
            100                 105                 110

Val Val Arg Thr Tyr Leu Lys Ser Ile Lys Ser Thr Arg Glu Leu Ile
        115                 120                 125
```

```
Gln Met Met Met Ala Gly Ile Thr Lys Tyr Asp Leu Gly Ile Glu Ala
    130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Val Asn Thr Pro Trp Tyr Tyr Asp Pro Ser Leu
        195                 200                 205

Lys Leu Ser Ile Glu Gly Gly Asp Val Phe Ile Tyr Asn Asn Asn Thr
    210                 215                 220

Leu Val Val Gly Val Ser Glu Arg Thr Asp Leu Glu Thr Val Thr Leu
225                 230                 235                 240

Leu Ala Lys Asn Ile Val Ala Asn Lys Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Glu
    290                 295                 300

Glu Pro Gln Pro Val Glu Asn Gly Leu Pro Leu Glu Gly Leu Leu Glu
305                 310                 315                 320

Ser Ile Ile Asn Lys Lys Pro Ile Leu Ile Pro Ile Ala Gly Glu Gly
                325                 330                 335

Ala Ser Gln Ile Asp Ile Glu Arg Glu Thr His Phe Asp Gly Thr Asn
            340                 345                 350

Tyr Leu Ala Ile Arg Pro Gly Val Val Ile Gly Tyr Ser Arg Asn Glu
        355                 360                 365

Lys Thr Asn Ala Ala Leu Glu Ala Ala Gly Ile Lys Val Leu Pro Phe
    370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 30
<211> LENGTH: 410
<212> TYPE: PRT
<213> ORGANISM: Artificial Sequence
<220> FEATURE:
<223> OTHER INFORMATION: mycoplasma phocidae arginine deiminase with
      flanking synthesized residues added

<400> SEQUENCE: 30

Met Ser Val Phe Asp Ser Lys Phe Asn Gly Ile His Val Tyr Ser Glu
1               5                   10                  15

Ile Gly Glu Leu Gln Thr Val Leu Val His Glu Pro Gly Arg Glu Ile
            20                  25                  30

Glu Tyr Ile Thr Pro Ala Arg Leu Asp Glu Leu Leu Phe Ser Ala Ile
        35                  40                  45

Leu Glu Ser His Asp Ala Arg Lys Glu His Gln Glu Phe Val Ala Glu
    50                  55                  60

Leu Lys Lys Asn Asn Ile Asn Val Val Glu Leu Thr Asp Leu Val Ser
65                  70                  75                  80
```

```
Glu Thr Tyr Asp Met Val Ser Lys Glu Lys Gln Glu Lys Leu Ile Glu
                85                  90                  95

Glu Phe Leu Glu Asp Ser Glu Pro Val Leu Ser Glu Glu His Lys Gly
            100                 105                 110

Leu Val Arg Lys Phe Leu Lys Ser Leu Lys Ser Ser Lys Glu Leu Ile
        115                 120                 125

Gln Tyr Met Met Ala Gly Ile Thr Lys His Asp Leu Asn Ile Glu Ala
    130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Ile Phe Ala
            180                 185                 190

Asn His Pro Lys Leu Met Asn Thr Pro Leu Tyr Tyr Asn Pro Asp Met
        195                 200                 205

Lys Leu Ser Ile Glu Gly Gly Asp Val Phe Val Tyr Asn Asn Glu Thr
    210                 215                 220

Leu Val Val Gly Val Ser Glu Arg Thr Asp Leu Asp Thr Ile Thr Leu
225                 230                 235                 240

Leu Ala Lys Asn Ile Lys Ala Asn Lys Glu Arg Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Asp
    290                 295                 300

Glu Pro Gln Pro Lys Val Asn Gly Leu Pro Leu Glu Lys Leu Leu Glu
305                 310                 315                 320

Ser Ile Ile Asn Lys Lys Pro Ile Leu Ile Pro Ile Ala Gly Thr Ser
                325                 330                 335

Ala Ser Asn Ile Asp Val Glu Arg Glu Thr His Phe Asp Gly Thr Asn
            340                 345                 350

Tyr Leu Ala Ile Ala Pro Gly Val Val Ile Gly Tyr Ser Arg Asn Val
        355                 360                 365

Lys Thr Asn Glu Ala Leu Glu Ala Ala Gly Ile Lys Val Leu Pro Phe
    370                 375                 380

Lys Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 31
<211> LENGTH: 411
<212> TYPE: PRT
<213> ORGANISM: Artificial Sequence
<220> FEATURE:
<223> OTHER INFORMATION: mycoplasma H.orenii arginine deiminase with
      flanking synthesized residues added

<400> SEQUENCE: 31

Met Ser Phe Lys Lys Ser Pro Leu Asn Val Thr Ser Glu Ile Gly Lys
1               5                   10                  15

Leu Lys Lys Val Leu Leu His Arg Pro Gly His Glu Ile Glu Asn Leu
```

```
            20                  25                  30
Thr Pro Asp Leu Leu Glu Arg Leu Leu Phe Asp Asp Ile Pro Tyr Leu
            35                  40                  45

Lys Val Ala Gln Glu Glu His Asp Ala Phe Ala Gln Thr Leu Arg Asp
    50                  55                  60

Asn Gly Val Glu Val Leu Tyr Leu His Glu Leu Ala Ala Glu Ala Ile
65                  70                  75                  80

Gln Glu Asp Glu Ile Arg Lys Lys Phe Ile Glu Gln Phe Leu Asp Glu
                85                  90                  95

Ala Gly Val Ile Gly Lys Gly Ala Arg Gln Val Leu Lys Glu Tyr Phe
            100                 105                 110

Ala Asp Met Asp Asn Glu Thr Leu Ile Arg Lys Met Met Ala Gly Val
            115                 120                 125

Arg Lys Lys Glu Ile Pro Ala Ile Glu Lys Val Ala Ser Leu Asn Asp
            130                 135                 140

Met Val Glu Glu Asp Tyr Pro Phe Val Leu Asp Pro Met Pro Asn Leu
145                 150                 155                 160

Tyr Phe Thr Arg Asp Pro Phe Ala Thr Ile Gly Thr Gly Ile Thr Leu
                165                 170                 175

Asn His Met Arg Thr Glu Thr Arg Asn Arg Glu Val Ile Phe Ala Glu
            180                 185                 190

Tyr Ile Phe Ser Tyr His Pro Asp Phe Lys Asp Thr Glu Ile Pro Phe
            195                 200                 205

Trp Phe Asp Arg Asn Glu Thr Thr Ser Ile Glu Gly Gly Asp Glu Leu
            210                 215                 220

Ile Leu Ser Asp Lys Val Leu Ala Met Gly Ile Ser Glu Arg Thr Asp
225                 230                 235                 240

Ala Ala Ser Ile Glu Lys Val Ala Arg Asn Ile Phe Thr Asp Gly Gln
                245                 250                 255

Pro Phe Glu Thr Ile Leu Ala Phe Lys Ile Pro Glu Lys Arg Ala Phe
            260                 265                 270

Met His Leu Asp Thr Val Phe Thr Met Val Asp Tyr Asp Lys Phe Thr
            275                 280                 285

Ile His Ala Glu Ile Glu Gly Pro Leu Lys Val Tyr Ser Ile Thr Lys
            290                 295                 300

Gly Asp Asn Asp Glu Leu Lys Ile Asp Glu Lys Ala Thr Leu Glu
305                 310                 315                 320

Asp Thr Leu Lys Lys Tyr Leu Gly Leu Asp Glu Val Thr Leu Ile Arg
                325                 330                 335

Cys Ala Gly Gly Asp Tyr Ile Asp Ala Gly Arg Glu Gln Trp Asn Asp
            340                 345                 350

Gly Ser Asn Thr Leu Ala Ile Ala Pro Gly Glu Val Val Tyr Asn
            355                 360                 365

Arg Asn His Thr Thr Asn Arg Leu Leu Glu Glu His Gly Ile Lys Leu
            370                 375                 380

His Val Ile Pro Ser Ser Glu Leu Ser Arg Gly Arg Gly Pro Arg
385                 390                 395                 400

Cys Met Ser Met Pro Leu Val Arg Glu Asp Ile
                405                 410

<210> SEQ ID NO 32
<211> LENGTH: 404
<212> TYPE: PRT
<213> ORGANISM: Artificial Sequence
```

```
<220> FEATURE:
<223> OTHER INFORMATION: mycobacterium bovis arginine deiminase with
      flanking synthesized residues added

<400> SEQUENCE: 32

Met Ser Val Gly Val Glu Leu Gly Ser Asn Ser Glu Val Gly Ala Leu
1               5                   10                  15

Arg Val Val Ile Leu His Arg Pro Gly Ala Glu Leu Arg Arg Leu Thr
            20                  25                  30

Pro Arg Asn Thr Asp Gln Leu Leu Phe Asp Gly Leu Pro Trp Val Ser
        35                  40                  45

Arg Ala Gln Asp Glu His Asp Glu Phe Ala Glu Leu Leu Ala Ser Arg
    50                  55                  60

Gly Ala Glu Val Leu Leu Leu Ser Asp Leu Leu Thr Glu Ala Leu His
65                  70                  75                  80

His Ser Gly Ala Ala Arg Met Gln Gly Ile Ala Ala Ala Val Asp Ala
                85                  90                  95

Pro Arg Leu Gly Leu Pro Leu Ala Gln Glu Leu Ser Ala Tyr Leu Arg
            100                 105                 110

Ser Leu Asp Pro Gly Arg Leu Ala His Val Leu Thr Ala Gly Met Thr
        115                 120                 125

Phe Asn Glu Leu Pro Ser Asp Thr Arg Thr Asp Val Ser Leu Val Leu
    130                 135                 140

Arg Met His His Gly Gly Asp Phe Val Ile Glu Pro Leu Pro Asn Leu
145                 150                 155                 160

Val Phe Thr Arg Asp Ser Ser Ile Trp Ile Gly Pro Arg Val Val Ile
                165                 170                 175

Pro Ser Leu Ala Leu Arg Ala Arg Val Arg Glu Ala Ser Leu Thr Asp
            180                 185                 190

Leu Ile Tyr Ala His His Pro Arg Phe Thr Gly Val Arg Arg Ala Tyr
        195                 200                 205

Glu Ser Arg Thr Ala Pro Val Glu Gly Gly Asp Val Leu Leu Leu Ala
    210                 215                 220

Pro Gly Val Val Ala Val Gly Val Gly Glu Arg Thr Thr Pro Ala Gly
225                 230                 235                 240

Ala Glu Ala Leu Ala Arg Ser Leu Phe Asp Asp Asp Leu Ala His Thr
                245                 250                 255

Val Leu Ala Val Pro Ile Ala Gln Gln Arg Ala Gln Met His Leu Asp
            260                 265                 270

Thr Val Cys Thr Met Val Asp Thr Asp Thr Met Val Met Tyr Ala Asn
        275                 280                 285

Val Val Asp Thr Leu Glu Ala Phe Thr Ile Gln Arg Thr Pro Asp Gly
    290                 295                 300

Val Thr Ile Gly Asp Ala Ala Pro Phe Ala Glu Ala Ala Ala Lys Ala
305                 310                 315                 320

Met Gly Ile Asp Lys Leu Arg Val Ile His Thr Gly Met Asp Pro Val
                325                 330                 335

Val Ala Glu Arg Glu Gln Trp Asp Asp Gly Asn Asn Thr Leu Ala Leu
            340                 345                 350

Ala Pro Gly Val Val Val Ala Tyr Glu Arg Asn Val Gln Thr Asn Ala
        355                 360                 365

Arg Leu Gln Asp Ala Gly Ile Glu Val Leu Thr Ile Ala Gly Ser Glu
    370                 375                 380
```

```
Leu Gly Thr Gly Arg Gly Gly Pro Arg Cys Met Ser Cys Pro Ala Ala
385                 390                 395                 400
Arg Asp Pro Leu
```

What is claimed is:

1. A therapeutic composition comprising a pegylated arginine deiminase and a pharmaceutically-acceptable carrier, wherein the pegylated arginine deiminase is covalently bonded via a linker to at least one PEG molecule, displays at least 95% sequence identity to the polypeptide sequence of SEQ ID NO:8, has arginine deiminase activity of at least 45 IU/mg at 37° C. and physiological pH of human blood and retains at least 80% of the arginine deiminase activity of the unmodified arginine deiminase of SEQ ID NO:8, and wherein the pegylated arginine deiminase has reduced cross-reactivity with human patient anti-ADI-PEG 20 antibodies and has a Kcat or a Km or a combination thereof that is better than ADI-PEG 20.

2. The therapeutic composition of claim 1 wherein the isolated arginine deiminase has the amino acid sequence set forth in SEQ ID NO:8.

3. The therapeutic composition of claim 1 wherein the isolated arginine deiminase has been modified to remove at least one pegylation site.

4. The therapeutic composition of claim 1 wherein at least one lysine residue has been modified by an amino acid substitution.

5. The therapeutic composition of claim 1 wherein thearginine deiminase is covalently bonded to more than one PEG molecule.

6. The therapeutic composition of claim 1 wherein the arginine deiminase is covalently bonded to about 1 to about 10 PEG molecules.

7. The therapeutic composition of claim 1 wherein the arginine deiminase is covalently bonded to about 2 to about 8 PEG molecules.

8. The therapeutic composition of claim 1 wherein the PEG molecules are straight chain or branch chain PEG molecules.

9. The therapeutic composition of claim 1 wherein the at least one PEG has a total weight average molecular weight of from about 1,000 to about 40,000.

10. The therapeutic composition of claim 1 wherein the at least one PEG has a total weight average molecular weight of from about 10,000 to about 30,000.

11. The therapeutic composition of claim 1 wherein the linker is a succinyl group, an amide group, an imide group, a carbamate group, an ester group, an epoxy group, a carboxyl group, a hydroxyl group, a carbohydrate, a tyrosine group, a cysteine group, a histidine group, a methylene group, or any combinations thereof.

12. The therapeutic composition of claim 11 wherein the source of the succinyl group is succinimidyl succinate, succinimidyl succinimide, or succinimidyl propionate.

13. The therapeutic composition of claim 1 further comprising a chemotherapeutic agent.

14. The therapeutic composition of claim 13 wherein the chemotherapeutic agent is selected from the group consisting of docetaxel, carboplatin, cyclophosphamide, gemcitabine, cisplatin, sorafenib, sunitinib and everolimus.

15. A method of treating, ameliorating the symptoms of, or inhibiting the progression of a cancer comprising administering to a patient in need thereof a therapeutically effective amount of a therapeutic composition of claim 1, thereby treating, ameliorating the symptoms of, or inhibiting the progression of the cancer.

16. The method of claim 15 wherein the patient in need thereof has been determined to have anti-ADI-PEG 20 antibodies.

17. The method of claim 15 wherein the cancer is selected from the group consisting of hepatocellular carcinoma, melanoma, metastatic melanoma, pancreatic cancer, prostate cancer, small cell lung cancer, mesothelioma, lymphocytic leukemia, chronic myelogenous leukemia, lymphoma, hepatoma, sarcoma, leukemia, acute myeloid leukemia, relapsed acute myeloid leukemia, breast cancer, ovarian cancer, colorectal cancer, gastric cancer, glioma, glioblastoma multiforme, non-small cell lung cancer (NSCLC), kidney cancer, bladder cancer, uterine cancer, esophageal cancer, brain cancer, head and neck cancers, cervical cancer, testicular cancer, and stomach cancer.

18. A method of treating, ameliorating the symptoms of, or inhibiting the progression of a cancer comprising administering to a patient in need thereof a therapeutically effective amount of a composition comprising ADI-PEG 20, and after a period of time, administering to the patient a therapeutic composition of claim 1, thereby treating, ameliorating the symptoms of, or inhibiting the progression of the cancer.

19. The method of claim 18 wherein the period of time is determined by detecting a predetermined level of anti-ADI-PEG 20 antibodies in the patient, wherein the therapeutic composition is administered following detection of the predetermined level of said anti-ADI-PEG 20 antibodies.

20. The method of claim 18 wherein the period of time is determined by detecting ADI activity in the patient, wherein the therapeutic composition is administered following detection of a predetermined or reduced level of ADI activity.

* * * * *